(12) United States Patent
Heckel et al.

(10) Patent No.: US 7,560,480 B2
(45) Date of Patent: Jul. 14, 2009

(54) ALKYL-CONTAINING 5-ACYLINDOLINONES, THE PREPARATION THEREOF AND THEIR USE AS MEDICAMENTS

(75) Inventors: Armin Heckel, Biberach (DE); Gerald Juergen Roth, Biberach (DE); Joerg Kley, Mittelbiberach (DE); Stefan Hoerer, Ochsenhausen (DE); Ingo Uphues, Ummendorf (DE)

(73) Assignee: Boehringer Ingelheim International GmbH, Ingelheim (DE)

( * ) Notice: Subject to any disclaimer, the term of this patent is extended or adjusted under 35 U.S.C. 154(b) by 631 days.

(21) Appl. No.: 11/077,399

(22) Filed: Mar. 10, 2005

(65) Prior Publication Data

US 2005/0209302 A1 Sep. 22, 2005

Related U.S. Application Data

(60) Provisional application No. 60/559,471, filed on Apr. 5, 2004.

(30) Foreign Application Priority Data

Mar. 12, 2004 (DE) .................. 10 2004 012 068

(51) Int. Cl.
A61K 31/404 (2006.01)
A61K 31/4045 (2006.01)
A61K 31/4439 (2006.01)
C07D 401/12 (2006.01)
C07D 209/34 (2006.01)

(52) U.S. Cl. .................. 514/418; 514/339; 548/486; 546/277.7

(58) Field of Classification Search ................ 514/418, 514/339; 548/486; 546/277.7
See application file for complete search history.

(56) References Cited

U.S. PATENT DOCUMENTS 7,176,231 B2 2/2007 Heckel et al.

FOREIGN PATENT DOCUMENTS

WO WO 01/27080 A 4/2001

OTHER PUBLICATIONS

Bhat et al. Journal of Neurochemistry 2004, 89, 1313-1317.*
Wojtazsewski et al. Diabetes 2001, 50, 265-269.*
Eldar-Finkelman, H. Trends in Molecular Medicine, 2002, 8(3), 126-132.*
International Search Report for PCT/EP2005/002406 mailed Jun. 13, 2005.
Philip Cohen, et al; Timeline: The Renaissance of GSK3; Nature Reviews Molecular Cell Biology (2001) vol. 2, No. 10 pp. 769-776.
Darren A. E. Cross, et al; Selective Small-Molecule Inhibitors of Glycogen Synthase Kinase-3 Activity Protect Primary Neurones From Death; Journal of Neurochemistry (2001) Vol. 77 pp. 94-102.
Noor Embi, et al; Glycogen Synthase Kinase-3 from Rabbit Skeletal Muscle; Eur. J. Biochemistry (1980) vol. 107 pp. 519-527.
Noboru Sato, et al; Maintenance of Pluripotency in Human and Mouse Embryonic Stem Cells Through Activation of Ent Signaling by a Pharmacological GSK-3-Specific Inhibitor; Nature Medicine (2004) vol. 10, No. 1 pp. 55-63.
Svetiana E. Nikoulina, et al.; Potential Role of Glycogen Snthase Kinase-3 in Skeletal Muscle insulin Resistance of Type 2 Diabetes; Diabetes (2000) vol. 49 pp. 263-271.

* cited by examiner

*Primary Examiner*—Rebecca L Anderson
*Assistant Examiner*—Jason Nolan
(74) *Attorney, Agent, or Firm*—Michael P. Morris; Edouard G. Lebel; David A. Dow

(57) ABSTRACT

The present invention relates to alkyl-containing 5-acylindolinones of general formula

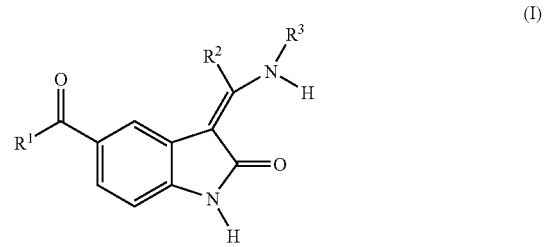

(I)

wherein $R^1$ to $R^3$ are defined herein, the tautomers, the enantiomers, the diastereomers, the mixtures thereof and the salts thereof, which have valuable pharmacological properties, particularly an inhibiting effect on protein kinases, particularly an inhibiting effect on the activity of glycogen synthase kinase (GSK-3).

11 Claims, No Drawings

ALKYL-CONTAINING 5-ACYLINDOLINONES, THE PREPARATION THEREOF AND THEIR USE AS MEDICAMENTS

RELATED APPLICATIONS

This application claims priority benefit under 35 USC 119 (e) from U.S. Provisional Application 60/559,471 filed Apr. 5, 2004, which claims benefit from German Application DE 10 2004 012 068.4, filed Mar. 12, 2004.

DESCRIPTION OF THE INVENTION

The present invention relates to new alkyl-containing 5-acylindolinones of general formula

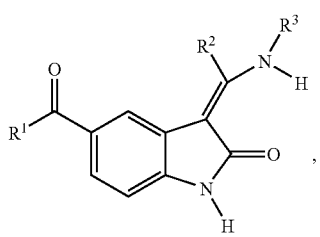

(I)

the tautomers, the enantiomers, the diastereomers, the mixtures thereof and the salts thereof, particularly the physiologically acceptable salts thereof with inorganic or organic acids or bases, which have valuable pharmacological properties, for example an inhibiting effect on protein kinases, particularly an inhibiting effect on the activity of glycogen-synthase-kinase (GSK-3), the preparation thereof, the use thereof for the prevention or treatment of diseases or conditions associated with an altered GSK-3 activity, particularly type I and type II diabetes mellitus, diabetes associated disorders such as diabetic neuropathy, degenerative neurological diseases such as Alzheimer's disease, stroke, neurotraumatic injuries, bipolar disorders, pharmaceutical compositions containing a compound of general formula (I) or a physiologically acceptable salt thereof and processes for the preparation thereof.

In the above formula I $R^1$ denotes a straight-chain or branched $C_{1-5}$-alkyl group wherein the hydrogen atoms may be wholly or partly replaced by fluorine atoms, or an aryl group optionally substituted by a fluorine, chlorine or bromine atom, while by an aryl group is meant a phenyl or naphthyl group, $R^2$ denotes a $C_{1-7}$-alkyl or $C_{3-7}$-cycloalkyl group, a 5- or 6-membered heteroaryl group with one to three heteroatoms selected from the group N, S and O, while both the heteroatoms and the substituents may be identical or different, optionally substituted by one or two fluorine, chlorine, bromine or iodine atoms or one or two nitro, cyano, amino, $C_{1-3}$-alkyl or $C_{1-3}$-alkoxy groups, a phenyl group wherein two adjacent carbon atoms are linked together through a methylenedioxy, ethylenedioxy or difluoromethylenedioxy group, a phenyl group, to which is anellated another phenyl ring or a 5- or 6-membered heteroaromatic ring with one to three heteroatoms selected from the group N, S and O, while the heteroatoms may be identical or different, and the bicyclic group may be substituted by one or two fluorine, chlorine, bromine or iodine atoms or one or two nitro, cyano, amino, $C_{1-3}$-alkyl or $C_{1-3}$-alkoxy groups and the substituents may be identical or different, or a phenyl group which may be substituted by one to three fluorine, chlorine, bromine or iodine atoms or by one to three $C_{1-3}$-alkyl, nitro, cyano, amino, di-($C_{1-3}$-alkyl)-amino, $C_{1-3}$-alkyl-carbonylamino, phenylcarbonylamino, $C_{1-3}$-alkylsulphonylamino, arylsulphonylamino, trifluoromethyl, $C_{1-3}$alkylsulphonyl, carboxy, $C_{1-3}$-alkoxy, di-($C_{1-3}$-alkyl)-amino-$C_{1-3}$-alkyloxy, $C_{1-3}$-alkoxy-carbonyl, $C_{1-3}$-alkylaminocarbonyl, hydroxy-carbonyl-$C_{1-3}$-alkyl-aminocarbonyl, $C_{1-3}$-alkoxycarbonyl-$C_{1-3}$-alkyl-aminocarbonyl, di-($C_{1-3}$-alkyl)-amino-$C_{1-3}$-alkylaminocarbonyl, di-($C_{1-3}$-alkyl)-amino-carbonyl-$C_{1-3}$-alkoxy, $C_{1-3}$-alkyl-amino-carbonyl-$C_{1-3}$-alkoxy, carboxy-$C_{1-3}$-alkoxy, $C_{1-3}$-alkyloxy-carbonyl-$C_{1-3}$-alkoxy, carboxy-$C_{1-3}$-alkyl, $C_{1-3}$-alkoxy-carbonyl-$C_{1-3}$-alkyl, $C_{1-3}$-alkoxy-carbonyl-amino-$C_{1-3}$-alkyl, amino-$C_{1-3}$-alkyl, di-($C_{1-3}$-alkyl)-amino-$C_{1-3}$-alkyl, $C_{1-3}$-alkyl-carbonyl-amino-$C_{1-3}$-alkyl, phthalimido, pyrrolyl or mono- or di-($C_{1-3}$-alkyl)-pyrrolyl groups, while the substituents are identical or different, and $R^3$ denotes a hydrogen atom, a straight-chain or branched $C_{1-6}$-alkyl group which may be substituted by one to three carboxy, $C_{1-4}$-alkoxy-carbonyl, aminocarbonyl, $C_{1-3}$-alkylaminocarbonyl, di-($C_{1-3}$-alkyl)-aminocarbonyl, di-($C_{1-3}$-alkyl)-amino-($C_{1-3}$-alkyl)-amino-carbonyl, N-[di-($C_{1-3}$-alkyl)-amino-($C_{1-3}$-alkyl)]-N-($C_{1-3}$-alkyl)-amino-carbonyl, arylaminocarbonyl, heteroarylaminocarbonyl, aryl-$C_{1-3}$-alkyl-aminocarbonyl, heteroaryl-$C_{1-3}$-alkyl-aminocarbonyl, N-(aryl)-N-($C_{1-3}$-alkyl)-aminocarbonyl, N-(heteroaryl)-N-($C_{1-3}$-alkyl)-aminocarbonyl, di-(ω-hydroxy-$C_{2-3}$-alkyl)-aminocarbonyl, aryl or heteroaryl groups or by a 5 to 7-membered cycloalkyleneimino or cycloalkyleneiminocarbonyl group, while in the above-mentioned cycloalkyleneimino or cycloalkyleneimino-carbonyl group a methylene group may be replaced in position 3 or 4 by an —NH—, —N($C_{1-3}$-alkyl)- or —N($C_{1-4}$-alkoxy-carbonyl)-group or by an oxygen or sulphur atom and/or in position 2, 3 or 4 by a carbonyl group, a straight-chain or branched $C_{2-6}$-alkyl group which is substituted from position 2 onwards by one to three hydroxy, $C_{1-3}$-alkoxy, aryloxy, heteroaryloxy, amino-$C_{1-3}$-alkyloxy, $C_{1-3}$-alkyl-amino-$C_{1-3}$-alkyloxy, di-($C_{1-3}$-alkyl)-amino-$C_{1-3}$-alkyloxy, ω-hydroxy-$C_{2-3}$-alkoxy, amino, $C_{1-3}$-alkylamino, di-($C_{1-3}$-alkyl)-amino, $C_{1-3}$-alkyl-carbonylamino, heteroaryl-carbonylamino, N—($C_{1-3}$-alkyl)-N—($C_{1-3}$-alkyl-carbonyl)-amino, N—($C_{1-3}$-alkyl)-N-(heteroarylcarbonyl)-amino, $C_{1-4}$-alkoxy-carbonylamino, N—($C_{1-3}$-alkyl)-N—($C_{1-4}$-alkoxy-carbonyl)-amino, arylcarbonylamino, N—($C_{1-3}$-alkyl)-N-(aryl-carbonyl)-amino, (ω-hydroxy-$C_{2-3}$-alkyl)-amino, di-(ω-hydroxy-$C_{2-3}$-alkyl)-amino, arylamino, heteroarylamino, $C_{1-3}$-alkylsulphonylamino, N—($C_{1-3}$-alkyl)-N—($C_{1-3}$-alkyl-sulphonyl)-amino, $C_{1-3}$-alkoxy-carbonyl-$C_{1-3}$-alkyl-carbonylamino, ($C_{1-3}$-alkyl-amino)-carbonyl-amino, [di-($C_{1-3}$-alkyl)-amino]-carbonyl-amino, ($C_{1-3}$-alkyl-amino)-$C_{1-3}$-alkyl-carbonyl-amino, [di-($C_{1-3}$-alkyl)-amino]-$C_{1-3}$-alkyl-carbonyl-amino, N-(aryl-$C_{1-13}$-alkyl-carbonyl)-N—($C_{1-3}$-alkyl)-amino, N—($C_{1-3}$-alkyl)-N—[($C_{1-3}$-alkyl-amino)-carbonyl]-amino or N—($C_{1-3}$-alkyl)-N-{[di-($C_{1-3}$-alkyl)-amino]-carbonyl}-amino group and may optionally additionally be substituted from position 1 onwards by a carboxy, $C_{1-4}$-alkoxy-carbonyl, $C_{1-3}$-alkylaminocarbonyl, di-($C_{1-3}$-alkyl)-aminocarbonyl, arylamino-carbonyl, heteroarylaminocarbonyl-, di-(ω-hydroxy-$C_{2-3}$-alkyl)-aminocarbonyl-, aryl or heteroaryl group or by a 5 to 7-membered cycloalkyleneimino or cycloalkyleneimino-carbonyl group, while in the above-mentioned cycloalkyleneimino or cycloalkyleneimino-carbonyl group a methylene group in position 3 or 4 may be replaced by an —NH—, —N($C_{1-3}$-alkyl)- or —N($C_{1-4}$-alkoxy-carbonyl)-group or by an oxygen or sulphur atom and/or in position 2, 3 or 4 by a carbonyl group, a $C_{2-4}$-alkenyl or $C_{2-4}$-alkynyl group, while between the nitrogen atom to which $R^3$ is bound and the multiple bond there is at least one $sp^3$-hybridised carbon atom and the alkenyl or alkynyl group may be substituted by one to three $C_{1-3}$-alkyl groups, a $C_{1-5}$-alkyl group in the methylene group which is adjacent to the nitrogen atom to which $R^3$ is bound may be replaced by an —NH—, or a —N($C_{1-3}$-alkyl)-group or by an oxygen atom, a $C_{1-4}$-alkyloxy group or an amino group which may be substituted by one or two $C_{1-3}$-alkyl, aryl, aryl-$C_{1-3}$-alkyl, $C_{1-3}$-alkyl-carbonyl, $C_{1-4}$-alkyloxy-carbonyl, arylcarbonyl or aryl-$C_{1-3}$-alkyl-carbonyl groups, while the substituents may be identical or different, while the above-mentioned alkyl groups may be straight-chain or branched, the tautomers, enantiomers, diastereomers, the mixtures thereof and the salts thereof.

Unless otherwise stated, by a heteroaryl group or a heteroaromatic ring is preferably meant a furanyl, thiophenyl, pyrrolyl, pyrazolyl, thiazolyl, imidazolyl, oxazolyl, triazolyl, thiadiazolyl, pyridinyl, pyrimidinyl or pyrazinyl group, which may be mono-, di- or trisubstituted by a fluorine, chlorine, bromine or iodine atom or an amino, nitro, cyano, $C_{1-3}$-alkyl, $C_{1-3}$-alkyloxy, di-($C_{1-3}$-alkyl)-amino-$C_{1-3}$-alkyloxy, or trifluoromethyl group, while the substituents are identical or different, and to which a phenyl ring may be fused via two adjacent atoms.

By an aryl group is meant, unless otherwise stated, a phenyl or naphthyl group; the phenyl group is preferred. Unless otherwise stated, an aryl group of this kind may be substituted by a nitro, cyano, $C_{1-3}$-alkyloxy, di-($C_{1-3}$-alkyl)-amino-$C_{1-3}$-alkyloxy, amino-$C_{1-3}$-alkyl, $C_{1-3}$-alkyl-amino-$C_{1-3}$-alkyl, di-($C_{1-3}$-alkyl)-amino-$C_{1-3}$-alkyl or $C_{1-4}$-alkoxy-carbonylamino-$C_{1-3}$-alkyl group.

Preferred are those compounds of general formula I, wherein $R^2$ and $R^3$ are as hereinbefore defined and $R^1$ denotes a methyl, ethyl, n-propyl, isopropyl, n-pentyl, trifluoromethyl or phenyl group, the tautomers, enantiomers, diastereomers, the mixtures thereof and the salts thereof.

Particularly preferred are those compounds of general formula I, wherein $R^1$ denotes a methyl or ethyl group, $R^2$ denotes an ethyl, propyl, butyl or pentyl group, a pyridinyl, furanyl or pyrazinyl group, a phenyl group wherein two adjacent carbon atoms are linked together through a methylenedioxy, ethylenedioxy or difluoromethylenedioxy group, or a phenyl group which may be substituted by one or two fluorine, chlorine, bromine or iodine atoms or by one or two $C_{1-3}$-alkyl, nitro, cyano, amino, $C_{1-3}$-alkylcarbonylamino, phenylcarbonylamino, $C_{1-3}$-alkylsulphonylamino, trifluoromethyl, carboxy, $C_{1-3}$-alkoxy, di-($C_{1-3}$-alkyl)-amino-$C_{1-3}$-alkyloxy, $C_{1-3}$-alkoxy-carbonyl, $C_{1-3}$-alkylaminocarbonyl, hydroxycarbonyl-$C_{1-3}$-alkyl-aminocarbonyl, $C_{1-3}$-alkoxycarbonyl-$C_{1-3}$-alkyl-aminocarbonyl, di-($C_{1-3}$-alkyl)-amino-$C_{1-3}$-alkylaminocarbonyl, carboxy-$C_{1-3}$-alkyl, $C_{1-3}$-alkoxy-carbonyl-$C_{1-3}$-alkyl, amino-$C_{1-3}$-alkyl or $C_{1-3}$-alkyl-carbonylamino-$C_{1-3}$-alkyl groups, while the substituents are identical or different, and $R^3$ denotes a hydrogen atom, a straight-chain or branched $C_{1-6}$-alkyl group which may be substituted by a carboxy, $C_{1-4}$-alkoxy-carbonyl, phenyl, pyridinyl, indolyl, imidazolyl, $C_{1-3}$-alkylaminocarbonyl, di-($C_{1-3}$-alkyl)-aminocarbonyl, phenylaminocarbonyl, pyridinylaminocarbonyl, di-(ω-hydroxy-$C_{2-3}$-alkyl)-aminocarbonyl or by a 5 to 7-membered cycloalkyleneimino or cycloalkyleneiminocarbonyl group, while the above-mentioned phenyl group may optionally be substituted by nitro, cyano, $C_{1-3}$-alkyloxy, [di-($C_{1-3}$-alkyl)-amino]-$C_{1-3}$-alkyloxy, an amino-$C_{1-3}$-alkyl or $C_{1-4}$-alkoxy-carbonylamino-$C_{1-3}$-alkyl group and in the above-mentioned cycloalkyleneimino and cycloalkyleneiminocarbonyl group a methylene group in position 3 or 4 may be replaced by an —NH—, —N($C_{1-3}$-alkyl)- or —N($C_{1-4}$-alkoxy-carbonyl)-group or by an oxygen or sulphur atom and/or in position 2, 3 or 4 by a carbonyl group, a straight-chain or branched $C_{2-6}$-alkyl group which is substituted from position 2 onwards by a hydroxy, $C_{1-3}$-alkoxy, ω-hydroxy-$C_{2-3}$-alkoxy, amino, $C_{1-3}$-alkylamino, di-($C_{1-3}$-alkyl)-amino, $C_{1-3}$-alkyl-carbonylamino, N—($C_{1-3}$-alkyl)-N—($C_{1-3}$-alkyl-carbonyl)-amino, $C_{1-4}$-alkoxy-carbonylamino, N—($C_{1-3}$-alkyl)-N—($C_{1-4}$-alkoxy-carbonyl)-amino, phenylcarbonylamino, N—($C_{1-3}$-alkyl)-N-(phenylcarbonyl)-amino, di-(ω-hydroxy-$C_{2-3}$-alkyl)-amino, pyridinylamino, nitro-pyridinyl-amino, chloro-trifluoromethyl-pyridinylamino, $C_{1-3}$-alkylsulphonylamino, N—($C_{1-3}$-alkyl)-N—($C_{1-3}$-alkylsulphonyl)-amino or $C_{1-3}$-alkoxy-carbonyl-$C_{1-3}$-alkyl-carbonylamino group and may optionally additionally be substituted from position 1 onwards by a carboxy, $C_{1-4}$-alkoxy-carbonyl, phenyl, pyridinyl, imidazolyl, $C_{1-3}$-alkylaminocarbonyl, di-($C_{1-3}$-alkyl)-aminocarbonyl, phenylaminocarbonyl, di-(ω-hydroxy-$C_{2-3}$-alkyl)-aminocarbonyl or by a 5 to 7-membered cycloalkyleneimino or cycloalkyleneiminocarbonyl group, while in the above-mentioned cycloalkyleneimino or cycloalkyleneimino-carbonyl group a methylene group in position 3 or 4 may be replaced by an —NH—, —N($C_{1-3}$-alkyl)- or —N($C_{1-4}$-alkoxy-carbonyl)-group or by an oxygen or sulphur atom and/or in position 2, 3 or 4 may be replaced by a carbonyl group, and the above-mentioned phenyl groups may optionally be substituted by an amino-$C_{1-3}$-alkyl or $C_{1-4}$-alkoxy-carbonylamino-$C_{1-3}$-alkyl group, or or represent a propenyl or propynyl group, but particularly those compounds wherein $R^1$ denotes a methyl group, $R^2$ denotes an ethyl, propyl, butyl or pentyl group, a phenyl group wherein two adjacent carbon atoms are linked together through a methylenedioxy, ethylenedioxy or difluoromethylenedioxy group, or a phenyl group which may be substituted by one or two fluorine, chlorine or bromine atoms or by one or two trifluoromethyl, nitro, cyano, $C_{1-3}$-alkoxy, carboxy-$C_{1-3}$-alkyl, $C_{1-3}$-alkoxy-carbonyl-$C_{1-3}$-alkyl, amino-$C_{1-3}$-alkyl or $C_{1-3}$-alkyl-carbonylamino-$C_{1-3}$-alkyl-groups, while the substituents are identical or different, and R³ denotes a straight-chain or branched C₁₋₅-alkyl group which may be substituted by a carboxy, C₁₋₄-alkoxy-carbonyl, C₁₋₃-alkylaminocarbonyl, di-(C₁₋₃-alkyl)-aminocarbonyl, phenylaminocarbonyl, pyridinylaminocarbonyl, di-(2-hydroxy-ethyl)-aminocarbonyl, piperazinylcarbonyl, 4-(C₁₋₃-alkyl)-piperazinyl-carbonyl, 4-(C₁₋₄-alkoxy-carbonyl)-piperazinyl-carbonyl, phenyl, pyridinyl or imidazolyl group,
  while the phenyl group may optionally be substituted by a nitro, cyano, C₁₋₃-alkyloxy, [di-(C₁₋₃-alkyl)-amino]-C₁₋₃-alkyloxy, amino-C₁₋₃-alkyl or C₁₋₄-alkoxy-carbonylamino-C₁₋₃-alkyl group,
a C₂₋₅-alkyl group which is terminally substituted by a hydroxy, C₁₋₃-alkoxy, phenyloxy, 2-hydroxy-ethoxy, amino, C₁₋₃-alkylamino, di-(C₁₋₃-alkyl)-amino, C₁₋₃-alkyl-carbonylamino, N—(C₁₋₃-alkyl)-N—(C₁₋₃-alkyl-carbonyl)-amino, C₁₋₄-alkoxy-carbonylamino, N—(C₁₋₃-alkyl)-N—(C₁₋₃-alkoxy-carbonyl)-amino, phenylcarbonylamino, N—(C₁₋₃-alkyl)-N-(phenylcarbonyl)-amino, pyridinylamino, nitro-pyridinyl-amino, di-(2-hydroxy-ethyl)-amino, 3-chloro-5-trifluoromethyl-pyridin-2-yl-amino, C₁₋₃-alkylsulphonylamino, N—(C₁₋₃-alkyl)-N—(C₁₋₃-alkylsulphonyl)-amino, C₁₋₃-alkoxy-carbonyl-C₁₋₃-alkyl-carbonylamino, indolyl, pyrrolidinyl, 2-oxo-pyrrolidinyl, morpholinyl, piperazinyl or 4-(C₁₋₃-alkyl)-piperazinyl group and may optionally additionally be substituted from position 1 onwards by a carboxy, C₁₋₄-alkoxy-carbonyl, C₁₋₃-alkylaminocarbonyl, di-(C₁₋₃-alkyl)-aminocarbonyl, phenylaminocarbonyl, di-(2-hydroxy-ethyl)-amino-carbonyl, piperazinylcarbonyl, 4-(C₁₋₃-alkyl)-piperazinyl-carbonyl, 4-(C₁₋₄-alkoxy-carbonyl)-piperazinyl-carbonyl, phenyl, pyridinyl or imidazolyl group, or
an amino group which may be substituted by one or two C₁₋₃-alkyl, aryl, aryl-C₁₋₃-alkyl, C₁₋₃-alkyl-carbonyl, C₁₋₄-alkyloxy-carbonyl, arylcarbonyl or aryl-C₁₋₃-alkyl-carbonyl groups, while the substituents may be identical or different,
while the above-mentioned alkyl groups may be straight-chain or branched, the tautomers, enantiomers, diastereomers, the mixtures thereof and the salts thereof.
  Most particularly preferred are those compounds of general formula I, wherein
R¹ denotes a methyl group,
R² denotes an ethyl, propyl, butyl or pentyl group,
a phenyl group wherein two adjacent carbon atoms are linked together through a methylenedioxy or ethylenedioxy group, or
a phenyl group and
R³ denotes a C₁₋₄-alkyl group which may be terminally substituted by a C₁₋₄-alkoxy-carbonyl group, or
a C₂₋₄-alkyl group which is terminally substituted by a C₁₋₃-alkyl-carbonylamino, phenylcarbonylamino, di-(C₁₋₃-alkyl)-amino, phenyl, pyridinyl or C₁₋₃-alkylsulphonylamino group,
while the above-mentioned alkyl groups may be straight-chain or branched,
the tautomers, enantiomers, diastereomers, the mixtures thereof and the salts thereof;
the following compounds of general formula I deserve particular mention:

(a) 5-acetyl-3-[3-(methoxycarbonylpropylamino)-(benzo[1,3]dioxol-5-yl)-methylidene]-2-indolinone

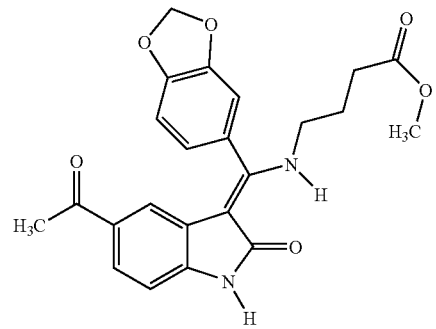

(b) 5-acetyl-3-[isopropylamino-phenyl-methylidene]-2-indolinone

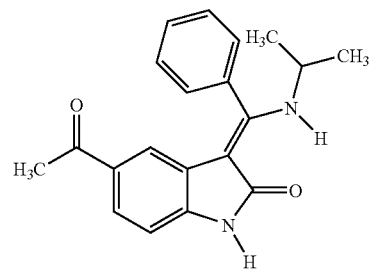

(c) 5-acetyl-3-[propylamino-phenyl-methylidene]-2-indolinone

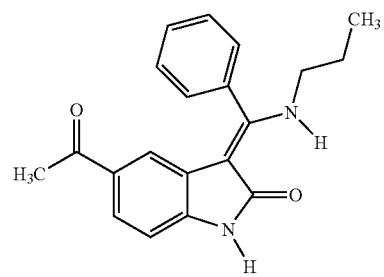

(d) 5-acetyl-3-[(3-methoxycarbonyl-propylamino)-(2,3-dihydro-benzo[1,4]dioxin-6-yl)-methylidene]-2-indolinone

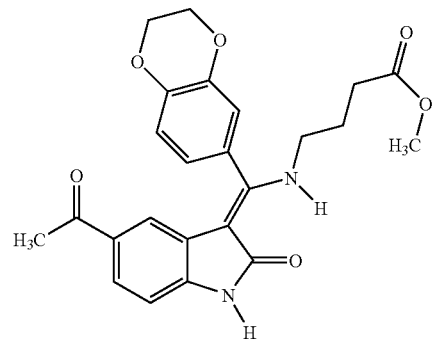

(e) 5-acetyl-3-[(benzo[1,3]dioxol-5-yl)-(3-(benzoylamino-propylamino)-methylidene]-2-indolinone

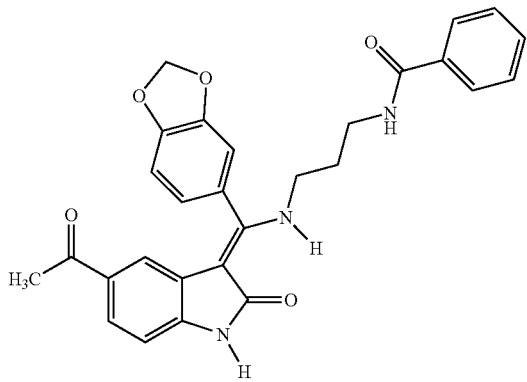

(f) 5-acetyl-3-[(benzo[1,3]dioxol-5-yl)-(3-(butyrylamino-propylamino)-methylidene]-2-indolinone

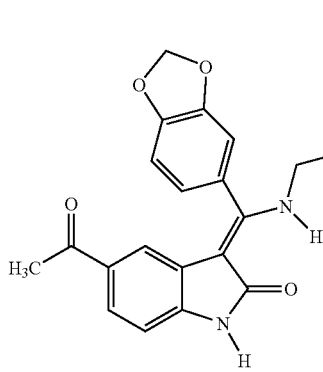

(g) 5-acetyl-3-[(3-methanesulphonylamino-propylamino)-phenyl-methylidene]-2-indolinone

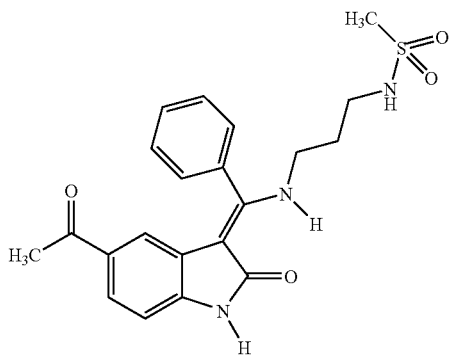

(h) 5-acetyl-3-[1-(3,4-difluorophenyl)-1-(N',N'-dimethylhydrazino)-methylidene]-2-indolinone

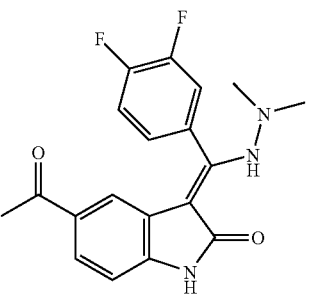

(i) 5-acetyl-3-[1-(4-dimethylamino-butyl)-butenylidene]-2-indolinone

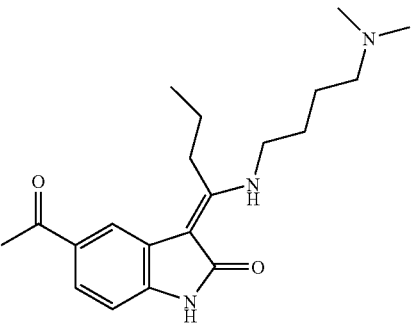

(j) 5-acetyl-3-[1-phenyl-1-(3-pyridin-3-yl-propylamino)-methylidene]-2-indolinone

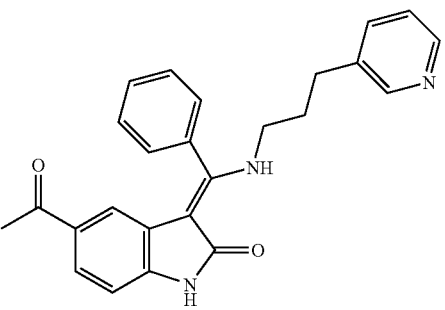

as well as the tautomers, enantiomers, diastereomers, the mixtures thereof and the salts thereof.

According to the invention the compounds of general formula I are obtained by methods known per se, for example by the following methods:

a) reacting a compound of general formula

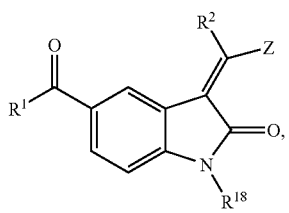

wherein $R^1$ and $R^2$ are as hereinbefore defined,
$R^{18}$ denotes a hydrogen atom or a protective group for the nitrogen atom of the lactam group and
Z denotes a leaving group such as e.g. a halogen atom, a hydroxy, alkoxy, alkyl-sulphonyl, trialkylsilyloxy-, alkyl-arylsulphonyl, or aryl-alkoxy group, e.g. a chlorine or bromine atom, a methoxy, ethoxy, methanesulphonyl, trimethylsilyloxy, toluene-sulphonyl or benzyloxy group,
with an amine of general formula

wherein $R^3$ is as hereinbefore defined, while any hydroxy, amino or imino groups optionally contained in the groups $R^2$ and/or $R^3$ may be temporarily protected by suitable protective groups.

A suitable protective group for the nitrogen atom of the lactam group may be for example an acetyl, benzoyl, ethoxycarbonyl, tert.butyloxycarbonyl or benzyloxycarbonyl group.

The reaction is expediently carried out in a solvent such as dimethylformamide, toluene, acetonitrile, tetrahydrofuran, dimethylsulphoxide, methylene chloride or mixtures thereof, optionally in the presence of an inert base such as triethylamine, N-ethyl-diisopropylamine or sodium hydrogen carbonate, at temperatures between 20 and 175° C., while any protective group used may simultaneously be cleaved as a result of transamidation.

If Z in a compound of general formula II denotes a halogen atom, then the reaction is preferably carried out in the presence of an inert base at temperatures between 20 and 120° C.

If Z in a compound of general formula II denotes a hydroxy, alkoxy or arylalkoxy group, then the reaction is preferably carried out at temperatures between 20 and 200° C.

If any protecting group used subsequently has to be cleaved, this is conveniently carried out either hydrolytically in an aqueous or alcoholic solvent, e.g. in methanol/water, ethanol/water, isopropanol/water, tetrahydrofuran/water, dioxane/water, dimethylformamide/water, methanol or ethanol in the presence of an alkali metal base such as lithium hydroxide, sodium hydroxide or potassium hydroxide at temperatures between 0 and 100° C., preferably at temperatures between 10 and 50° C., or advantageously by transamidation with an organic base such as ammonia, butylamine, dimethylamine or piperidine in a solvent such as methanol, ethanol, dimethylformamide and mixtures thereof or in an excess of the amine used at temperatures between 0 and 100° C., preferably at temperatures between 10 and 50° C.

b) in order to prepare a compound of formula I which contains an aminocarbonyl group:
reacting a compound which contains a carboxy group with the corresponding amine to obtain the corresponding aminocarbonyl compound;

c) in order to prepare a compound of formula I which contains a carbonylamino group:
reacting a compound which contains an amino group with the corresponding acid chloride to obtain the corresponding carbonylamino compound;

d) in order to prepare a compound of formula I which contains an aminomethyl group: hydrogenating a compound which contains a cyano group to obtain the corresponding aminomethyl derivative;

e) in order to prepare a compound of formula I which contains an amino group:

reducing a compound which contains a nitro group.

Then any protective groups optionally used during the reaction may be cleaved and/or
the compounds of general formula I thus obtained may be resolved into their enantiomers and/or diastereomers and/or
the compounds of formula I obtained may be converted into the salts thereof, particularly for pharmaceutical use into the physiologically acceptable salts thereof with inorganic or organic acids or bases.

Moreover, the compounds of general formula I obtained may be resolved into their enantiomers and/or diastereomers, as mentioned hereinbefore. Thus, for example, cis/trans mixtures may be resolved into their cis and trans isomers, and compounds with at least one optically active carbon atom may be separated into their enantiomers.

Thus, for example, the cis/trans mixtures obtained may be resolved by chromatography into the cis and trans isomers thereof, the compounds of general formula I obtained which occur as racemates may be separated by methods known per se (cf. Allinger N. L. and Eliel E. L. in "Topics in Stereochemistry", Vol. 6, Wiley Interscience, 1971) into their optical antipodes and compounds of general formula I with at least 2 asymmetric carbon atoms may be resolved into their diastereomers on the basis of their physical-chemical differences using methods known per se, e.g. by chromatography and/or fractional crystallisation, and, if these compounds are obtained in racemic form, they may subsequently be resolved into the enantiomers as mentioned above.

The enantiomers are preferably separated by column separation on chiral phases or by recrystallisation from an optically active solvent or by reacting with an optically active substance which forms salts or derivatives such as e.g. esters or amides with the racemic compound, particularly acids and the activated derivatives or alcohols thereof, and separating the diastereomeric mixture of salts or derivatives thus obtained, e.g. on the basis of their differences in solubility, whilst the free antipodes may be released from the pure diastereomeric salts or derivatives by the action of suitable agents. Optically active acids in common use are e.g. the D- and L-forms of tartaric acid or dibenzoyltartaric acid, di-o-tolyltartaric acid, malic acid, mandelic acid, camphorsulphonic acid, glutamic acid, aspartic acid or quinic acid. An optically active alcohol may be for example (+) or (−)-menthol and an optically active acyl group in amides, for example, may be a (+)-or (−)-menthyloxycarbonyl.

Furthermore, the compounds of formula I may be converted into the salts thereof, particularly for pharmaceutical use into the physiologically acceptable salts with inorganic or organic acids. Acids which may be used for this purpose include for example hydrochloric acid, hydrobromic acid, sulphuric acid, methanesulphonic acid, phosphoric acid, fumaric acid, succinic acid, lactic acid, citric acid, tartaric acid or maleic acid.

Moreover, if the new compounds of formula I contain a carboxy group, they may subsequently, if desired, be converted into the salts thereof with inorganic or organic bases, particularly for pharmaceutical use into the physiologically acceptable salts thereof. Suitable bases for this purpose include for example sodium hydroxide, potassium hydroxide, cyclohexylamine, ethanolamine, diethanolamine and triethanolamine.

The compounds of general formulae II to III used as starting materials are either known from the literature or may be obtained by methods known from the literature (cf. Examples I to VIII).

As already mentioned hereinbefore, the compounds according to the invention of general formula I and the physiologically acceptable salts thereof have valuable pharmacological properties, particularly an inhibiting effect on the enzyme GSK-3.

Glycogen synthase kinase-3 (GSK-3) is a serine/threonine kinase which exists in two isoforms, GSK-3α and GSK-3β. GSK-3 phosphorylates and inactivates not only glycogen synthase, a key enzyme of the insulin-dependent regulation of glycogen synthesis (Embi et al., Eur. J. Biochem. 107, 519-527, (1980)), but also a number of other regulatory proteins in vitro. These proteins include the microtubule associated protein Tau, elongation initiation factor 2b (eIF2b), β-catenin, axin, ATP-citratelyase, heat-shock-factor 1, c-jun, c-myc, c-myb, CREB and CEBPα. These different substrates imply a role for GSK-3 in numerous fields of cell metabolism, proliferation, differentiation and development.

Type 2 diabetes is characterised by insulin resistance in various tissues such as skeletal muscle, liver and fatty tissue and by altered secretion of insulin from the pancreas. The storage of glycogen in liver and muscle is of great importance for maintaining the glucose equilibrium. In type 2 diabetes the activity of glycogen synthase is reduced and thus the rate of glycogen synthesis is reduced. It has also been shown that GSK-3 is expressed to a greater extent in type 2 diabetic muscle and hence a reduced GSK-3 activity is associated with a reduced rate of glycogen synthesis (Nikoulina et al., diabetes 49, 263-271, (2000)). Inhibition of the GSK-3 activity stimulates glycogen synthase, thus intensifies glycogen synthesis and leads eventually to a reduction in the glucose levels. GSK-3 inhibition is therefore of therapeutic relevance for the treatment of type 1 and type 2 diabetes and also diabetic neuropathy.

Alzheimer's disease is characterised in that the microtubule-associated protein Tau is present in excessively strongly phosphorylated form (Cohen & Frame, Nature Reviews: Molecular Cell Biology, 2, 1-8, (2001)). GSK-3 phosphorylates many of these phosphorylations sites of Tau in vitro, thereby preventing binding to microtubules. As a result, Tau is available for increased filament assembly, which is at the root of Alzheimer's disease and other neurological diseases of neuronal degeneration. It has been shown that GSK-3 inhibitors such as insulin or lithium bring about partial dephosphorylation of Tau in neuronal cells (Cross et al., J. Neurochem. 77, 94-102 (2001)). GSK-3 inhibition may therefore be of therapeutic relevance for the treatment of degenerative neurological diseases such as Alzheimer's disease.

Inhibitors of GSK-3 activity may thus be of therapeutical and/or preventive benefit for a number of diseases where it is useful to inhibit GSK-3, such as diabetes and diabetes-associated diseases, chronic neurodegenerative diseases and dementias, such as Alzheimer's disease, Parkinson's syndrome, Pick's disease, dementia in subcortical arteriosclerotic encephalopathy (SAE), Huntington's chorea, multiple sclerosis, infectious diseases (meningoencephalitis, syphilis, brain abscess, Creutzfeldt-Jakob disease, AIDS), dementia complex with Lewy bodies, neurotraumatic diseases such as acute stroke, schizophrenia, manic depression, brain haemorrhage, alopecia, obesity, atherosclerotic cardiovaskular diseases, high blood pressure, PCO syndrome, metabolic syndrome, ischaemia, cancer, leukopenia, Down's syndrome, inflammations, immunodeficiency.

A new study (Sato, N. et al., Nature Medicine 10, 55-63 (2004)) shows that GSK-3 inhibitors may acquire the pluripotence of stem cells, which may open up new possibilities in the field of regenerative therapies using stem cells.

Determining the GSK-3 Activity

The effect of substances on the GSK-3 activity was carried out according to the following test method, based on the phosphorylation of a 26mer peptide (YRRM-VPPSPSLSRHSSFHQpSEDEEE) from glycogen synthase, the sequence of which contains the phosphorylation sites for GSK-3 and the prephosphorylation of which is indicated by (pS).

The test substance is dissolved in DMSO/water. GSK3β (University of Dundee, UK) dissolved in 10 mM MOPS (morpholinopropanesulphonic acid), 0.05 mM EDTA, 0.005% Brij, 2.5% glycerol, 0.05% mercaptoethanol, pH 7.0, is combined with 10 μM [$^{33}$P]-ATP, 0.25 μM of 26mer peptide and incubated with the dissolved substance in 50 mM tris, 10 mM $MgCl_2$, 0.1% mercaptoethanol, pH 7.5, at ambient temperature. The reaction was stopped by the addition of 75 mM phosphoric acid. The reaction mixture was transferred onto Phosphocellulose filter plates (Millipore) and filtered to dryness and washed twice with 75 mM phosphoric acid. The phosphorylation was determined by measuring the radioactivity on the filter in a scintillation counter (Topcount, Packard). The ability of a substance to inhibit GSK-3 is determined by comparing the signal of a reaction mixture containing various concentrations of the substance with the signal of the reaction mixture without any substance. The $IC_{50}$ values are calculated by non-linear regression analysis using GraphPad Prism software.

Typical $IC_{50}$ values for the substances investigated were between 0.0001 μM and 1 μM.

Determining Glycogen Synthesis

This test serves to investigate the effect of test substances on glycogen synthesis in cells.

C3A hepatoma cells (ATCC) are seeded at a density of 100000 cells/ml in 96-well plates and grown to confluence as a monolayer in the medium. The medium is removed and the cells are washed several times with PBS and then incubated in KRBH buffer (134 mM NaCl, 3.5 mM KCl, 1.2 mM $KH_2PO_4$, 0.5 mM $MgSO_4$, 1.5 mM $CaCl_2$, 5 mM $NaHCO_3$, 10 mM HEPES, pH 7.4) with 0.1% BSA and 0.5 mM glucose for 60 min at 37° C. Test substance and 0.2 μCi D-[U$^{14}$C] glucose (Amersham) are added and the cells are incubated for a further 60 min under the same conditions. After the removal of the incubation buffer the cells are washed several times with cold PBS and then lysed for 10 min at 37° C. and 10 min at ambient temperature with 1 M NaOH. The cell lysates are transferred onto filter plates and the glycogen is precipitated by incubating for 2 h with cold ethanol (70%) on ice. The precipitates are washed several times with ethanol and filtered to dryness. The glycogen synthesised is determined by measuring the radioactivity (14C-glucose incorporated) on the filter plates in a scintillation counter (Topcount, Packard).

The ability of a substance to stimulate glycogen synthesis is determined by comparing the signal of a reaction mixture containing various concentrations of the substance with the signal of the reaction mixture without any substance.

Oral Glucose Tolerance Test

Fasted db/db mice 7 to 9 weeks old (Janvier, France) are weighed and blood is taken from the tip of the tail. This blood is used for the first measurement of glucose on the basis of which the animals are randomised and divided into groups. The test substance to be tested may be given either orally or i.p. as a suspension in 0.5% Natrosol. 30 minutes after the administration of the substance the animals are given orally 2 g/kg glucose in a volume of 0.1 ml/100 g body weight dissolved in NaCl solution. Subsequently, the glucose values are determined from the tail blood using a glucometer (Ultra OneTouch, Lifescan) at specific time intervals [30, 60, 120 and 180 minutes after oral administration of the glucose].

For example, compound 1.009 exhibits a significant activity in the oral glucose tolerance test.

The compounds prepared according to the invention are well tolerated as, for example, after oral administration of 10 mg/kg of the compound of Example 1.009 to mice no changes were observed in the animals' behaviour.

The compounds according to the invention may also be used in combination with other active substances. Therapeutic agents which are suitable for such a combination include, for example, antidiabetic agents such as metformin, sulphonylureas (e.g. glibenclamid, tolbutamide, glimepiride), nateglinide, repaglinide, thiazolidinediones (e.g. rosiglitazone, pioglitazone), PPAR-gamma-agonists (e.g. GI 262570) and antagonists, PPAR-gamma/alpha modulators (e.g. KRP 297), alpha-glucosidase inhibitors (e.g. acarbose, voglibose), DPP-IV inhibitors, alpha2-antagonists, insulin and insulin analogues, GLP-1 and GLP-1 analogues (e.g. exendin-4) or amylin. The list also includes SGLT2-inhibitors such as T-1095, inhibitors of protein tyrosinephosphatase 1, substances that affect deregulated glucose production in the liver, such as e.g. inhibitors of glucose-6-phosphatase, or fructose-1,6-bisphosphatase, glycogen phosphorylase, glucagon receptor antagonists and inhibitors of phosphoenol pyruvate carboxykinase, pyruvate dehydrokinase, lipid lowering agents such as for example HMG-CoA-reductase inhibitors (e.g. simvastatin, atorvastatin), fibrates (e.g. bezafibrate, fenofibrate), nicotinic acid and the derivatives thereof, PPAR-alpha agonists, PPAR-delta agonists, ACAT inhibitors (e.g. avasimibe) or cholesterol absorption inhibitors such as, for example, ezetimibe, bile acid-binding substances such as, for example, cholestyramine, inhibitors of ileac bile acid transport, HDL-raising compounds such as CETP inhibitors or ABC1 regulators or active substances for treating obesity, such as sibutramine or tetrahydrolipostatin, dexfenfluramine, axokine, antagonists of the cannabinoid1 receptor, MCH-1 receptor antagonists, MC4 receptor agonists, NPY5 or NPY2 antagonists or β3-agonists such as SB-418790 or AD-9677 and agonists of the 5HT2c receptor.

In addition, combinations with drugs for influencing high blood pressure such as e.g. A-II antagonists or ACE inhibitors, diuretics, β-blockers, Ca-antagonists and others or combinations thereof are suitable.

Generally speaking, GSK-3 inhibitors may be administered in various ways: by oral, transdermal, intranasal or parenteral route or, in special cases, by intrarectal route. The preferred method of administration is by oral route daily, possibly several times a day. GSK-3 inhibitors are effective over wide dosage range. Thus, the dosage may be between 0.001 and 100 mg/kg, for example.

For this purpose, the compounds of formula I prepared according to the invention may be formulated, optionally together with other active substances, with one or more inert conventional carriers and/or diluents, e.g. with corn starch, lactose, glucose, microcrystalline cellulose, magnesium stearate, polyvinylpyrrolidone, citric acid, tartaric acid, water, water/ethanol, water/glycerol, water/sorbitol, water/polyethylene glycol, propylene glycol, cetylstearyl alcohol, carboxymethylcellulose or fatty substances such as hard fat or suitable mixtures thereof, to produce conventional galenic preparations such as plain or coated tablets, capsules, powders, suspensions or suppositories.

The Examples that follow are intended to illustrate the invention:

Preparation of the Starting Compounds:

EXAMPLE I 5-acetyl-2-indolinone

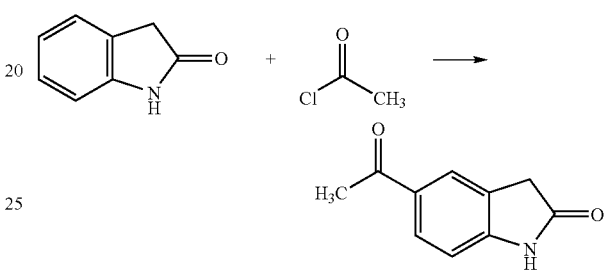

171 g (1.28 mol) aluminium chloride in 500 ml 1,2-dichloroethane are cooled in the ice bath. Then 78 g (1,1 mol) acetylchloride are added dropwise, so that the temperature does not exceed 10° C. After 1 h 71.3 g (0.53 mol) 2-indolinone (1,3-dihydro-indol-2-one) are added in 4 batches and the temperature is maintained at 10-12° C. The reaction mixture is left overnight to come up slowly to ambient temperature. Then the solution is slowly added to 1 kg ice with vigorous stirring. The slurry is diluted with 1 l water and stirred for another 30 min. Then the precipitate is suction filtered.

Yield: 80.9 g (86.3% of theory)
$R_f$=0.36 (silica gel, ethyl acetate/cyclohexane/methanol 9:9:2)
$C_{10}H_9NO_2$ (MW=175.19)
Mass spectrum: m/z=174 (M–H)⁻

The following compounds are prepared analogously to Example I:

(1) 5-propionyl-2-indolinone

Prepared from 2-indolinone and propionyl chloride
Yield: 72% of theory
$R_f$=0.44 (silica gel, methylene chloride/methanol 9:1)
$C_{11}H_{11}NO_2$(MW=189.22)
Mass spectrum: m/z=188 (M–H)⁻

(2) 5-butyryl-2-indolinone

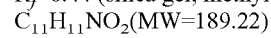

Prepared from 2-indolinone and butyric acid chloride (butyrylchloride)
Yield: 68% of theory
$C_{12}H_{13}NO_2$ (MW=203.24)
Mass spectrum: m/z=202 (M–H)⁻

(3) 5-isobutyryl-2-indolinone

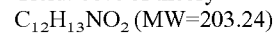

Prepared from 2-indolinone and isobutyrylchloride
Yield: 13% of theory $C_{12}H_{13}NO_2$ (MW=203.24)
Mass spectrum: m/z=202 (M–H)⁻

(4) 5-hexanoyl-2-indolinone

Prepared from 2-indolinone and hexanoic acid chloride
Yield: 88% of theory
$R_f$=0.51 (silica gel, ethyl acetate/cyclohexane/methanol 9:9:2)
$C_{14}H_{17}NO_2$ (MW=231.30)
Mass spectrum: m/z=230 (M–H)⁻

(5) 5-benzoyl-2-indolinone

Prepared from 2-indolinone and benzoic acid chloride
Yield: 80% of theory
$R_f$=0.46 (silica gel, methylene chloride/methanol 9:1)
$C_{15}H_{11}NO_2$ (MW=237.26)
Mass spectrum: m/z=236 (M–H)⁻

EXAMPLE II 1,5-diacetyl-2-indolinone

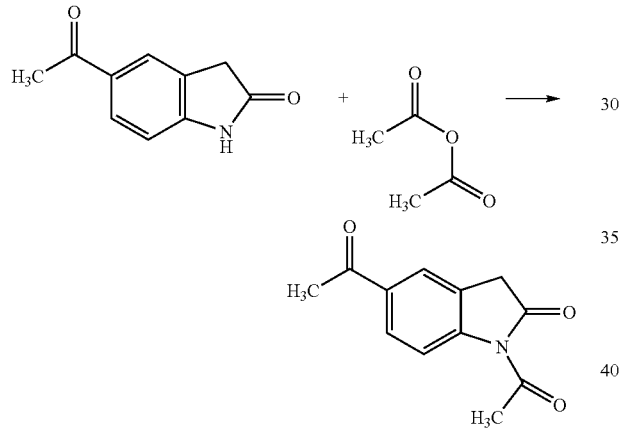

48.9 g (0.279 mol) 5-acetyl-2-indolinone are stirred in 400 ml acetic anhydride in an oil bath at 140° C. for 2 h. The starting material dissolves during this time.

Then the reaction mixture is left to cool, evaporated down, the precipitate is removed by suction filtering, washed with ether and the product is dried.

Yield: 56.0 g (92.4% of theory)
$R_f$=0.41 (silica gel, methylene chloride/methanol 50:1)
$C_{12}H_{11}NO_3$ (MW=217.223)
Mass spectrum: m/z=216 (M–H)⁻

The following compounds are prepared analogously to Example II:

(1) 1-acetyl-5-propionyl-2-indolinone

Prepared from 5-propionyl-2-indolinone and acetic anhydride
Yield: 79% of theory
$R_f$=0,68 (silica gel, methylene chloride/methanol 9:1)
$C_{13}H_{13}NO_3$ (MW=231.25)
Mass spectrum: m/z=232 (M+H)⁺

(2) 1-acetyl-5-benzoyl-2-indolinone

Prepared from 5-benzoyl-2-indolinone and acetic anhydride
Yield: 89% of theory
$R_f$=0,60 (silica gel, methylene chloride/methanol 30:1)
$C_{17}H_{13}NO_3$ (MW=279.294)
Mass spectrum: m/z=278 (M–H)⁻

(3) 1-acetyl-5-hexanoyl-2-indolinone

Prepared from 5-hexanoyl-2-indolinone and acetic anhydride
$R_f$=0,74 (silica gel, methylene chloride/methanol 30:1)
$C_{16}H_{19}NO_3$ (MW=273.33)
Mass spectrum: m/z=272 (M–H)⁻

EXAMPLE III 1,5-diacetyl-3-(ethoxy-phenyl-methylidene)-2-indolinone

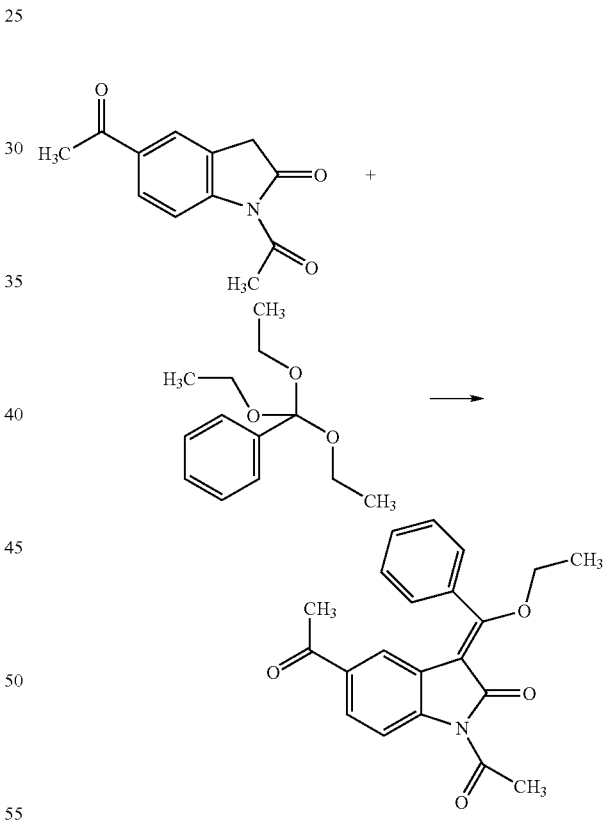

32.6 g (150 mmol) 1,5-diacetyl-2-indolinone are suspended in 100 ml triethyl orthobenzoate and stirred overnight at 110° C. with 150 ml acetic anhydride. Then another 50 ml triethyl orthobenzoate are added and the mixture is stirred for another 24 h. Then it is evaporated down and the resulting precipitate is suction filtered, washed and dried.

Yield: 38 g (72.5% of theory)
$R_f$=0.60 (silica gel, methylene chloride/methanol 30:1)
$C_{21}H_{19}NO_4$ (MW=349.384)
Mass spectrum: m/z=350 (M+H)⁺

The following compounds are prepared analogously to Example III:

(1) 1-acetyl-5-hexanoyl-3-(ethoxy-phenyl-methylidene)-2-indolinone

Prepared from 1-acetyl-5-hexanoyl-2-indolinone and triethyl orthobenzoate
Yield: 29% of theory
$R_f$=0,72 (silica gel, methylene chloride/methanol 30:1)
$C_{25}H_{27}NO_4$ (MW=405.491)
Mass spectrum: m/z=428 (M+Na)$^+$ (2) 1-acetyl-5-benzoyl-3-(ethoxy-phenyl-methylidene)-2-indolinone Prepared from 1-acetyl-5-benzoyl-2-indolinone and triethyl orthobenzoate
Yield: 65% of theory
$R_f$=0,72 (silica gel, methylene chloride/methanol 30:1)
$C_{26}H_{21}NO_4$ (MW=411.455)
Mass spectrum: m/z=412 (M+H)$^+$ (3) 1,5-diacetyl-3-(1-methoxy-propylidene)-2-indolinone Prepared from 1,5-diacetyl-2-indolinone and trimethyl orthopropionate
Yield: 80% of theory
$R_f$=0.50 (silica gel, methylene chloride/methanol 50:1)
$C_{16}H_{17}NO_4$ (MW=287.311)
Mass spectrum: m/z=288 (M+H)$^+$ (4) 1,5-diacetyl-3-(1-methoxy-butylidene)-2-indolinone Prepared from 1,5-diacetyl-2-indolinone and trimethyl orthobutyrate
Yield: 71% of theory
$R_f$=0.53 (silica gel, methylene chloride/methanol 50:1)
$C_{17}H_{19}NO_4$ (MW=301.337)
Mass spectrum: m/z=302 (M+H)$^+$ (5) 1,5-diacetyl-3-(1-methoxy-pentylidene)-2-indolinone Prepared from 1,5-diacetyl-2-indolinone and trimethyl orthovalerate
Yield: 66% of theory
$R_f$=0.60 (silica gel, methylene chloride/methanol 50:1)
$C_{18}H_{21}NO_4$ (MW=315.364)
Mass spectrum: m/z=316 (M+H)$^+$ (6) 1,5-diacetyl-3-(1-methoxy-2-methyl-propylidene)-2-indolinone Prepared from 1,5-diacetyl-2-indolinone and 1,1,1-trimethoxy-2-methylpropane
Yield: 40% of theory
$R_f$=0.71 (silica gel, ethyl acetate:cyclohexane:methanol 9:9:2)
$C_{17}H_{19}NO_4$ (MW=301.337)
Mass spectrum: m/z=302 (M+H)$^+$ (7) 1,acetyl-5-propionyl-3-(1-methoxy-propylidene)-2-indolinone Prepared from 1-acetyl-5-propionyl-2-indolinone and trimethyl orthopropionate (8) 1,acetyl-5-hexanonyl-3-(1-methoxy-propylidene)-2-indolinone Prepared from 1-acetyl-5-hexanoyl-2-indolinone and trimethyl orthopropionate

EXAMPLE IV 1-acetyl-5-butyryl-3-(ethoxy-phenyl-methylidene)-2-indolinone

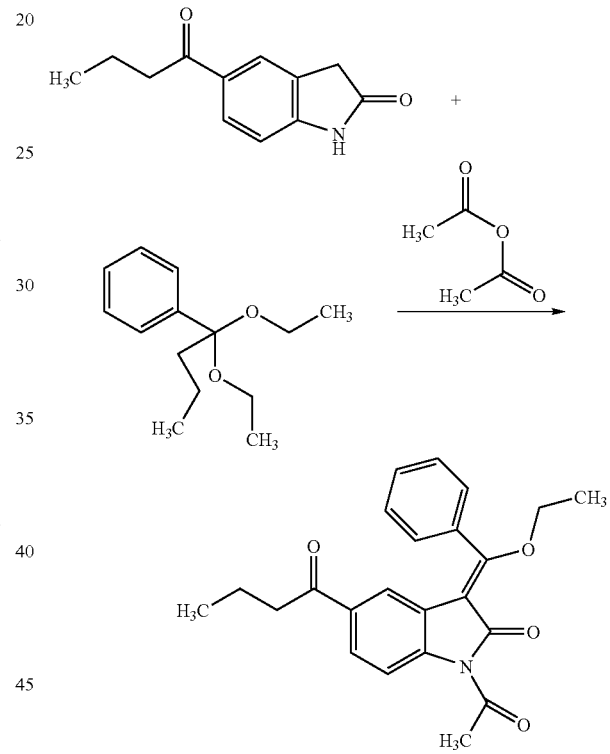

10 g (49 mmol) 5-butyryl-2-indolinone (Ex. 1.2) are stirred in 200 ml acetic anhydride for 5 h at 130° C. Then 35 ml triethyl orthobenzoate are added and the mixture is stirred for a further 4 h at 100° C. Then it is evaporated down and the resulting precipitate is suction filtered, washed and dried.
Yield: 11.5 g (62% of theory)
$R_f$=0.79 (silica gel, ethyl acetate/cyclohexane/methanol 9:9:2)
$C_{23}H_{23}NO_4$ (MW=377.438)
Mass spectrum: m/z=378 (M+H)$^+$ The following compounds are prepared analogously to Example IV:

(1) 1-acetyl-5-isobutyryl-3-(ethoxy-phenyl-methylidene)-2-indolinone

Prepared from 5-isobutyryl-2-indolinone, acetic anhydride and triethyl orthobenzoate $R_f$=0.55 (silica gel, ethyl acetate/cyclohexane/methanol 9:9:2)

(2) 1,5-diacetyl-3-[1-methoxy-ethylidene]-2-indolinone

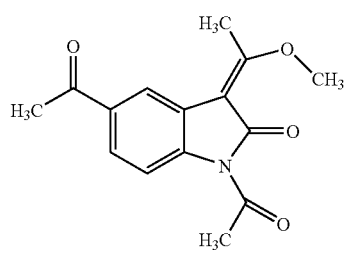

Prepared from 5-acetyl-2-indolinone, acetic anhydride and trimethyl orthoacetate
$R_f$=0.40 (silica gel, methylene chloride/methanol 50:1)

(3) 1-acetyl-5-propionyl-3-(ethoxy-phenyl-methylidene)-2-indolinone

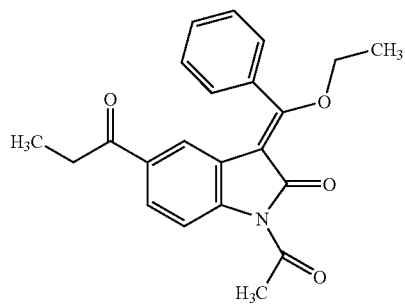

Prepared from 5-propionyl-2-indolinone, acetic anhydride and triethyl orthobenzoate
$R_f$=0.79 (silica gel, ethyl acetate/cyclohexane/methanol 9:9:2)

(4) 1-acetyl-5-hexanoyl-3-(ethoxy-phenyl-methylidene)-2-indolinone

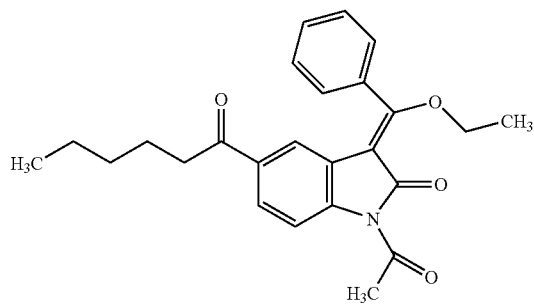

Prepared from 5-hexanoyl-2-indolinone, acetic anhydride and triethyl orthobenzoate
$R_f$=0.72 (methylene chloride/methanol 30:1)

(5) 1-acetyl-5-butyryl-3-(ethoxy-phenyl-methylidene)-2-indolinone

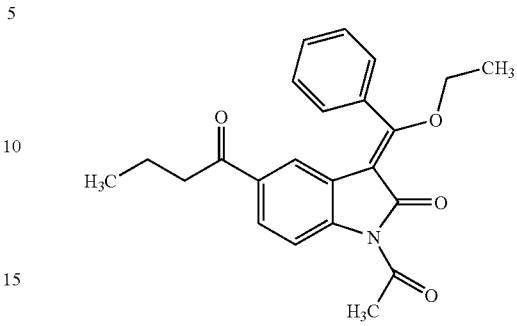

Prepared from 5-butyryl-2-indolinone, acetic anhydride and triethyl orthobenzoate
$R_f$=0.79 (silica gel, ethyl acetate/cyclohexane/methanol 9:9:2)

EXAMPLE V 1,5-diacetyl-3-[(3,4-dimethoxy-phenyl)-hydroxy-methylidene]-2-indolinone

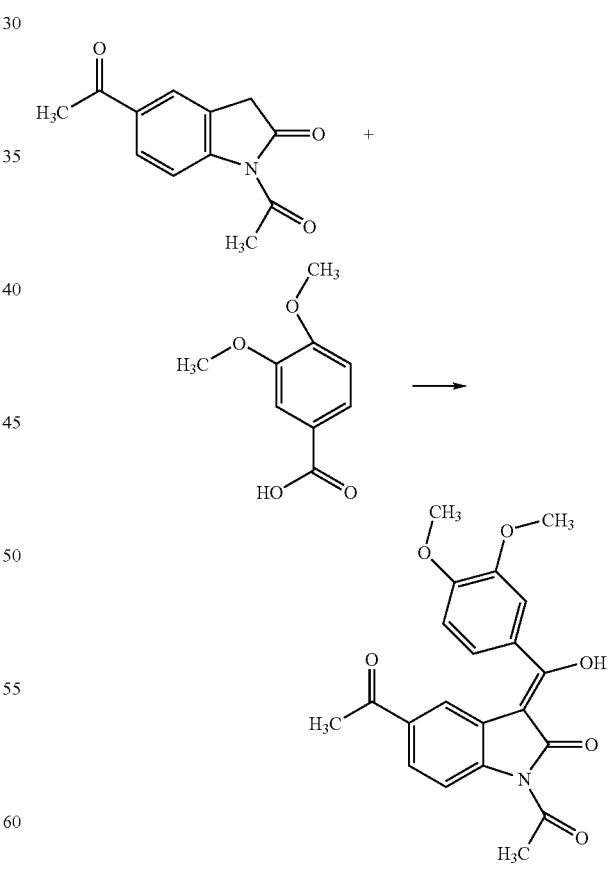

4.3 g (20 mmol) 1,5-diacetyl-2-indolinone (Ex. II) are stirred overnight together with 4 g 3,4-dimethoxybenzoic acid, 7.1 g TBTU (O-benzotriazol-1-yl-N,N,N',N'-tetramethyluronium tetrafluoroborate) and 14 ml triethylamine in 80 ml DMF (dimethylformamide) at ambient temperature. Then the mixture is poured onto 300 ml ice water with 10 ml of conc. hydrochloric acid and the precipitate formed is suction filtered. The residue is washed with a little methanol and then with ether.

Yield: 6.2 g (81.3% of theory)
$R_f$=0.85 (silica gel, methylene chloride/methanol 9:1)
$C_{21}H_{19}NO_6$ (MW=381.382)
Mass spectrum: m/z=381 (M)$^+$ The following compounds are prepared analogously to Example V:

(1) 1,5-diacetyl-3-[(benzo[1,3]dioxol-5-yl)-hydroxy-methylidene]-2-indolinone

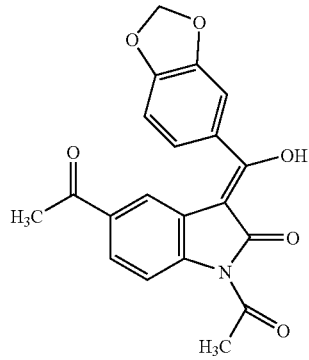

Prepared from 1,5-diacetyl-2-indolinone and piperonylic acid (benzo[1,3]dioxole-5-carboxylic acid)
Yield: 60% of theory
$R_f$=0.70 (silica gel, methylene chloride/methanol 9:1)
$C_{20}H_{15}NO_6$ (MW=365.339)
Mass spectrum: m/z=366 (M+H)$^+$ (2) 1,5-diacetyl-3-[(4-nitro-phenyl)-hydroxy-methylidene]-2-indolinone

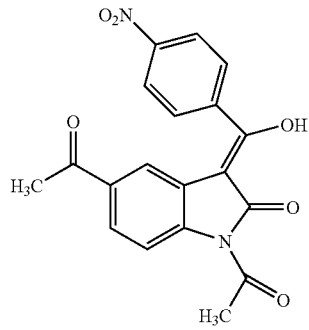

Prepared from 1,5-diacetyl-2-indolinone and 4-nitrobenzoic acid
Yield: 82% of theory
$R_f$=0.38 (silica gel, methylene chloride/methanol 9:1)
$C_{19}H_{14}N_2O_6$ (MW=366.328)
Mass spectrum: m/z=367 (M+H)$^+$ (3) 1,5-diacetyl-3-[(3-nitro-phenyl)-hydroxy-methylidene]-2-indolinone

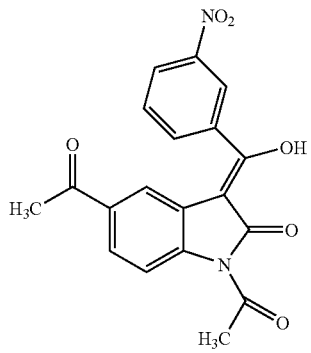

Prepared from 1,5-diacetyl-2-indolinone and 3-nitrobenzoic acid
Yield: 75% of theory
$R_f$=0.38 (silica gel, methylene chloride/methanol 9:1)
$C_{19}H_{14}N_2O_6$ (MW=366.328)
Mass spectrum: m/z=367 (M+H)$^+$ (4) 1,5-diacetyl-3-[(4-methyloxycarbonyl-phenyl)-hydroxy-methylidene]-2-indolinone

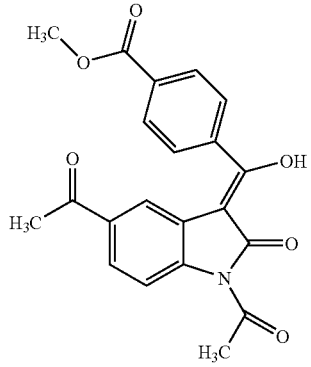

Prepared from 1,5-diacetyl-2-indolinone and monomethyl terephthalate
Yield: 71% of theory
$R_f$=0.41 (silica gel, methylene chloride/methanol 30:1)
$C_{21}H_{17}NO_6$ (MW=379.366)
Mass spectrum: m/z=380 (M+H)$^+$ (5) 1,5-diacetyl-3-[(4-chloro-phenyl)-hydroxy-methylidene]-2-indolinone

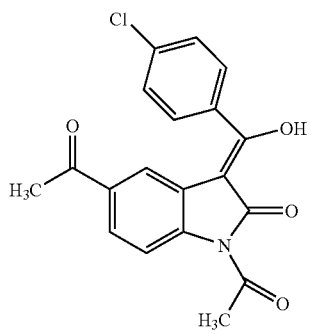

Prepared from 1,5-diacetyl-2-indolinone and 4-chlorobenzoic acid

Yield: 87% of theory $C_{19}H_{14}ClNO_4$ (MW=355.776)

Mass spectrum: m/z=356/358 (M+H)$^+$ (6) 1,5-diacetyl-3-[(3,4-dichloro-phenyl)-hydroxy-methylidene]-2-indolinone

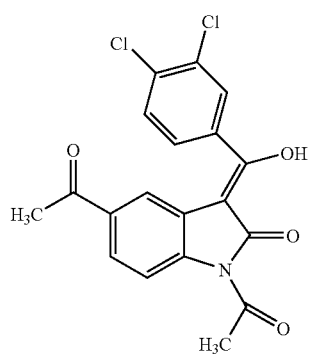

Prepared from 1,5-diacetyl-2-indolinone and 3,4-dichlorobenzoic acid

Yield: 83% of theory $C_{19}H_{13}Cl_2NO_4$ (MW=390.221)

Mass spectrum: m/z=390/392/394 (M+H)$^+$ (7) 1,5-diacetyl-3-[(4-cyano-phenyl)-hydroxy-methylidene]-2-indolinone

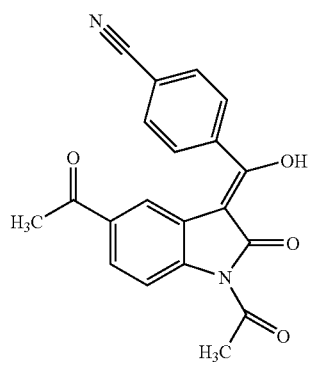

Prepared from 1,5-diacetyl-2-indolinone and 4-cyanobenzoic acid

Yield: 71% of theory $R_f$=0.32 (silica gel, methylene chloride/methanol 9:1)

$C_{20}H_{14}N_2O_4$ (MW=346.341)

Mass spectrum: m/z=347 (M+H)$^+$ (8) 1,5-diacetyl-3-[(4-trifluoromethyl-phenyl)-hydroxy-methylidene]-2-indolinone

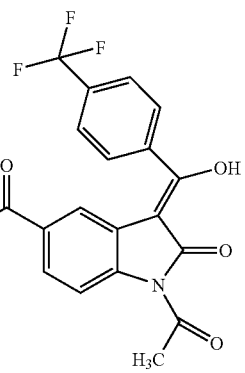

Prepared from 1,5-diacetyl-2-indolinone and 4-trifluoromethyl-benzoic acid

Yield: 83% of theory $C_{20}H_{14}F_3NO_4$ (MW=389.328)

Mass spectrum: m/z=390 (M+H)$^+$ (9) 1,5-diacetyl-3-[(2,3-dihydro-benzo-[1,4]dioxin-6-yl)-hydroxy-methylidene]-2-indolinone

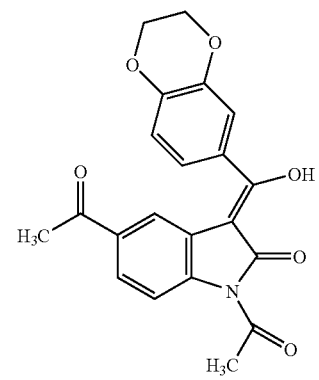

Prepared from 1,5-diacetyl-2-indolinone and 2,3-dihydro-1.4-benzodioxine-6-carboxylic acid Yield: 90% of theory $R_f$=0.75 (silica gel, methylene chloride/methanol 9:1)

$C_{21}H_{17}NO_6$ (MW=379.366)

Mass spectrum: m/z=380 (M+H)$^+$

(10) 1,5-diacetyl-3-[(3-methoxy-phenyl)-hydroxy-methylidene]-2-indolinone

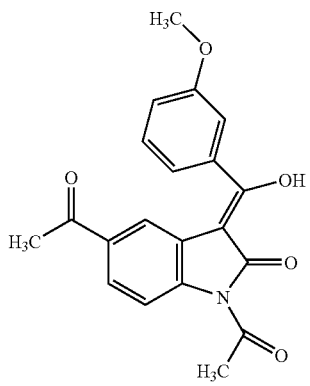

Prepared from 1,5-diacetyl-2-indolinone and 3-methoxy-benzoic acid
Yield: 70% of theory
$R_f$=0.67 (silica gel, methylene chloride/methanol 9:1)

(11) 1,5-diacetyl-3-[(4-methoxy-phenyl)-hydroxy-methylidene]-2-indolinone

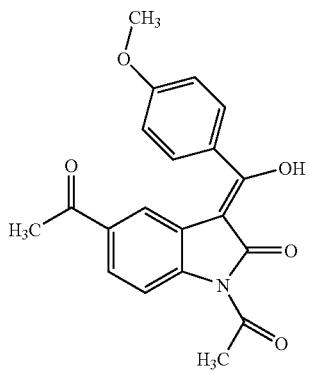

Prepared from 1,5-diacetyl-2-indolinone and 4-methoxy-benzoic acid
Yield: 59% of theory
$R_f$=0.39 (silica gel, methylene chloride/methanol 9:1)
$C_{20}H_{17}NO_5$ (MW=351.356)
Mass spectrum: m/z=350 (M−H)⁻

(12) 1-diacetyl-5-propionyl-3-[(benzo[1,3]dioxol-5-yl)-hydroxy-methylidene]-2-indolinone

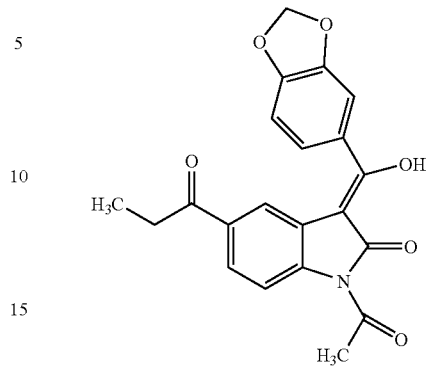

Prepared from 1-acetyl-5-propionyl-2-indolinone and piperonylic acid (benzo[1,3]-dioxole-5-carboxylic acid)
Yield: 67% of theory
$R_f$=0.49 (silica gel, methylene chloride/methanol 30:1)
$C_{21}H_{17}NO_6$ (MW=379.366)
Mass spectrum: m/z=380 (M+H)⁺

(13) 1,5-diacetyl-3-[(4-bromophenyl)-hydroxy-methylidene]-2-indolinone

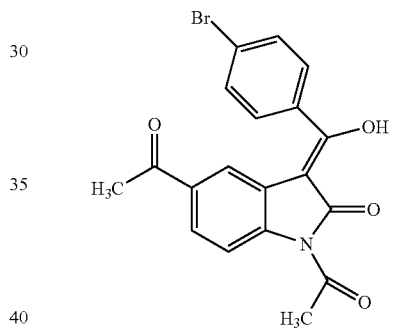

Prepared from 1,5-diacetyl-2-indolinone and 4-bromobenzoic acid
Yield: 89% of theory
$C_{19}H_{14}BrNO_4$ (MW=400.227)
Mass spectrum: m/z=400/402 (M+H)⁺

(14) 1,5-diacetyl-3-[(3,5-dichloro-phenyl)-hydroxy-methylidene]-2-indolinone

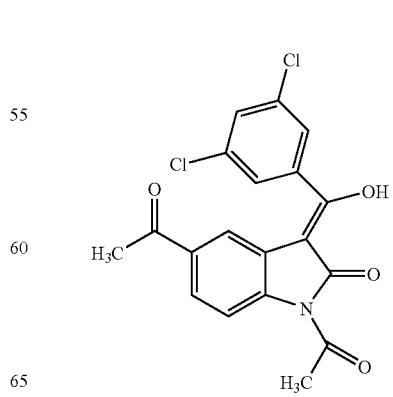

Prepared from 1,5-diacetyl-2-indolinone and 3,5-dichlorobenzoic acid
Yield: 79% of theory
$R_f$=0.26 (silica gel, methylene chloride/methanol 30:1)
$C_{19}H_{13}Cl_2NO_4$ (MW=390.221)
Mass spectrum: m/z=390/392/394 (M+H)$^+$

(15) 1,5-diacetyl-3-[(3,5-dimethoxyphenyl)-hydroxy-methylidene]-2-indolinone

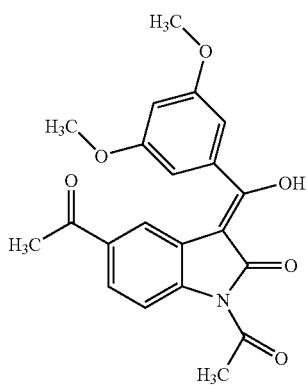

Prepared from 1,5-diacetyl-2-indolinone and 3,5-dimethoxybenzoic acid
Yield: 83% of theory
$R_f$=0.37 (silica gel, methylene chloride/methanol 30:1)
$C_{21}H_{19}NO_6$ (MW=381.382)
Mass spectrum: m/z=382 (M+H)$^+$

(16) 1,5-diacetyl-3-[(2-chloro-phenyl)-hydroxy-methylidene]-2-indolinone

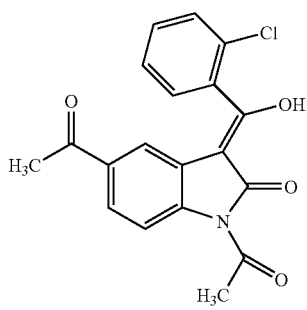

Prepared from 1,5-diacetyl-2-indolinone and 2-chlorobenzoic acid
Yield: 96% of theory
$C_{19}H_{14}ClNO_4$ (MW=355.776)
Mass spectrum: m/z=356/358 (M+H)$^+$

(17) 1,5-diacetyl-3-[(2-methoxy-phenyl)-hydroxy-methylidene]-2-indolinone

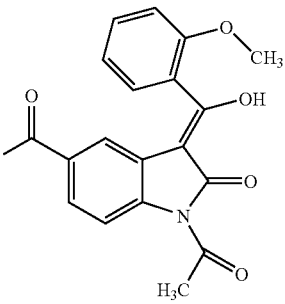

Prepared from 1,5-diacetyl-2-indolinone and 2-methoxybenzoic acid
Yield: 27% of theory
$C_{20}H_{17}NO_5$ (MW=351.356)
Mass spectrum: m/z=352 (M+H)$^+$

(18) 1,5-diacetyl-3-[(2,6-difluoro-phenyl)-hydroxy-methylidene]-2-indolinone

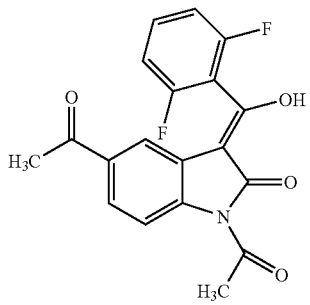

Prepared from 1,5-diacetyl-2-indolinone and 2,6-difluorobenzoic acid
Yield: 52% of theory
$C_{19}H_{13}F_2NO_4$ (MW=357.311)
Mass spectrum: m/z=358 (M+H)$^+$

(19) 1,5-diacetyl-3-[(4-fluorophenyl)-hydroxy-methylidene]-2-indolinone

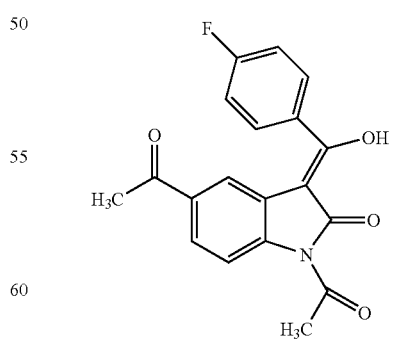

Prepared from 1,5-diacetyl-2-indolinone and 4-fluorobenzoic acid
Yield: 77% of theory $C_{19}H_{14}FNO_4$ (MW=339.321)
Mass spectrum: m/z=338 (M−H)$^-$

29

(20) 1,5-diacetyl-3-[(3,4-difluoro-phenyl)-hydroxy-methylidene]-2-indolinone

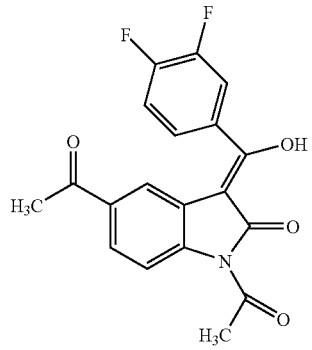

Prepared from 1,5-diacetyl-2-indolinone and 3,4-difluorobenzoic acid

Yield: 91% of theory

(21) 1,5-diacetyl-3-[(2,2-difluoro-benzo[1,3]dioxol-5-yl)-hydroxy-methylidene]-2-indolinone

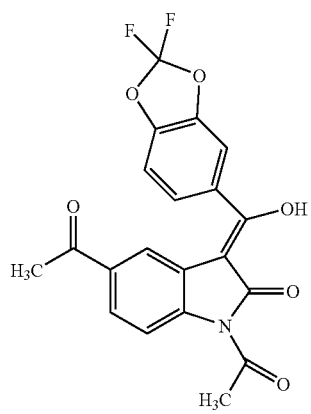

Prepared from 1,5-diacetyl-2-indolinone and 2,2-difluoro-benzo[1,3]dioxol-5-carboxylic acid Yield: 69% of theory $C_{20}H_{13}F_2NO_6$ (MW=401.32)

Mass spectrum: m/z=402 (M+H)$^+$

30

(22) 1,5-diacetyl-3-[(4-(2-methoxycarbonyl-ethyl)-phenyl)-hydroxy-methylidene]-2-indolinone

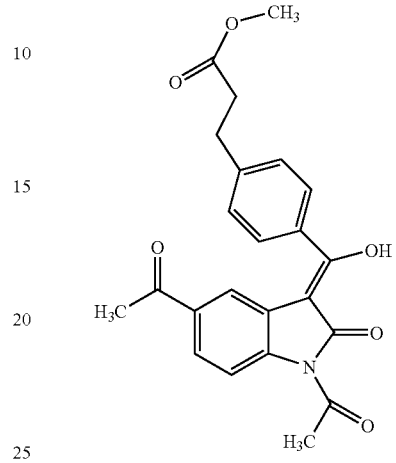

Prepared from 1,5-diacetyl-2-indolinone and 4-(2-methoxycarbonyl-ethyl)-benzoic acid Yield: 23% of theory $C_{23}H_{21}NO_6$ (MW=407.42)

Mass spectrum: m/z=408 (M+H)$^+$

(23) 1,5-diacetyl-3-[(pyrazin-2-yl)-hydroxy-methylidene]-2-indolinone

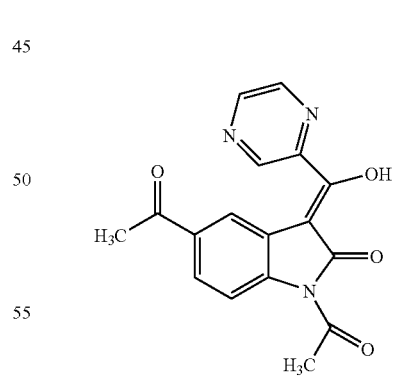

Prepared from 1,5-diacetyl-2-indolinone and pyrazine-2-carboxylic acid

Yield: 57% of theory $C_{17}H_{13}N_3O_4$ (MW=323.311)

Mass spectrum: m/z=324 (M+H)$^+$

(24) 1,5-diacetyl-3-[(pyridin-4-yl)-hydroxy-methylidene]-2-indolinone

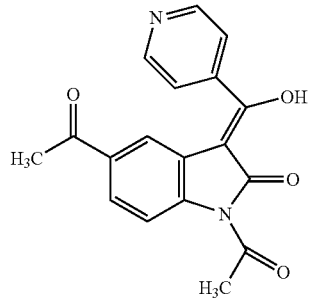

Prepared from 1,5-diacetyl-2-indolinone and isonicotinic acid (pyridine-4-carboxylic acid)

Yield: 87% of theory
$C_{18}H_{14}N_2O_4$ (MW=322.323)
Mass spectrum: m/z=323 (M+H)$^+$

(25) 1,5-diacetyl-3-[(furan-3-yl)-hydroxy-methylidene]-2-indolinone

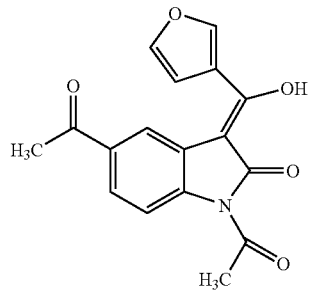

Prepared from 1,5-diacetyl-2-indolinone and furan-3-carboxylic acid

Yield: 73% of theory
$C_{17}H_{13}NO_5$ (MW=311.297)
Mass spectrum: m/z=312 (M+H)$^+$

(26) 1,5-diacetyl-3-[(4-diethylaminomethyl-phenyl)-hydroxy-methylidene]-2-indolinone

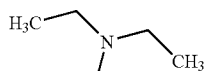
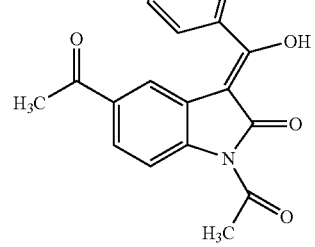

Prepared from 1,5-diacetyl-2-indolinone and 4-diethylaminomethyl-benzoic acid

Yield: 10% of theory
$C_{24}H_{26}N_2O_4$ (MW=406.486)
Mass spectrum: m/z=407 (M+H)$^+$

(27) 1,5-diacetyl-3-[(4-methoxycarbonylmethoxyphenyl)-hydroxy-methylidene]-2-indolinone

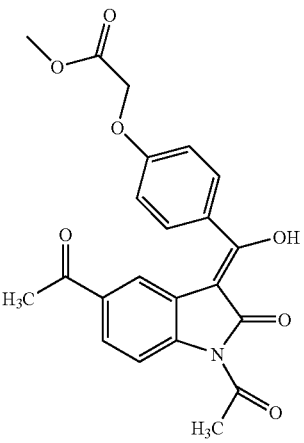

Prepared from 1,5-diacetyl-2-indolinone and 4-methoxycarbonyl-methoxy-benzoic acid Yield: 43% of theory
$C_{22}H_{19}NO_7$ (MW=409.39)
Mass spectrum: m/z=410 (M+H)$^+$

(28) 1,5-diacetyl-3-[(4-methylsulphonyl-phenyl)-hydroxy-methylidene]-2-indolinone

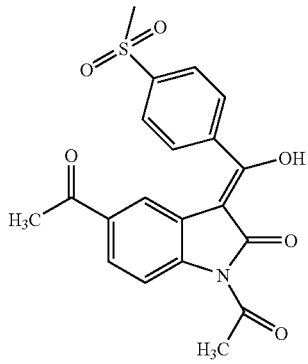

Prepared from 1,5-diacetyl-2-indolinone and 4-methylsulphonyl-benzoic acid
Yield: 25% of theory
$C_{20}H_{17}NO_6S$ (MW=399.418)
Mass spectrum: m/z=400 (M+H)$^+$

(29) 1,5-diacetyl-3-[(4-(2-diethylamino-ethoxy)-phenyl)-hydroxy-methylidene]-2-indolinone

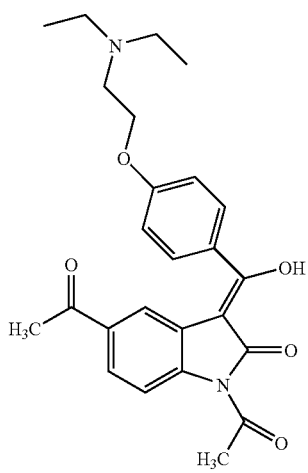

Prepared from 1,5-diacetyl-2-indolinone and 4-diethylamino-ethoxy-benzoic acid
Yield: 27% of theory
$C_{25}H_{28}N_2O_5$ (MW=436.500)
Mass spectrum: m/z=437 (M+H)$^+$

(30) 1,5-diacetyl-3-[(3-(2-diethylamino-ethoxy)-phenyl)-hydroxy-methylidene]-2-indolinone

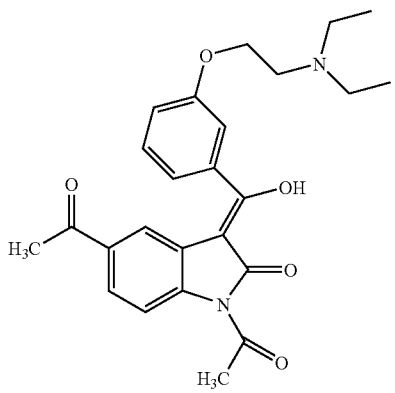

Prepared from 1,5-diacetyl-2-indolinone and 3-diethylamino-ethoxy-benzoic acid
Yield: 43% of theory
$C_{25}H_{28}N_2O_5$ (MW=436.500)
Mass spectrum: m/z=437 (M+H)$^+$

(31) 1,5-diacetyl-3-[(3-(2-diethylamino-ethoxy)-phenyl)-hydroxy-methylidene]-2-indolinone

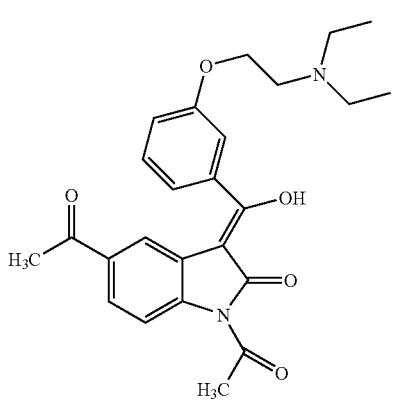

Prepared from 1,5-diacetyl-2-indolinone and 3-diethylamino-ethoxy-benzoic acid
Yield: 43% of theory
$C_{25}H_{28}N_2O_5$ (MW=436.500)
Mass spectrum: m/z=437 (M+H)$^+$

(31) 1,5-diacetyl-3-[(3-(2-diethylamino-ethoxy)-phenyl)-hydroxy-methylidene]-2-indolinone

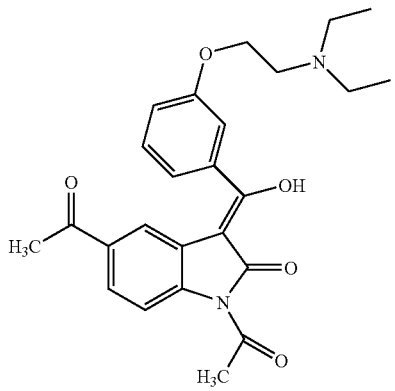

Prepared from 1,5-diacetyl-2-indolinone and 3-diethylamino-ethoxy-benzoic acid

Yield: 43% of theory $C_{25}H_{28}N_2O_5$ (MW=436.500)

Mass spectrum: m/z=437 (M+H)$^+$

(32) 1,5-diacetyl-3-(1-hydroxy-heptylidene)-2-indolinone

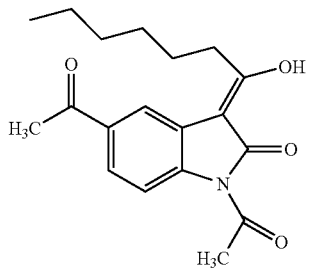

Prepared from 1,5-diacetyl-2-indolinone and heptanoic acid

(33) 1,5-diacetyl-3-(1-hydroxy-hexylidene)-2-indolinone

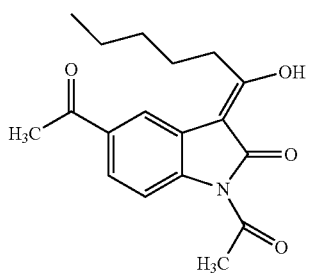

Prepared from 1,5-diacetyl-2-indolinone and hexanoic acid

(34) 1,5-diacetyl-3-(1-hydroxy-3-methyl-butylidene)-2-indolinone

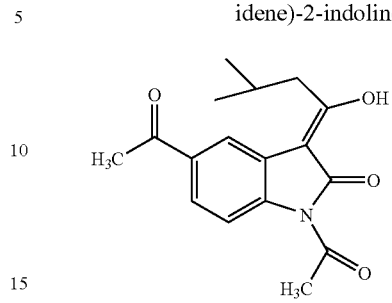

Prepared from 1,5-diacetyl-2-indolinone and isovaleric acid

EXAMPLE VI 1,5-diacetyl-3-[(3,4-dimethoxy-phenyl)-methoxy-methylidene]-2-indolinone

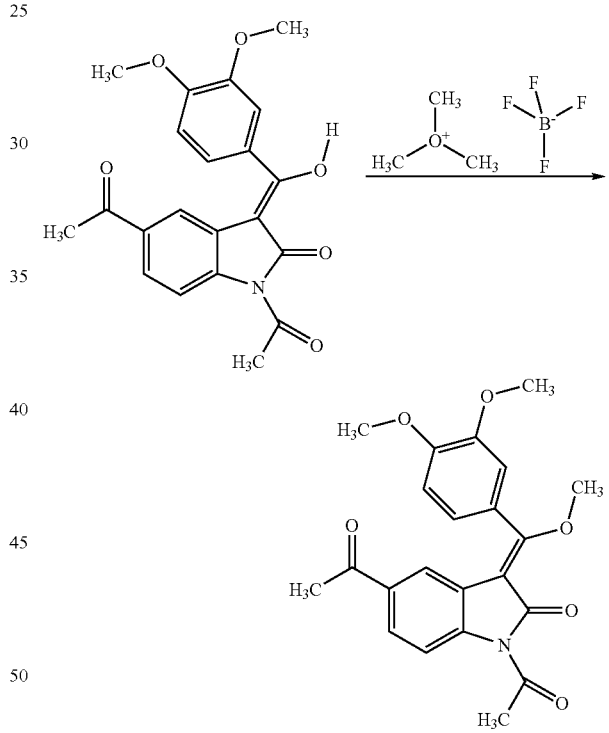

4.0 g (10.5 mmol) 1,5-diacetyl-3-[(3,4-dimethoxy-phenyl)-hydroxy-methylidene]-2-indolinone (Ex. V) are suspended in 100 ml methylene chloride and combined with 3.1 g (21 mmol) trimethyloxonium tetrafluoroborate and 7.2 ml Hünig base (ethyldiisopropylamine) at ambient temperature. The solution is stirred for 3 h, then another 1.55 g trimethyloxonium tetrafluoroborate and 3.5 ml Hünig base are added and the mixture is stirred overnight. After the same amount of reagent has been added again and the mixture has been stirred for a further 5 h, the reaction is washed three times with water, the organic phase is dried over sodium sulphate, filtered and concentrated by rotary evaporation. The residue is chromatographed through a silica gel column with methylene chloride/ methanol 9:1, the corresponding fractions are combined and concentrated by rotary evaporation.

Yield: 1.6 g (37% of theory)

$R_f$=0.78 (silica gel, methylene chloride/methanol 50:1)

$C_{22}H_{21}NO_6$ (MW=395.409)

Mass spectrum: m/z=396 (M+H)$^+$

The following compounds are prepared analogously to Example VI:

(1) 1,5-diacetyl-3-[(benzo[1,3]dioxol-5-yl)-methoxy-methylidene]-2-indolinone

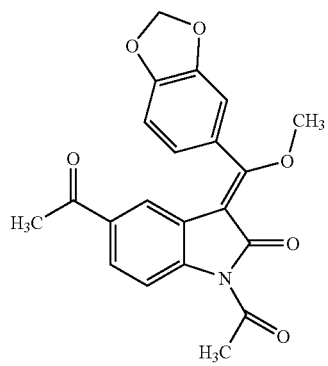

Prepared from 1,5-diacetyl-3-[(benzo[1,3]dioxol-5-yl)-hydroxy-methylidene]-2-indolinone (Ex. V.1)

Yield: 85% of theory $R_f$=0.55 (silica gel, methylene chloride/methanol 30:1)

$C_{21}H_{17}NO_6$ (MW=379.366)

Mass spectrum: m/z=380 (M+H)$^+$ (2) 1,5-diacetyl-3-[(4-nitro-phenyl)-methoxy-methylidene]-2-indolinone

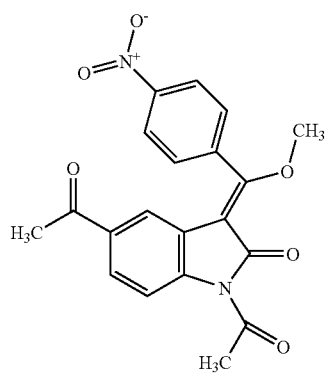

Prepared from 1,5-diacetyl-3-[(4-nitro-phenyl)-hydroxy-methylidene]-2-indolinone (Ex. V.2)

Yield: 82% of theory $R_f$=0.55 (silica gel, methylene chloride/methanol 30:1)

$C_{20}H_{16}N_2O_6$ (MW=380.354)

Mass spectrum: m/z=381 (M+H)$^+$ (3) 1,5-diacetyl-3-[(3-nitro-phenyl)-methoxy-methylidene]-2-indolinone

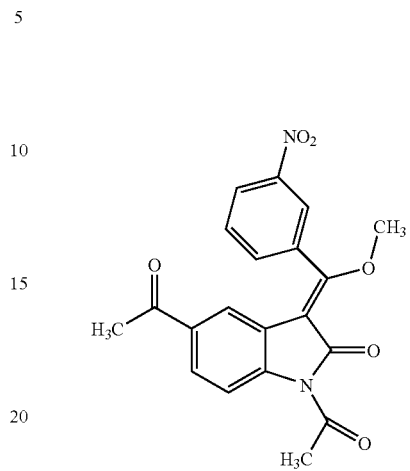

Prepared from 1,5-diacetyl-3-[(3-nitro-phenyl)-hydroxy-methylidene]-2-indolinone (Ex. V.3)

Yield: 43% of theory $R_f$=0.44 (silica gel, methylene chloride/methanol 9:1)

$C_{20}H_{16}N_2O_6$ (MW=380.354)

Mass spectrum: m/z=381 (M+H)$^+$ (4) 1,5-diacetyl-3-[(4-methyloxycarbonyl-phenyl)-methoxy-methylidene]-2-indolinone

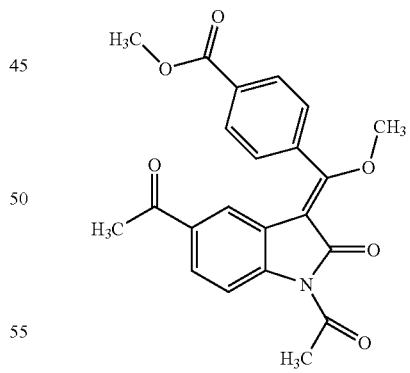

Prepared from 1,5-diacetyl-3-[(4-methyloxycarbonyl-phenyl)-hydroxy-methylidene]-2-indolinone (Ex. V.4)

Yield: 52% of theory $R_f$=0.56 (silica gel, methylene chloride/methanol 30:1)

$C_{22}H_{19}NO_6$ (MW=393.393)

Mass spectrum: m/z=394 (M+H)$^+$

(5) 1,5-diacetyl-3-[(4-chloro-phenyl)-methoxy-methylidene]-2-indolinone

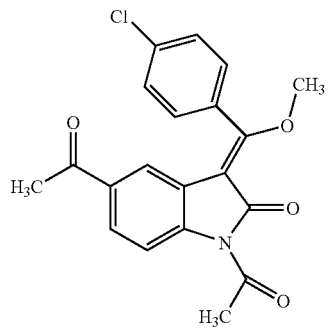

Prepared from 1,5-diacetyl-3-[(4-chloro-phenyl)-hydroxy-methylidene]-2-indolinone (Ex. V.5)
Yield: 65% of theory
$C_{20}H_{16}ClNO_4$ (MW=369.802)
Mass spectrum: m/z=370/372 (M+H)$^+$

(6) 1,5-diacetyl-3-[(3,4-dichloro-phenyl)-methoxy-methylidene]-2-indolinone

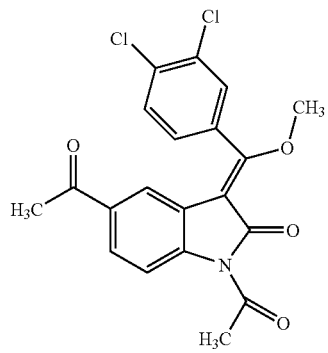

Prepared from 1,5-diacetyl-3-[(3,4-dichloro-phenyl)-hydroxy-methylidene]-2-indolinone (Ex. V.6)
Yield: 72% of theory
$C_{20}H_{15}Cl_2NO_4$ (MW=404.247)
Mass spectrum: m/z=404/406/408 (M+H)$^+$

(7) 1,5-diacetyl-3-[(4-cyano-phenyl)-methoxy-methylidene]-2-indolinone

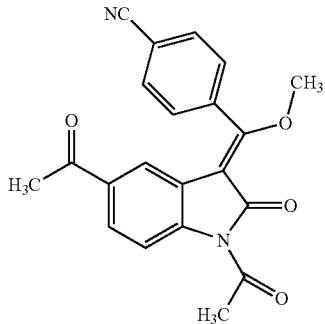

Prepared from 1,5-diacetyl-3-[(4-cyano-phenyl)-hydroxy-methylidene]-2-indolinone (Ex. V.7)
Yield: 53% of theory
$C_{21}H_{16}N_2O_4$ (MW=360.367)
Mass spectrum: m/z=361 (M+H)$^+$

(8) 1,5-diacetyl-3-[(4-trifluoromethyl-phenyl)-methoxy-methylidene]-2-indolinone

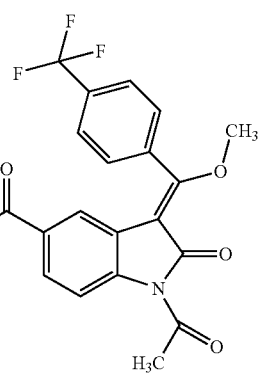

Prepared from 1,5-diacetyl-3-[(4-trifluoromethyl-phenyl)-hydroxy-methylidene]-2-indolinone (Ex. V.8)
Yield: 37% of theory
$C_{21}H_{16}F_3NO_4$ (MW=403.354)
Mass spectrum: m/z=404 (M+H)$^+$

(9) 1,5-diacetyl-3-[(2,3-dihydro-benzo-[1,4]dioxin-6-yl)-methoxy-methylidene]-2-indolinone

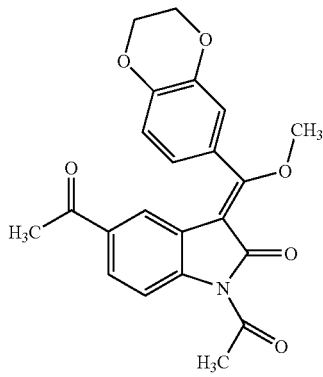

Prepared from 11,5-diacetyl-3-[(2,3-dihydro-benzo-[1,4]dioxin-6-yl)-hydroxy-methylidene]-2-indolinone (Ex. V.9)
Yield: 52% of theory
$R_f$=0.82 (silica gel, methylene chloride/methanol 9:1)
$C_{22}H_{19}NO_6$ (MW=393.393)
Mass spectrum: m/z=394 (M+H)$^+$

(10) 1,5-diacetyl-3-[(3-methoxy-phenyl)-methoxy-methylidene]-2-indolinone

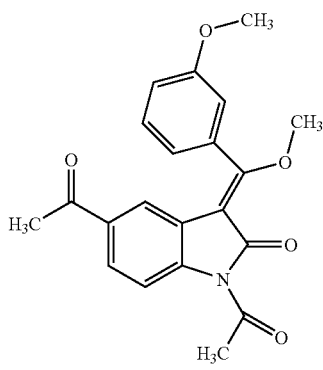

Prepared from 1,5-diacetyl-3-[(3-methoxy-phenyl)-hydroxy-methylidene]-2-indolinone (Ex. V.10)
Yield: 48% of theory
$R_f$=0.40 (silica gel, methylene chloride/methanol 9:1)
$C_{21}H_{19}NO_5$ (MW=365.383)
Mass spectrum: m/z=366 (M+H)$^+$

(11) 1,5-diacetyl-3-[(4-methoxy-phenyl)-methoxy-methylidene]-2-indolinone

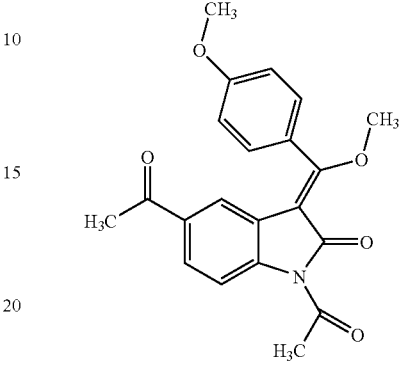

Prepared from 1,5-diacetyl-3-[(4-methoxy-phenyl)-hydroxy-methylidene]-2-indolinone (Ex. V.11)
Yield: 85% of theory
$R_f$=0.35 (silica gel, methylene chloride/methanol 30:1)
$C_{21}H_{19}NO_5$ (MW=365.383)
Mass spectrum: m/z=366 (M+H)$^+$

(12) 1-diacetyl-5-propionyl-3-[(benzo[1,3]dioxol-5-yl)-methoxy-methylidene]-2-indolinone

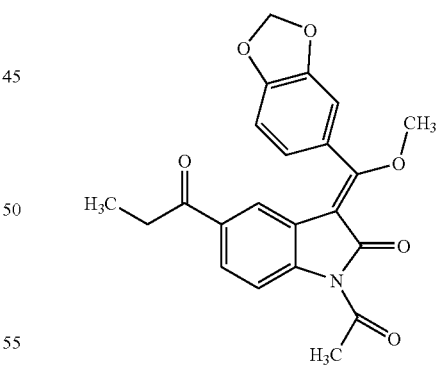

Prepared from 1-diacetyl-5-propionyl-3-[(benzo[1,3]dioxol-5-yl)-hydroxy-methylidene]-2-indolinone (Ex. V.12)
Yield: 98% of theory
$R_f$=0.63 (silica gel, methylene chloride/methanol 30:1)
$C_{22}H_{19}NO_6$ (MW=393.393)
Mass spectrum: m/z=394 (M+H)$^+$

(13) 1,5-diacetyl-3-[(4-bromophenyl)-methoxy-methylidene]-2-indolinone

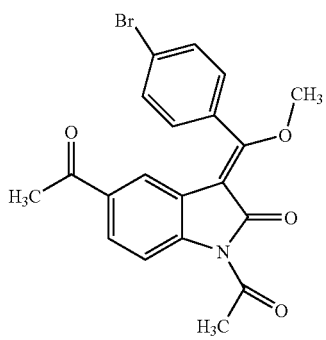

Prepared from 1,5-diacetyl-3-[(4-bromophenyl)-hydroxy-methylidene]-2-indolinone (Ex. V.13)
Yield: 48% of theory

(14) 1,5-diacetyl-3-[(3,5-dichloro-phenyl)-methoxy-methylidene]-2-indolinone

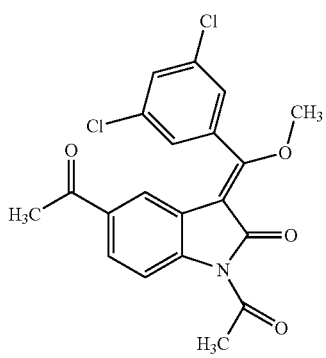

Prepared from 1,5-diacetyl-3-[(3,5-dichloro-phenyl)-hydroxy-methylidene]-2-indolinone (Ex. V.14)
Yield: 44% of theory
$R_f$=0.86 (silica gel, methylene chloride/methanol 30:1)
$C_{19}H_{13}Cl_2NO_4$ (MW=390.221)
Mass spectrum: m/z=388/390/392 (Cl2, M+H)$^+$

(15) 1,5-diacetyl-3-[(3,5-dimethoxy-phenyl)-methoxy-methylidene]-2-indolinone

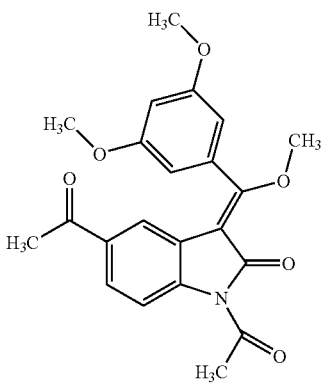

Prepared from 1,5-diacetyl-3-[(3,5-dimethoxy-phenyl)-hydroxy-methylidene]-2-indolinone (Ex. V.15)
Yield: 74% of theory
$R_f$=0.65 (silica gel, methylene chloride/methanol 30:1)
$C_{22}H_{21}NO_6$ (MW=395.409)
Mass spectrum: m/z=396 (M+H)$^+$

(16) 1,5-diacetyl-3-[(2-chloro-phenyl)-methoxy-methylidene]-2-indolinone

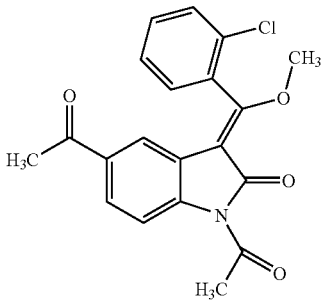

Prepared from 1,5-diacetyl-3-[(2-chloro-phenyl)-hydroxy-methylidene]-2-indolinone (Ex. V.16)
Yield: 54% of theory
$C_{20}H_{16}ClNO_4$ (MW=369.802)
Mass spectrum: m/z=370/372 (M+H)$^+$

(17) 1,5-diacetyl-3-[(2-methoxy-phenyl)-methoxy-methylidene]-2-indolinone

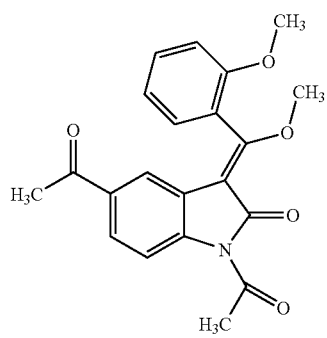

Prepared from 1,5-diacetyl-3-[(2-methoxy-phenyl)-hydroxy-methylidene]-2-indolinone (Ex. V.17)
Yield: 56% of theory
$C_{21}H_{19}NO_5$ (MW=365.383)
Mass spectrum: m/z=366 (M+H)$^+$

(18) 1,5-diacetyl-3-[(2,6-difluoro-phenyl)-methoxy-methylidene]-2-indolinone

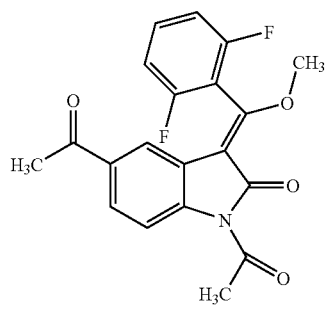

Prepared from 1,5-diacetyl-3-[(2,6-difluoro-phenyl)-hydroxy-methylidene]-2-indolinone (Ex. V.18)
Yield: 59% of theory
$C_{20}H_{15}F_2NO_4$ (MW=3371.337)
Mass spectrum: m/z=372 (M+H)$^+$

(19) 1,5-diacetyl-3-[(4-fluorophenyl)-methoxy-methylidene]-2-indolinone

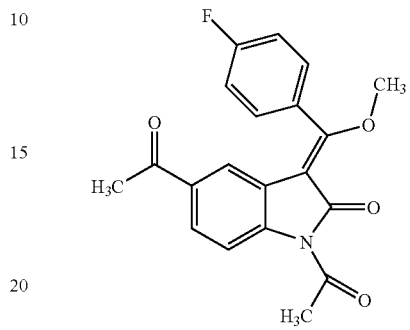

Prepared from 1,5-diacetyl-3-[(4-fluorophenyl)-hydroxy-methylidene]-2-indolinone (Ex. V.19)
Yield: 88% of theory
$C_{20}H_{16}FNO_4$ (MW=353.347)
Mass spectrum: m/z=354 (M+H)$^+$

(20) 1,5-diacetyl-3-[(3,4-difluoro-phenyl)-methoxy-methylidene]-2-indolinone

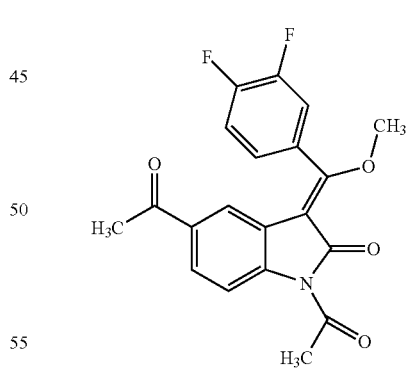

Prepared from 1,5-diacetyl-3-[(3,4-difluoro-phenyl)-hydroxy-methylidene]-2-indolinone (Ex. V.20)
Yield: 23% of theory
$C_{20}H_{15}F_2NO_4$ (MW=371.334)
Mass spectrum: m/z=372 (M+H)$^+$

(21) 1,5-diacetyl-3-[(2,2-difluoro-benzo[1,3]dioxol-5-yl)-methoxy-methylidene]-2-indolinone

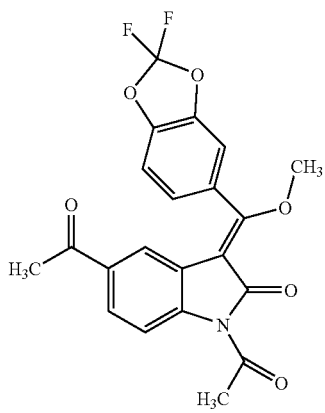

Prepared from 1,5-diacetyl-3-[(2,2-difluoro-benzo[1,3]dioxol-5-yl)-hydroxy-methylidene]-2-indolinone (Ex. V.21)
Yield: 6% of theory
$C_{21}H_{15}F_2NO_6$ (MW=415.346)
Mass spectrum: m/z=416 (M+H)$^+$

(22) 1,5-diacetyl-3-[(4-(2-methoxycarbonyl-ethyl)-phenyl)-methoxy-methylidene]-2-indolinone

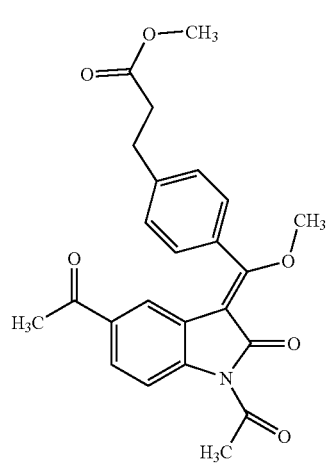

Prepared from 1,5-diacetyl-3-[(4-(2-methoxycarbonyl-ethyl)-phenyl)-hydroxy-methylidene]-2-indolinone (Ex. V.22)
Yield: 63% of theory
$C_{24}H_{23}NO_6$ (MW=421.447)
Mass spectrum: m/z=422 (M+H)$^+$

(23) 1,5-diacetyl-3-[furan-3-yl-methoxy-methylidene]-2-indolinone

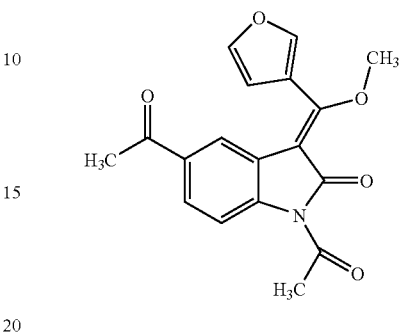

Prepared from 1,5-diacetyl-3-[furan-3-yl-hydroxy-methylidene]-2-indolinone (Ex. V.25)
Yield: 59% of theory
$C_{18}H_{15}NO_5$ (MW=325.324)

Mass spectrum: m/z=326 (M+H)$^+$

(24) 1,5-diacetyl-3-[(4-methoxycarbonylmethoxy-phenyl)-methoxy-methylidene]-2-indolinon

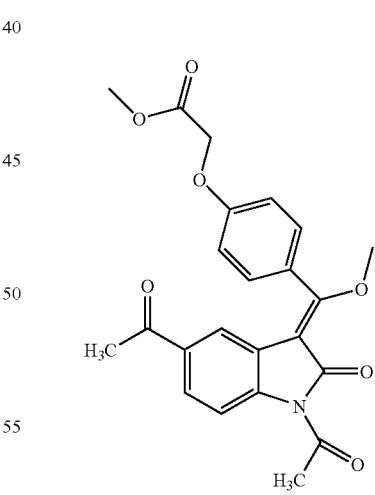

Prepared from 1,5-diacetyl-3-[(4-methoxycarbonylmethoxy-phenyl)-hydroxy-methylidene]-2-indolinone
Yield: 24% of theory
$C_{23}H_{21}NO_7$ (MW=423.415)
Mass spectrum: m/z=424 (M+H)$^+$

(25) 1,5-diacetyl-3-[(4-methylsulphonyl-phenyl)-methoxy-methylidene]-2-indolinone

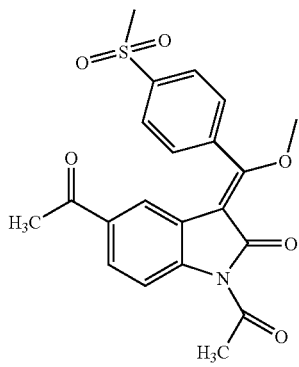

Prepared from 1,5-diacetyl-3-[(4-methylsulphonyl-phenyl)-hydroxy-methylidene]-2-indolinone (Ex. V.28)
Yield: 20% of theory
$C_{21}H_{19}NO_6S$ (MW=413.445)
Mass spectrum: m/z=414 (M+H)$^+$

(26) 1,5-diacetyl-3-(1-methoxy-octylidene)-2-indolinone

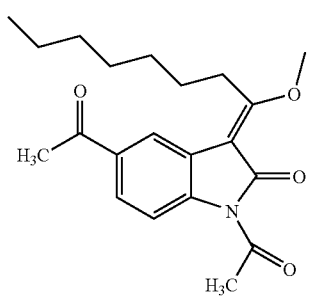

Prepared from 1,5-diacetyl-3-(1-hydroxyl-octylidene)-2-indolinone (Ex. VIII)
Yield: 82% of theory
$C_{21}H_{27}NO_4S$ (MW=357.443)
Mass spectrum: m/z=358 (M+H)$^+$

(27) 1,5-diacetyl-3-(1-methoxy-heptylidene)-2-indolinone

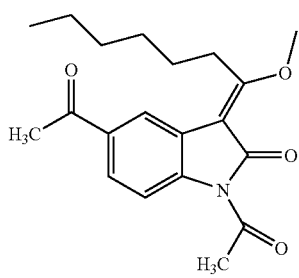

Prepared from 1,5-diacetyl-3-(1-hydroxy-heptylidene)-2-indolinone (Ex. V.32)

(28) 1,5-diacetyl-3-(1-methoxy-hexylidene)-2-indolinone

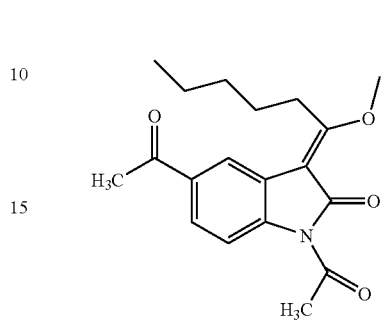

Prepared from 1,5-diacetyl-3-(1-hydroxy-hexylidene)-2-indolinone (Ex. V.33)

(29) 1,5-diacetyl-3-(1-methoxy-3-methyl-butylidene)-2-indolinone

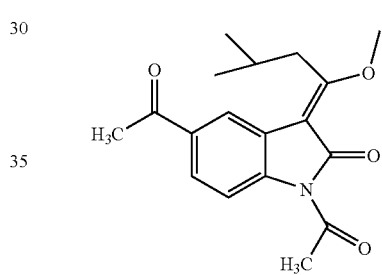

Prepared from 1,5-diacetyl-3-(1-hydroxy-3-methyl-butylidene)-2-indolinone (Ex. V.34)

EXAMPLE VII 1,5-diacetyl-3-[chloro-(Pyrazin-2-yl)-methylidene]-2-indolinone

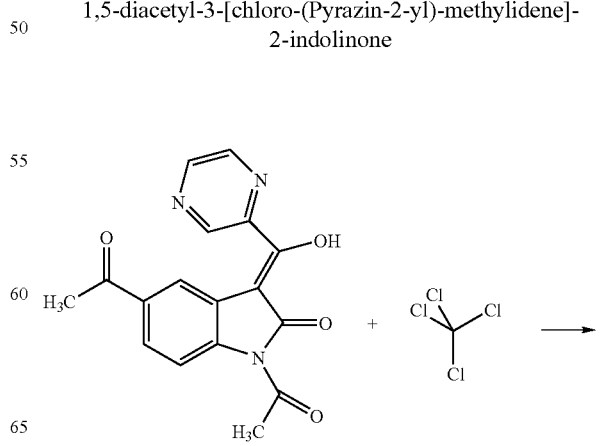

-continued

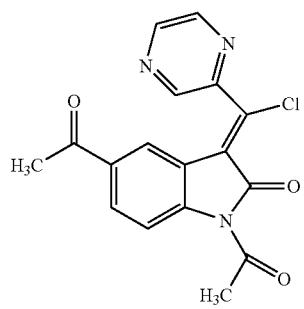

1.2 g (3.7 mmol) 1,5-diacetyl-3-[(pyrazin-2-yl)-hydroxy-methylidene]-2-indolinone (Ex. V.23) are dissolved in 50 ml dioxane and refluxed with 2 ml carbon tetrachloride and 2 g triphenylphosphine for 5 h. Then the mixture is left to cool and evaporated down. The residue is chromatographed through a silica gel column with methylene chloride/methanol 25:1, the corresponding fractions are combined and concentrated by rotary evaporation.

Yield: 400 mg (40% of theory)
$R_f$=0.70 (silica gel, methylene chloride/methanol 30:1)
$C_{17}H_{12}ClN_3O_3$ (MW=341.756)
Mass spectrum: m/z=342/344 (M+H)$^+$ (CL)

The following compound is prepared analogously to Example VII:

(1) 1,5-diacetyl-3-[chloro-(4-(2-dimethylamino-ethoxy)-phenyl)-methylidene]-2-indolinone

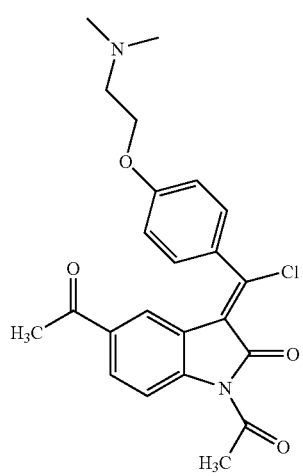

EXAMPLE VIII 1,5-diacetyl-3-(1-hydroxy-octylidene)-2-indolinone

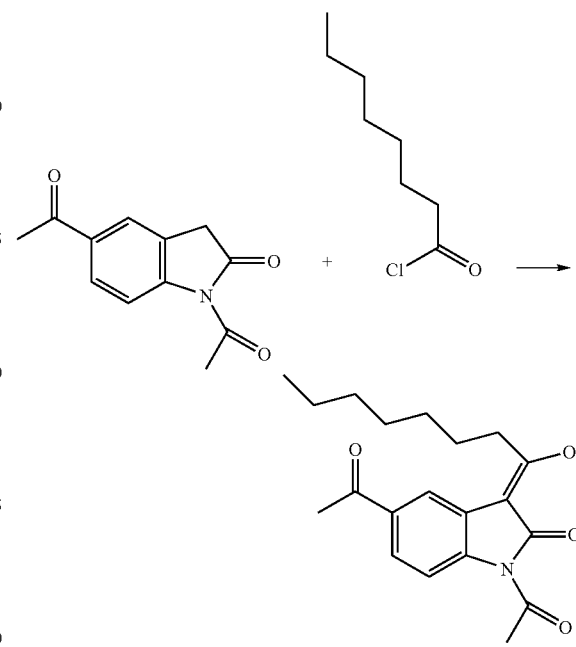

4.3 g (20 mmol) 1,5-diacetyl-2-indolinone (Ex. II) are dissolved in 20 ml of dimethylformamide and 490 mg dimethylaminopyridine (DMAP) and 6 ml triethylamine added and the mixture is cooled in the ice bath. 3.8 ml (22 mmol) octanoic acid chloride in 20 ml of dimethylformamide are added to this solution and the mixture is stirred for a further 10 min. Then the reaction mixture is added to 150 ml of methylene chloride and 150 ml 1 N hydrochloric acid. The organic phase is separated off, dried over sodium sulphate and concentrated by rotary evaporation. The residue is chromatographed through a silica gel column with methylene chloride/methanol 95:5.

Yield: 740 mg (11% of theory)
$C_{20}H_{25}NO_4$ (MW=343.417)
Mass spectrum: m/z=344 (M)+
Preparation of the End Compounds:
Eluant:
A: methylene chloride/methanol 9:1
B: methylene chloride/methanol 4:1
C: methylene chloride/methanol/conc. ammonia 9:1:0.1
D: methylene chloride/methanol 30:1
E: methylene chloride/methanol/triethylamine 9:1:0.1

In the formulae in the Table the bond drawn free always represents the bond of the relevant group at the point of attachment in the molecule. The entry "—CH$_3$" in the Table thus denotes a methyl group and the entry

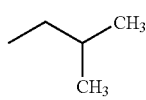

denotes an isobutyl group, i.e.—CH$_2$—CH(CH$_3$)$_2$.

EXAMPLE 1

5-acetyl-3-[(3-dimethylamino-propylamino)-phenyl-methylidene]-2-indolinone

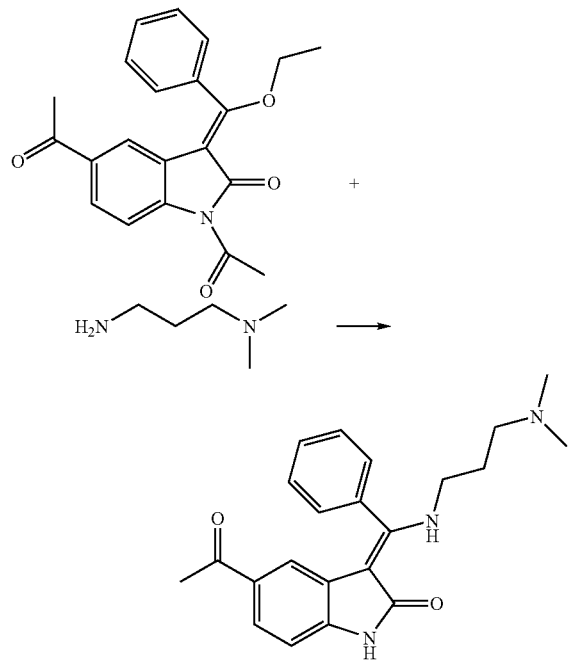

0.2 g (0.57 mmol) of 1,5-diacetyl-3-(phenyl-ethoxy-methylidene)-2-indolinone (Ex. III) are suspended in 5 ml of dimethylformamide and stirred with 0.07 ml 3-dimethyl-amino-propylamine at 70° C. for 12 h. Then the mixture is left to cool, 2 ml of methanol and 1 ml 1 N sodium hydroxide solution are added and the mixture is stirred at ambient temperature for 30 min. Then water is added, and the resulting precipitate is filtered off, washed and dried. If necessary, the compound may be purified by chromatography on silica gel. A suitable eluant is methylene chloride/methanol 30:1.

Yield: 0.1 g (82% of theory)

$R_f$=0.39 (silica gel, methylene chloride/methanol/conc. ammonia 9:1:0.1)

$C_{22}H_{25}N_3O_2$ (MW=363.458)

Mass spectrum: m/z=364 (M+H)$^+$

The following compounds of formula I are prepared analogously to Example 1:

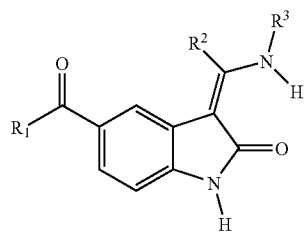

| Example | R$^1$ | R$^2$ | R$^3$ | Educt Yield [%] | Mass spectrum (ES) m/z | R$_f$ value (silica gel) (eluant) |
|---|---|---|---|---|---|---|
| 1.001 | Me | Ph | ‑CH$_2$CH$_2$CH$_2$‑N(CH$_3$)CH$_3$ | III 85.9 | (M+H)$^+$ = 350 | 0.43 (A) |
| 1.002 | Me | Ph | ‑CH$_2$CH$_2$CH$_2$‑morpholino | III 74.1 | (M+H)$^+$ = 391 | 0.51 (A) |
| 1.003 | Me | Ph | ‑CH$_2$CH$_2$‑N(iPr)$_2$ | III 88.8 | (M+H)$^+$ = 406 | 0.58 (A) |

-continued
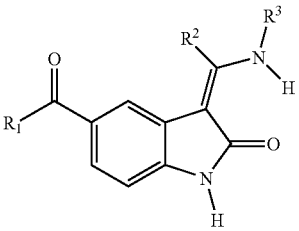
| Example | R¹ | R² | R³ | Educt Yield [%] | Mass spectrum (ES) m/z | R$_f$ value (silica gel) (eluant) |
|---|---|---|---|---|---|---|
| 1.004 | Me | Ph | 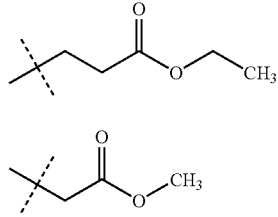 | III 81.9 | (M+H)⁺ = 379 | 0.23 (D) |
| 1.005 | Me | Ph | 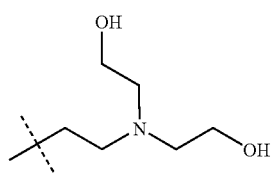 | III 88.5 | (M+H)⁺ = 351 | 0.22 (D) |
| 1.006 | Me | Ph | 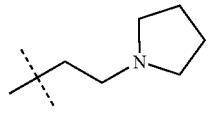 | III 80.6 | (M+H)⁺ = 410 | 0.35 (C) |
| 1.007 | Me | Ph | 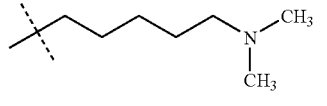 | III 79.0 | (M+H)⁺ = 376 | 0.39 (C) |
| 1.008 | Me | Ph | 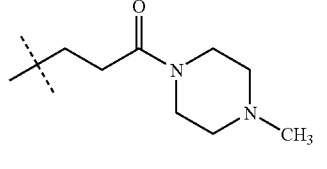 | III 66.4 | (M+H)⁺ = 392 | 0.27 (C) |
| 1.009 | Me | Ph | 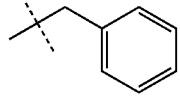 | III 64.9 | (M+H)⁺ = 433 | 0.52 (C) |
| 1.010 | Me | Ph | 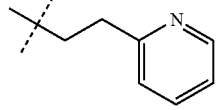 | III 80.7 | (M−H)⁻ = 367 | 0.42 (A) |
| 1.011 | Me | Ph | 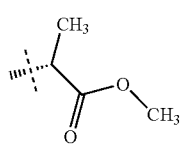 | III 54.7 | (M−H)⁻ = 382 | 0.39 (A) |
| 1.012 | Me | Ph |  | III 67.1 | (M+H)⁺ = 365 | 0.48 (A) |

-continued

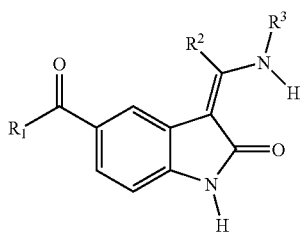

| Example | R¹ | R² | R³ | Educt Yield [%] | Mass spectrum (ES) m/z | R_f value (silica gel) (eluant) |
|---|---|---|---|---|---|---|
| 1.013 | Me | Ph | –CH₂–C₆H₄–CH₂–NH–C(O)–O–C(CH₃)₃ | III 32.8 | (M+H)⁺ = 498 | 0.59 (A) |
| 1.014 | Me | Ph | –(CH₂)₃–C(O)–O–CH₃ | III 92.3 | (M+H)⁺ = 379 | 0.34 (A) |
| 1.015 | Me | Ph | –(CH₂)₂–C₆H₅ | III 73.1 | (M+H)⁺ = 383 | 0.33 (A) |
| 1.016 | Me | Ph | –(CH₂)₂–NH–C(O)–CH₃ | III 57.7 | (M+H)⁺ = 364 | 0.29 (A) |
| 1.017 | Me | Ph | –(CH₂)₂–NH–(2-pyridyl-5-NO₂) | III 22.9 | (M+H)⁺ = 444 | 0.42 (A) |
| 1.018 | Me | 3,4-methylenedioxyphenyl | –(CH₂)₅–N(CH₃)₂ | VI.1 53.2 | (M+H)⁺ = 436 | 0.46 (B) |
| 1.019 | Me | 3,4-methylenedioxyphenyl | –(CH₂)₂–NH–C(O)–CH₃ | VI.1 65.2 | (M+H)⁺ = 408 | 0.43 (A) |
| 1.020 | Me | Ph | –(CH₂)₆–C(O)–O–C(CH₃)₃ | III 11.7 | (M+H)⁺ = 463 | 0.56 (A) |

-continued
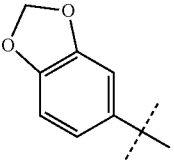
| Example | R¹ | R² | R³ | Educt Yield [%] | Mass spectrum (ES) m/z | $R_f$ value (silica gel) (eluant) |
|---|---|---|---|---|---|---|
| 1.021 | Me | 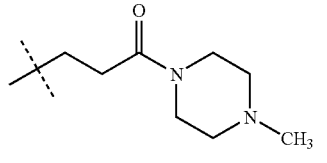 | 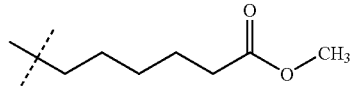 | VI.1 28.7 | (M+H)⁺ = 477 | 0.31 (A) |
| 1.022 | Me | Ph | 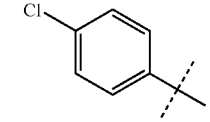 | III 66.6 | (M+H)⁺ = 407 | 0.38 (A) |
| 1.023 | Me | 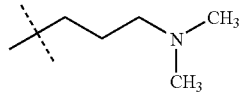 | 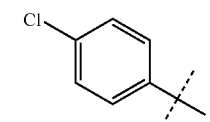 | VI.5 70.2 | (M+H)⁺ = 398/400 (Cl) | 0.18 (A) |
| 1.024 | Me | 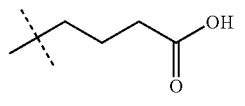 | 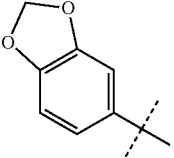 | VI.5 57.0 | (M+H)⁺ = 399/401 (Cl) | 0.25 (A) |
| 1.025 | Me | 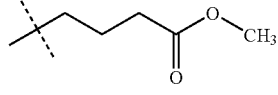 | 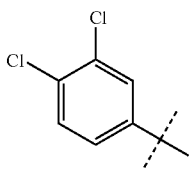 | VI.1 44.9 | (M+H)⁺ = 423 | 0.32 (A) |
| 1.026 | Me | 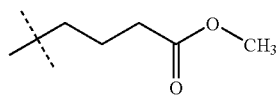 | 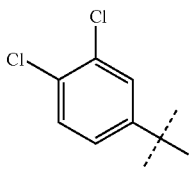 | VI.6 51.9 | (M+H)⁺ = 447/449/ 451 (Cl2) | 0.30 (A) |
| 1.027 | Me | 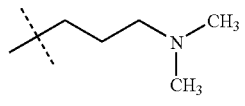 | 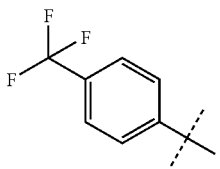 | IV.6 24.5 | (M+H)⁺ = 423/434/ 436 (Cl2) | 0.37 (C) |
| 1.028 | Me | 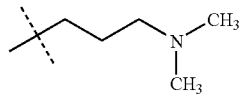 | 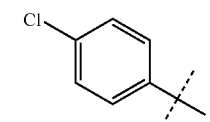 | VI.8 35.1 | (M+H)⁺ = 432 | 0.25 (A) |

-continued
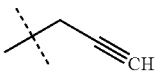
| Example | R¹ | R² | R³ | Educt Yield [%] | Mass spectrum (ES) m/z | $R_f$ value (silica gel) (eluant) |
|---|---|---|---|---|---|---|
| 1.029 | Me | Ph | Et | III 98 | (M+H)⁺ = 307 | 0.44 (A) |
| 1.030 | Me | Ph | 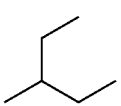 | III 90.6 | (M+H)⁺ = 317 | 0.31 (A) |
| 1.031 | Me | Ph | 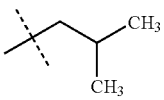 | III 90.3 | (M+H)⁺ = 349 | 0.48 (A) |
| 1.032 | Me | Ph | i-Pr | III 77.5 | (M+H)⁺ = 321 | 0.46 (A) |
| 1.033 | Me | Ph | 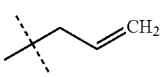 | III 78.4 | (M+H)⁺ = 335 | 0.33 (A) |
| 1.034 | Me | Ph | n-Pr | III 56.7 | (M+H)⁺ = 321 | 0.31 (A) |
| 1.035 | Me | Ph | 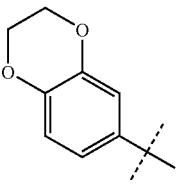 | III 93.3 | (M+H)⁺ = 319 | 0.32 (A) |
| 1.036 | Me | 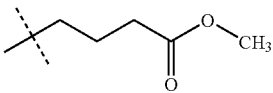 | 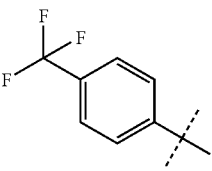 | VI.9 72.1 | (M+H)⁺ = 437 | 0.38 (A) |
| 1.037 | Me | 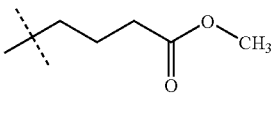 | 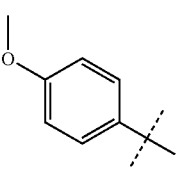 | VI.8 40.2 | (M+H)⁺ = 447 | 0.75 (A) |
| 1.038 | Me | 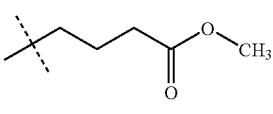 | 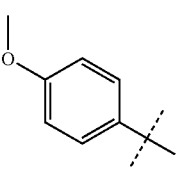 | VI.11 76.9 | (M+H)⁺ = 409 | 0.36 (A) |

-continued
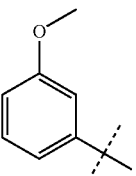
| Example | R¹ | R² | R³ | Educt Yield [%] | Mass spectrum (ES) m/z | $R_f$ value (silica gel) (eluant) |
|---|---|---|---|---|---|---|
| 1.039 | Me | 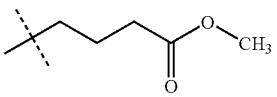 | 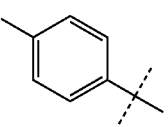 | VI.10 80.3 | (M+H)⁺ = 409 | 0.36 (A) |
| 1.040 | Me | 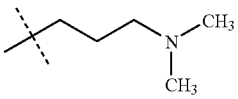 | 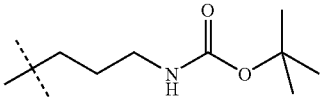 | VI.13 67.7 | (M−H)⁻ = 440/442 (Br) | 0.26 (A) |
| 1.041 | Me | Ph | 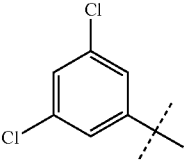 | III 85.0 | (M+H)⁺ = 436 | 0.28 (A) |
| 1.042 | Me | 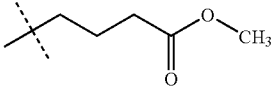 | 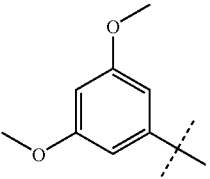 | VI.14 67.8 | (M−H)⁻ = 445/447/ 449 (Cl2) | 0.25 (A) |
| 1.043 | Me | 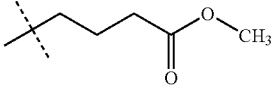 | 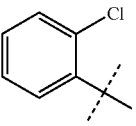 | VI.15 71.0 | (M+H)⁺ = 439 | 0.27 (A) |
| 1.044 | Me | 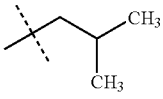 | 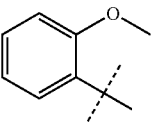 | VI.16 75.5 | (M+H)⁺ = 369/371 (Cl) | 0.33 (A) |
| 1.045 | Me | 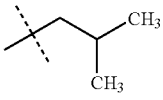 | 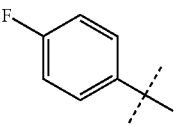 | VI.17 62.2 | (M+H)⁺ = 365 | 0.05 (CH₂Cl₂/ MeOH 50:1) |
| 1.046 | Me | 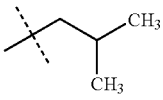 | | VI.19 68.1 | (M+H)⁺ = 353 | 0.46 (A) |

-continued
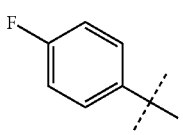
| Example | R¹ | R² | R³ | Educt Yield [%] | Mass spectrum (ES) m/z | $R_f$ value (silica gel) (eluant) |
|---|---|---|---|---|---|---|
| 1.047 | Me | 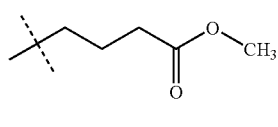 | 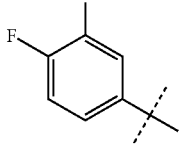 | VI.19 59.4 | $(M+H)^+$ = 397 | 0.45 (A) |
| 1.048 | Me | 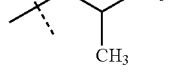 | 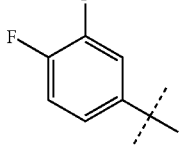 | VI.20 13.8 | $(M+H)^+$ = 371 | 0.54 (A) |
| 1.049 | Me | 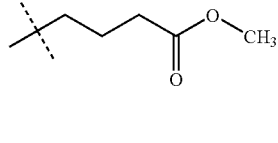 | 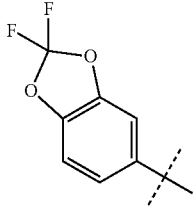 | VI.20 51.4 | $(M+H)^+$ = 415 | 0.56 (A) |
| 1.050 | Me | 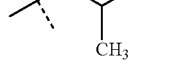 | 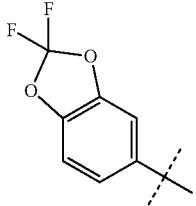 | VI.21 38.5 | $(M+H)^+$ = 415 | 0.31 (A) |
| 1.051 | Me | 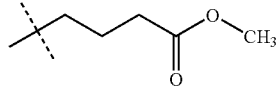 | 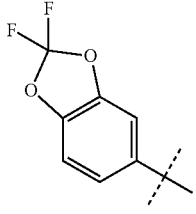 | VI.21 33.8 | $(M-H)^-$ = 457 | 0.46 (A) |
| 1.052 | Me | 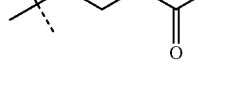 |  | VI.21 22.4 | $(M-H)^-$ = 443 | 0.37 (B) |

-continued

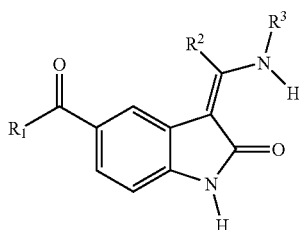

| Example | R¹ | R² | R³ | Educt Yield [%] | Mass spectrum (ES) m/z | R_f value (silica gel) (eluant) |
|---|---|---|---|---|---|---|
| 1.053 | Me | 4-cyanophenyl | -C(CH₃)₂-CH₂-CH₂-C(O)-O-CH₃ | VI.7 78.6 | (M+H)⁺ = 404 | 0.53 (A) |
| 1.054 | Me | 4-cyanophenyl | -C(CH₃)₂-CH₂-CH₂-N(CH₃)₂ | VI.7 90.3 | (M+H)⁺ = 389 | 0.53 (C) |
| 1.055 | Me | 4-cyanophenyl | -C(CH₃)₂-CH(CH₃)₂ | VI.7 83.8 | (M+H)⁺ = 360 | 0.36 (A) |
| 1.056 | Me | 4-cyanophenyl | n-Pr | VI.7 87.6 | (M+H)⁺ = 345 | 0.34 (A) |
| 1.057 | Me | 4-cyanophenyl | -C(CH₃)₂-(CH₂)₄-C(O)-O-CH₃ | VI.7 86.0 | (M+H)⁺ = 432 | 0.37 (A) |
| 1.058 | Me | 4-cyanophenyl | -C(CH₃)₂-CH₂-C(O)-O-CH₂CH₃ | VI.7 63.4 | (M+H)⁺ = 404 | 0.49 (A) |
| 1.059 | Me | 4-cyanophenyl | -C(CH₃)₂-CH₂-CH₂-CH₂-C(O)-O-CH₂CH₃ | VI.7 78.0 | (M−H)⁻ = 430 | 0.33 (A) |

-continued

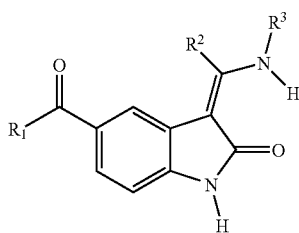

| Example | R¹ | R² | R³ | Educt Yield [%] | Mass spectrum (ES) m/z | R_f value (silica gel) (eluant) |
|---|---|---|---|---|---|---|
| 1.060 | Me | Ph | t-Bu | III 68.0 | (M+H)⁺ = 335 | 0.52 (A) |
| 1.061 | Me | benzo[1,3]dioxol-5-yl | -(CH₂)₃-NH-C(O)-O-t-Bu | VI.1 57.0 | (M+H)⁺ = 480 | 0.44 (A) |
| 1.062 | Me | 4-cyanophenyl | -(CH₂)₃-NH-C(O)-CH₃ | VI.7 89.5 | (M+H)⁺ = 403 | 0.35 (A) |
| 1.063 | Me | benzo[1,3]dioxol-5-yl | -(CH₂)₃-N(CH₃)₂ | VI.1 63.3 | (M+H)⁺ = 408 | 0.18 (A) |
| 1.064 | Me | benzo[1,3]dioxol-5-yl | -(CH₂)₃-NH-C(O)-CH₃ | VI.1 65.7 | (M+H)⁺ = 422 | 0.38 (A) |
| 1.065 | Me | benzo[1,3]dioxol-5-yl | -(CH₂)₃-imidazol-1-yl | VI.1 74.5 | (M+H)⁺ = 431 | 0.41 (A) |
| 1.066 | Me | benzo[1,3]dioxol-5-yl | -(CH₂)₃-NH-(3-chloro-5-trifluoromethylpyridin-2-yl) | IV.1 67.2 | (M+H)⁺ = 559/561 (Cl) | 0.55 (A) |

-continued

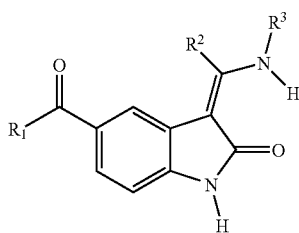

| Example | R¹ | R² | R³ | Educt Yield [%] | Mass spectrum (ES) m/z | R$_f$-value (silica gel) (eluant) |
|---|---|---|---|---|---|---|
| 1.067 | Me | benzo[1,3]dioxol-5-yl | 3-(4-methylpiperazin-1-yl)propyl | VI.1 57.4 | (M+H)⁺ = 463 | 0.26 (A) |
| 1.068 | Me | benzo[1,3]dioxol-5-yl | 3-(dimethylamino)-2,2-dimethylpropyl | VI.1 61.0 | (M+H)⁺ = 436 | 0.36 (A) |
| 1.069 | Me | Ph | 3-acetamidopropyl | III 61.1 | (M+H)⁺ = 378 | 0.29 (A) |
| 1.070 | Me | benzo[1,3]dioxol-5-yl | 3-(2-oxopyrrolidin-1-yl)propyl | VI.1 84.8 | (M+H)⁺ = 448 | 0.42 (A) |
| 1.071 | Me | benzo[1,3]dioxol-5-yl | 3-benzamidopropyl | VI.1 62.0 | (M+H)⁺ = 484 | 0.44 (A) |
| 1.072 | Me | 3-(imidazol-1-yl)propyl | 3-(dimethylamino)propyl | VI.22 58.0 | (M+H)⁺ = 436 | 0.46 (A) |
| 1.073 | Me | benzo[1,3]dioxol-5-yl | 3-(N-methyl-N-Boc-amino)propyl | VI.1 99.9 | (M+H)⁺ = 494 | 0.46 (A) |

-continued

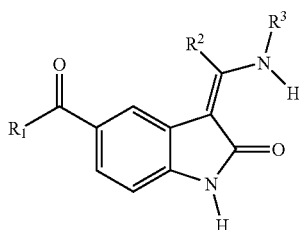

| Example | R¹ | R² | R³ | Educt Yield [%] | Mass spectrum (ES) m/z | R_f value (silica gel) (eluant) |
|---|---|---|---|---|---|---|
| 1.074 | Me | benzodioxole | propyl-NH-C(O)-CH2CH3 | VI.1 71.8 | (M+H)⁺ = 450 | 0.48 (A) |
| 1.075 | Me | benzodioxole | propyl-NH-C(O)-CH(CH3)2 | VI.1 65.4 | (M+H)⁺ = 450 | 0.44 (A) |
| 1.076 | Me | benzodioxole | propyl-NH-SO2-CH3 | VI.1 58.1 | (M+H)⁺ = 458 | 0.55 (A) |
| 1.077 | Me | propyl-imidazole | pentyl-N(CH3)2 | VI.22 84.8 | (M+H)⁺ = 464 | 0.51 (C) |
| 1.078 | Me | propyl-imidazole | propyl-N(CH3)2 | VI.22 68.7 | (M+H)⁺ = 450 | 0.33 (C) |
| 1.079 | Me | propyl-imidazole | hexyl-N(CH3)2 | VI.22 58.8 | (M+H)⁺ = 478 | 0.31 (C) |
| 1.080 | Me | benzodioxole | neopentyl-NH-C(O)-O-tBu | VI.1 93.5 | (M+H)⁺ = 508 | 0.4 (A) |
| 1.081 | Me | benzodioxole | CH2C(CH3)2CH2OH | VI.1 76.0 | (M+H)⁺ = 367 | 0.46 (A) |

-continued

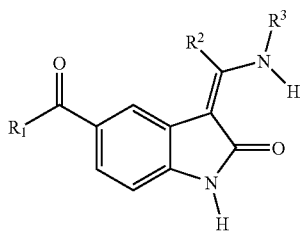

| Example | R¹ | R² | R³ | Educt Yield [%] | Mass spectrum (ES) m/z | $R_f$ value (silica gel) (eluant) |
|---|---|---|---|---|---|---|
| 1.082 | Me | benzo[1,3]dioxol-5-yl | -CH₂CH₂CH₂-O-CH₃ | VI.1 66.6 | (M+H)⁺ = 381 | 0.44 (A) |
| 1.083 | Me | benzo[1,3]dioxol-5-yl | -CH₂CH₂CH₂-O-CH₂CH₂-OH | VI.1 69.7 | (M+H)⁺ = 411 | 0.43 (A) |
| 1.084 | Me | benzo[1,3]dioxol-5-yl | -C(CH₃)₂CH₂CH₂-O-CH₃ | VI.1 55.2 | (M+H)⁺ = 395 | 0.47 (A) |
| 1.085 | Me | Ph | H | III 97.0 | (M+H)⁺ = 279 | 0.39 (C) |
| 1.086 | Me | 4-nitrophenyl | H | VI.3 85.1 | (M+H)⁺ = 324 | 0.53 (C) |
| 1.087 | Me | benzo[1,3]dioxol-5-yl | -C(CH₃)₂CH₂CH₂-C(O)-O-CH₃ | VI.12 51.5 | (M+H)⁺ = 437 | 0.39 (A) |
| 1.088 | Me | benzo[1,3]dioxol-5-yl | -C(CH₃)₂CH₂CH₂CH₂-OH | VI.19 66.6 | (M+H)⁺ = 381 | 0.43 (A) |

-continued

| Example | R¹ | R² | R³ | Educt Yield [%] | Mass spectrum (ES) m/z | R_f value (silica gel) (eluant) |
|---|---|---|---|---|---|---|
| 1.089 | Me | benzo[1,3]dioxol-5-yl | -(CH₂)₄-N(CH₃)₂ | VI.19 69.1 | (M+H)⁺ = 422 | 0.09 (A) |
| 1.090 | Me | benzo[1,3]dioxol-5-yl | -CH₂-C₆H₄-CH₂-N(CH₃)₂ | VI.19 28.8 | (M+H)⁺ = 484 | 0.40 (A) |
| 1.091 | Me | benzo[1,3]dioxol-5-yl | -(CH₂)₃-O-(CH₂)₂-N(Et)₂ | VI.19 92.4 | (M+H)⁺ = 480 | 0.12 (A) |
| 1.092 | Me | benzo[1,3]dioxol-5-yl | (S)-CH(iBu)-C(O)OCH₃ | VI.1 67.0 | (M+H)⁺ = 451 | 0.45 (A) |
| 1.093 | Me | benzo[1,3]dioxol-5-yl | (R)-CH(iBu)-C(O)OCH₃ | VI.1 55.0 | (M+H)⁺ = 451 | 0.45 (A) |
| 1.094 | Me | benzo[1,3]dioxol-5-yl | -CH₂-O-CH₂CH₃ | VI.1 72.0 | (M+H)⁺ = 367 | 0.47 (A) |
| 1.095 | Me | benzo[1,3]dioxol-5-yl | -(CH₂)₃-NH-C(O)CH₃ | VI.1 84.0 | (M+H)⁺ = 316 | 0.41 (A) |

-continued

| Example | R¹ | R² | R³ | Educt Yield [%] | Mass spectrum (ES) m/z | R_f value (silica gel) (eluant) |
|---|---|---|---|---|---|---|
| 1.096 | Me | benzo[1,3]dioxol-5-yl (with gem-dimethyl) | -C(Me)₂-CH₂-CH₂-(4-pyridyl) | VI.1 66.0 | (M−H)⁻ = 440 | 0.53 (A) |
| 1.097 | Me | Ph | -CH₂-CH₂-CH₂-(4-pyridyl) | III 60.0 | (M−H)⁻ = 396 | 0.52 (A) |
| 1.098 | Me | Ph | -CH₂-CH₂-CH₂-(3-pyridyl) | III 59.0 | (M+H)⁺ = 398 | 0.60 (C) |
| 1.099 | Me | Ph | -CH₂-CH₂-CH₂-O-Ph | III 85.0 | (M+H)⁺ = 399 | 0.59 (C) |
| 1.100 | Me | Ph | -CH₂-CH₂-(indol-3-yl) | III 84.0 | (M+H)⁺ = 422 | 0.52 (C) |
| 1.101 | Me | Ph | -CH₂-CH₂-NH-(4-pyridyl) | III 70.0 | (M+H)⁺ = 399 | 0.25 (C) |
| 1.102 | Me | Ph | -CH₂-CH₂-CH₂-CH₂-(4-pyridyl) | III 73.0 | (M+H)⁺ = 412 | 0.42 (C) |
| 1.103 | Me | Ph | -CH₂-CH₂-(4-pyridyl) | III 89.0 | (M+H)⁺ = 384 | 0.41 (C) |
| 1.104 | Me | Ph | -CH₂-CH₂-CH₂-Ph | III 86.0 | (M+H)⁺ = 397 | 0.58 (C) |

-continued
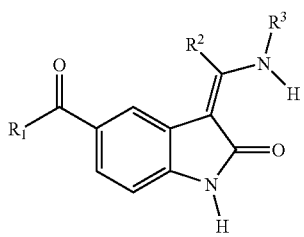
| Example | R¹ | R² | R³ | Educt Yield [%] | Mass spectrum (ES) m/z | $R_f$ value (silica gel) (eluant) |
|---|---|---|---|---|---|---|
| 1.105 | Me | Ph | —(CH₂)₄—Ph | III 81.0 | (M+H)⁺ = 411 | 0.44 (A) |
| 1.106 | Me | Ph | —CH(CH₃)CH₂CH₂—Ph | III 49.0 | (M+H)⁺ = 411 | 0.43 (A) |
| 1.107 | Me | Ph | —CH(CH₃)CH₂CH₂—Ph | III 40.0 | (M+H)⁺ = 411 | 0.41 (A) |
| 1.108 | Me | Ph | —C(CH₃)₂CH₂CH₂—Ph | III 73.0 | (M+H)⁺ = 439 | 0.46 (A) |
| 1.109 | Me | Ph | —(CH₂)₅—Ph | III 90.0 | (M+H)⁺ = 425 | 0.49 (A) |
| 1.110 | Me | Ph | —(CH₂)₄—C₆H₄—OCH₃ | III 90.0 | (M+H)⁺ = 441 | 0.40 (A) |
| 1.111 | Me | Ph | —(CH₂)₃—C₆H₄—NO₂ | III 93.0 | (M+H)⁺ = 442 | 0.32 (A) |
| 1.112 | Me | Ph | —(CH₂)₄—CH₃ | III 78.0 | (M+H)⁺ = 335 | 0.50 (A) |
| 1.113 | Me | Ph | —CH₂C(O)NH—Ph | III 89.0 | (M+H)⁺ = 412 | 0.50 (C) |

-continued
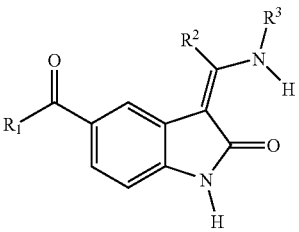
| Example | R¹ | R² | R³ | Educt Yield [%] | Mass spectrum (ES) m/z | $R_f$ value (silica gel) (eluant) |
|---|---|---|---|---|---|---|
| 1.114 | Me | Ph | 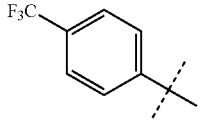 | III 87.0 | (M+H)⁺ = 436 | n.d. |
| 1.115 | Me | 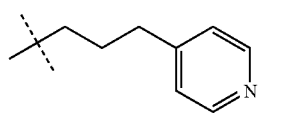 | 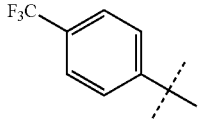 | VI.8 61.0 | (M+H)⁺ = 466 | 0.35 (A) |
| 1.116 | Me | 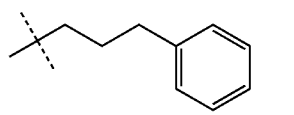 | 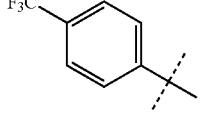 | VI.8 80.0 | (M+H)⁺ = 465 | 0.37 (A) |
| 1.117 | Me | 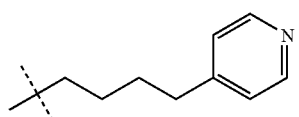 | 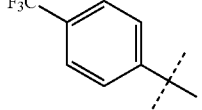 | VI.8 77.0 | (M+H)⁺ = 480 | 0.31 (A) |
| 1.118 | Me | 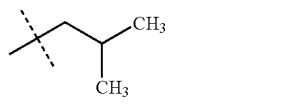 | 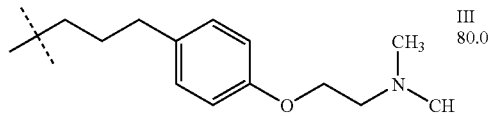 | VI.8 56.0 | (M+H)⁺ = 403 | 0.50 (A) |
| 1.119 | Me | Ph | 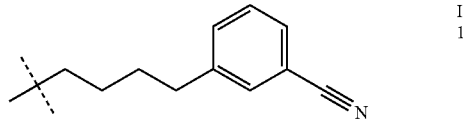 | III 80.0 | (M+H)⁺ = 484 | 0.45 (A) |
| 1.120 | Me | Ph | 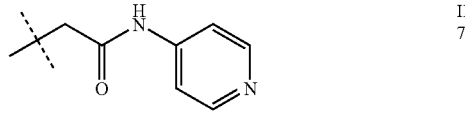 | III 10.0 | (M+H)⁺ = 436 | 0.60 (A) |
| 1.121 | Me | Ph | 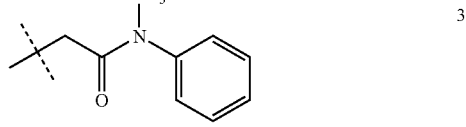 | III 75.0 | (M+H)⁺ = 413 | 0.43 (A) |
| 1.122 | Me | Ph |  | III 30.0 | (M+H)⁺ = 426 | 0.48 (A) |

-continued

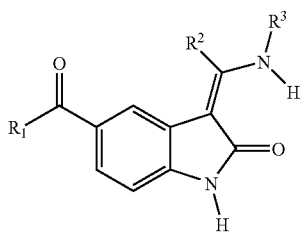

| Example | R¹ | R² | R³ | Educt Yield [%] | Mass spectrum (ES) m/z | $R_f$ value (silica gel) (eluant) |
|---|---|---|---|---|---|---|
| 1.123 | Me | Ph | (CH2-C(Me)2-C(O)-NH-CH2-4-pyridyl) | III 66.0 | (M+H)⁺ = 427 | 0.55 (A) |
| 1.124 | Me | 4-F3C-C6H4 | (CH2-C(Me)2-CH2-CH2-NH-C(O)-CH3) | VI.8 54.0 | (M+H)⁺ = 446 | 0.28 (A) |
| 1.125 | Me | 3,4-F2-C6H3 | (CH2-C(Me)2-CH2-CH2-CH3) | VI.20 79.0 | (M+H)⁺ = 371 | 0.21 (A) |
| 1.126 | Me | 3,4-F2-C6H3 | (CH2-C(Me)2-CH2-CH2-CH2-CH3) | VI.20 77.0 | (M+H)⁺ = 385 | 0.20 (A) |
| 1.127 | Me | Et | (CH2-C(Me)2-CH2-CH2-Ph) | III.3 73.0 | (M+H)⁺ = 349 | 0.44 (E) |
| 1.128 | Me | Et | (CH2-C(Me)2-CH2-CH(CH3)2) | III.3 69.0 | (M+H)⁺ = 387 | 0.48 (E) |
| 1.129 | Me | n-Pr | (CH2-C(Me)2-CH2-CH2-Ph) | III.4 94.0 | (M−H)⁻ = 361 | 0.47 (A) |
| 1.130 | Me | n-Pr | (CH2-C(Me)2-CH2-CH(CH3)2) | III.4 93.0 | (M+H)⁺ = 301 | 0.51 (A) |
| 1.131 | Me | n-Pr | (CH2-C(Me)2-CH2-CH2-CH3) | III.4 74.0 | (M+H)⁺ = 301 | 0.63 (A) |

-continued

| Example | R¹ | R² | R³ | Educt Yield [%] | Mass spectrum (ES) m/z | R_f value (silica gel) (eluant) |
|---|---|---|---|---|---|---|
| 1.132 | Me | n-Pr | ⸺CH₂CH₂CH₂CH₂N(CH₃)₂ | III.4 47.0 | (M+H)⁺ = 344 | 0.31 (C) |
| 1.133 | Me | n-Pr | ⸺CH₂CH₂CH₂N(CH₃)₂ | III.4 38.0 | (M+H)⁺ = 330 | 0.62 (C) |
| 1.134 | Me | n-Pr | ⸺(CH₂)₅N(CH₃)₂ | III.4 45.0 | (M+H)⁺ = 358 | 0.51 (C) |
| 1.135 | Me | n-Bu | ⸺CH₂CH₂CH₂-Ph | III.5 94.0 | (M+H)⁺ = 377 | 0.54 (E) |
| 1.136 | Me | n-Bu | ⸺CH₂CH₂CH(CH₃)₂ | III.5 86.0 | (M+H)⁺ = 315 | 0.69 (E) |
| 1.137 | Me | n-Bu | ⸺(CH₂)₄CH₃ | III.5 81.0 | (M+H)⁺ = 315 | 0.69 (E) |
| 1.138 | Me | n-Bu | ⸺CH₂CH₂CH₂CH₂N(CH₃)₂ | III.5 59.0 | (M+H)⁺ = 358 | 0.22 (A) |
| 1.139 | Me | n-Bu | ⸺CH₂CH₂CH₂N(CH₃)₂ | III.5 55.0 | (M+H)⁺ = 344 | 0.22 (A) |
| 1.140 | Me | n-Bu | ⸺(CH₂)₅N(CH₃)₂ | III.5 42.0 | (M+H)⁺ = 372 | 0.12 (A) |
| 1.141 | Me | 3,4-methylenedioxyphenyl | ⸺CH₂CH₂CH₂NHC(O)CH₂N(CH₃)₂ | VI.1 69.8 | (M+H)⁺ = 465 | 0.36 (A) |

-continued
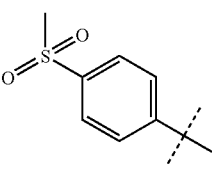
| Example | R¹ | R² | R³ | Educt Yield [%] | Mass spectrum (ES) m/z | $R_f$ value (silica gel) (eluant) |
|---|---|---|---|---|---|---|
| 1.142 | Me | 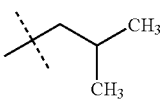 | 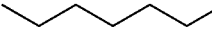 | VI.25 68.0 | (M+H)⁺ = 413 | 0.52 (A) |
| 1.143 | Me | 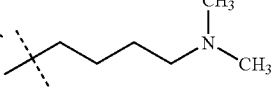 | 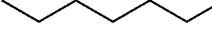 | VI.26 79.6 | (M+H)⁺ = 400 | 0.08 (A) |
| 1.144 | Me | 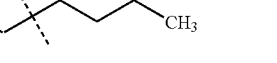 |  | VI.26 62.1 | (M+H)⁺ = 357 | 0.51 (A) |
| 1.145 | Me | 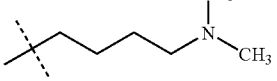 | 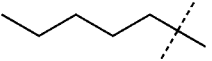 | VI.27 76.4 | (M+H)⁺ = 386 | 0.11 (A) |
| 1.146 | Me | 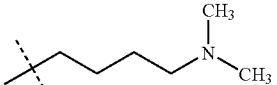 |  | VI.28 22.0 | (M+H)⁺ = 372 | 0.23 (C) |
| 1.147 | Me | 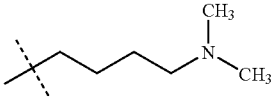 | 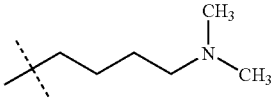 | VI.29 12.0 | (M+H)⁺ = 358 | 0.16 (C) |
| 1.148 | Et | Et | 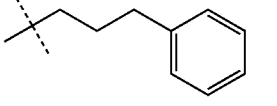 | III.7 70.0 | (M+H)⁺ = 344 | 0.11 (A) |
| 1.149 | Et | Et | 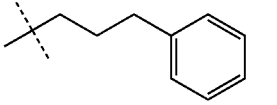 | III.7 87.0 | (M+H)⁺ = 363 | 0.45 (A) |
| 1.150 | n-C₅H₁₁ | Et | 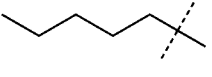 | III.8 73.0 | (M+H)⁺ = 405 | 0.47 (A) |
| 1.151 | Me | 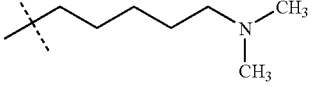 | | VI.28 75.0 | (M+H)⁺ = 486 | 0.27 (C) |

-continued

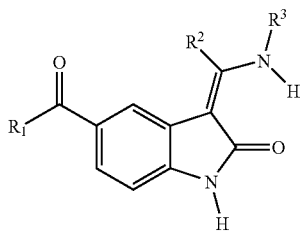

| Example | R¹ | R² | R³ | Educt Yield [%] | Mass spectrum (ES) m/z | $R_f$ value (silica gel) (eluant) |
|---|---|---|---|---|---|---|
| 1.152 | Me | | | VI.28 58.0 | $(M+H)^+$ = 391 | 0.46 (A) |
| 1.153 | Me | | | VI.29 37.0 | $(M+H)^+$ = 315 | 0.66 (A) |
| 1.154 | Me | | | VI.29 51.0 | $(M+H)^+$ = 372 | 0.24 (A) |
| 1.155 | Me | | | VI.29 50.0 | $(M+H)^+$ = 377 | 0.47 (C) |

EXAMPLE 2

5-acetyl-3-[benzo[3]dioxol-5-yl-(3-methylamino-propylamino)-methylidene]-2-indolinone

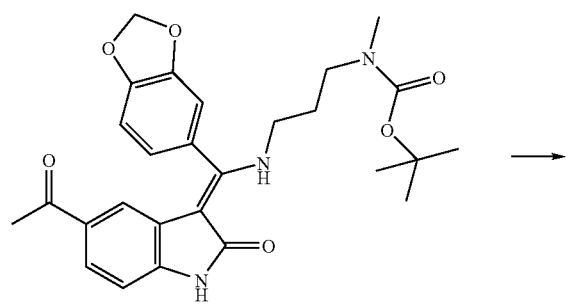

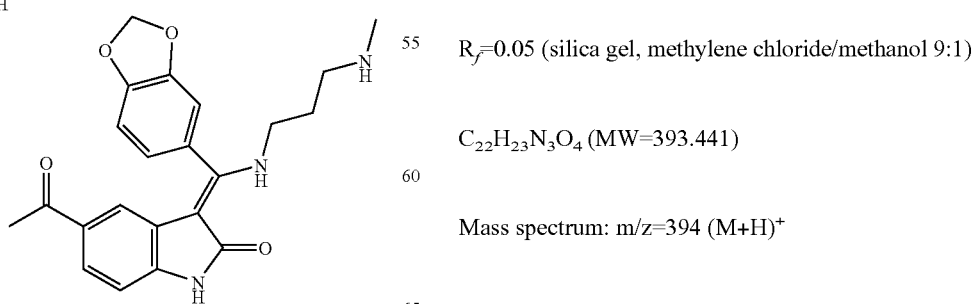

680 mg (1.38 mmol) 5-acetyl-3-[benzo[1.3]dioxol-5-yl-(3-(N-tert-butoxycarbonyl-N-methyl-amino)-propylamino)-methylidene]-2-indolinone (Example 1.073) are added batchwise to a solution of 2 ml trifluoroacetic acid in 20 ml methylene chloride and stirred for 5 h at ambient temperature. Then the mixture is evaporated down, the residue is taken up in methylene chloride, made alkaline with 1 N sodium hydroxide solution and then the organic phase is separated off, dried over sodium sulphate and evaporated down.

Yield: 210 mg (38% of theory)

$R_f$=0.05 (silica gel, methylene chloride/methanol 9:1)

$C_{22}H_{23}N_3O_4$ (MW=393.441)

Mass spectrum: m/z=394 $(M+H)^+$

The following compounds of formula I are prepared analogously to Example 2:

| Example | R¹ | R² | R³ | Educt Yield [%] | Mass spectrum (ES) m/z | R_f value (silica gel) (eluant) |
|---|---|---|---|---|---|---|
| 2.001 | Me | Ph | 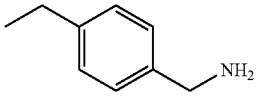 | 1.013 65.1 | (M+H)⁺ = 398 | 0.14 (B) |
| 2.002 | Me | Ph | 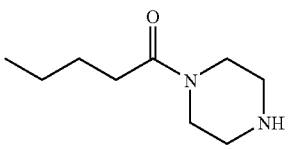 | 4.014 52.9 | (M+H)⁺ = 433 | 0.48 (C) |
| 2.003 | Me | Ph | 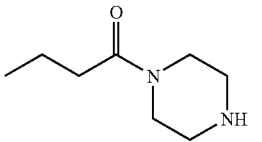 | 4.016 56.7 | (M+H)⁺ = 419 | 0.38 (C) |
| 2.004 | Me | Ph | 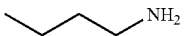 | 1.041 53.2 | (M+H)⁺ = 336 | 0.40 (C) |
| 2.005 | Me | 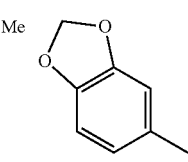 | 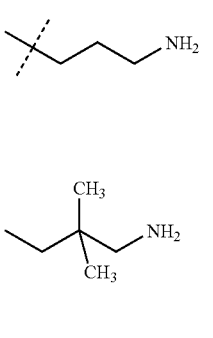 | 1.061 97.3 | (M+H)⁺ = 380 | 0.08 (A) |
| 2.006 | Me | 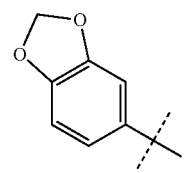 | 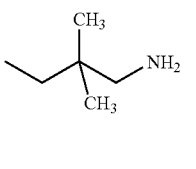 | 1.080 81.1 | (M+H)⁺ = 408 | 0.1 (A) |
| 2.007 | Me | Ph | 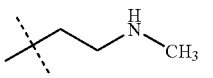 | 1.114 82.0 | (M+H)⁺ = 336 | 0.32 (C) |

EXAMPLE 3

5-acetyl-3-[(carboxymethyl-amino)-phenyl-methylidene]-2-indolinone

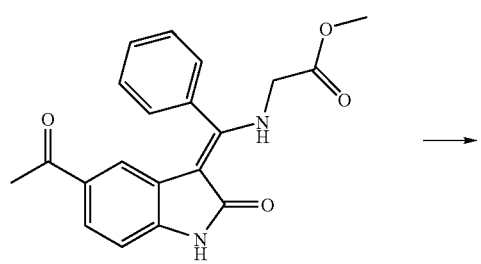

→

-continued

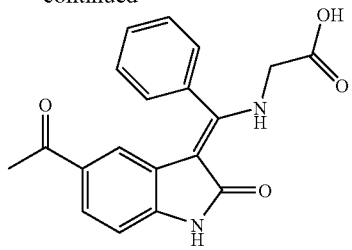

88 mg (0.25 mmol) 5-acetyl-3-[(methoxycarboxymethyl-amino)-phenyl-methylidene]-2-indolinone (Example 1.005) are suspended in 0.5 ml 1 N sodium hydroxide solution and 5 ml of methanol and refluxed for 4 h. Then the mixture is cooled, 0.5 ml 1 N hydrochloric acid are added and the precipitate is removed by suction filtering.

Yield: 81 mg (95% of theory)

$C_{19}H_6N_2O_4$ (MW=336.345)

Mass spectrum: m/z=337 (M+H)⁺

The following compounds of formula I are prepared analogously to Example 3:

| Example | R¹ | R² | R³ | Educt Yield [%] | Mass spectrum (ES) m/z | R$_f$ value (silica gel) (eluant) |
|---|---|---|---|---|---|---|
| 3.001 | Me | Ph | (3,3-dimethyl-butanoic acid group) | 1.004 91.3 | (M+H)⁺ = 351 | not determined |
| 3.002 | Me | Ph | (4,4-dimethyl-pentanoic acid group) | 1.014 34.6 | (M+H)⁺ = 365 | 0.19 (A) |
| 3.003 | Me | Ph | (2,2-dimethyl-propanoic acid with CH₃ group) | 1.012 88.5 | (M−H)⁻ = 349 | 0.47 (A + glacial acetic acid) |
| 3.004 | Me | Ph | (6,6-dimethyl-heptanoic acid group) | 1.022 57.0 | (M+H)⁺ = 393 | 0.26 (A) |
| 3.005 | Me | (benzo[1,3]dioxole) | (4,4-dimethyl-pentanoic acid group) | 1.022 85.5 | (M+H)⁺ = 409 | 0.31 (A) |
| 3.006 | Me | (3,4-dichlorophenyl) | (4,4-dimethyl-pentanoic acid group) | 1.026 42.5 | (M−H)⁻ = 431/433/435 (Cl2) | 0.31 (A) |
| 3.007 | Me | (chloro-pyridinyl-aminopropyl) | (trifluoro-dimethyl-propanoic acid group) | 1.036 82.7 | (M−H)⁻ = 421 | 0.33 (A) |
| 3.008 | Me | (4-trifluoromethylphenyl) | (4,4-dimethyl-pentanoic acid group) | 1.037 41.3 | (M−H)⁻ = 431 | 0.22 (A) |
| 3.009 | Et | (benzo[1,3]dioxole) | (4,4-dimethyl-pentanoic acid group) | 1.087 82.6 | (M+H)⁺ = 423 | 0.78 (B) |

-continued
| Example | R¹ | R² | R³ | Educt Yield [%] | Mass spectrum (ES) m/z | R$_f$ value (silica gel) (eluant) |
|---|---|---|---|---|---|---|
| 3.010 | Me | 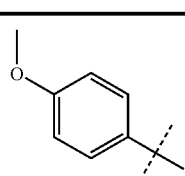 | 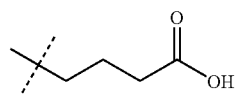 | 1.038 93.1 | (M−H)⁻ = 393 | 0.7 (B) |
| 3.011 | Me | 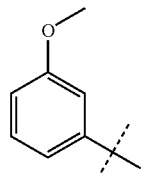 | 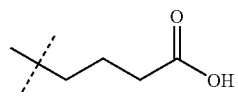 | 1.039 79.2 | (M−H)⁻ = 393 | 0.33 (A) |
| 3.012 | Me | 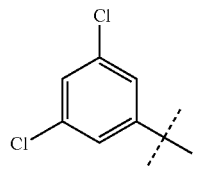 | 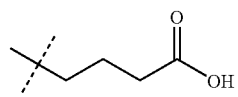 | 1.042 90.9 | (M+H)⁺ = 433/435/ 437 (Cl2) | 0.32 (A) |
| 3.013 | Me | 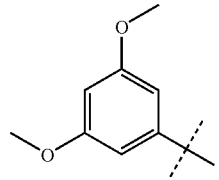 | 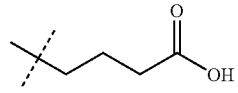 | 1.043 77.5 | (M+H)⁺ = 425 | 0.27 (A) |
| 3.014 | Me | 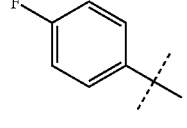 | 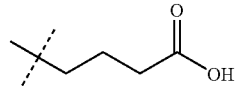 | 1.047 79.4 | (M+H)⁺ = 383 | 0.38 (A) |
| 3.015 | Me | 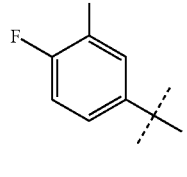 | 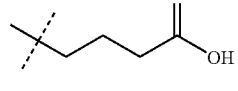 | 1.049 78.4 | (M+H)⁺ = 401 | 0.36 (A) |
| 3.016 | Me | NH₂ 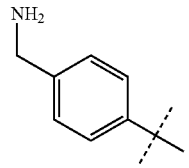 | 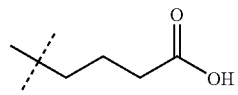 | 7.004 19.5 | (M+H)⁺ = 394 | 0.09 (A + glacial acetic acid) |
| 3.017 | Me | NH₂ 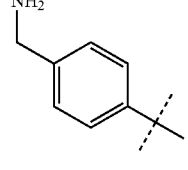 | 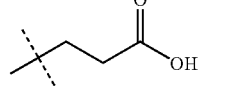 | 7.012 95.5 | (M+H)⁺ = 380 | 0.05 (A + glacial acetic acid) |

-continued
| Example | R¹ | R² | R³ | Educt Yield [%] | Mass spectrum (ES) m/z | R_f value (silica gel) (eluant) |
|---|---|---|---|---|---|---|
| 3.018 | Me | NH₂ 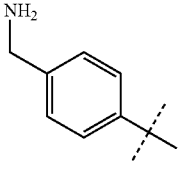 | 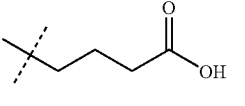 | 7.010 56.3 | (M+H)⁺ = 442 | 0.02 (C) |
| 3.019 | Me | 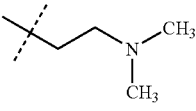 | 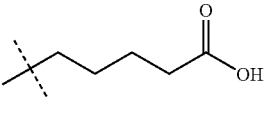 | 6.006 98 | (M+H)⁺ = 436 | 0.39 (A + glacial acetic acid) |
| 3.020 | Me | OH 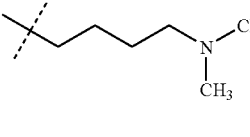 | 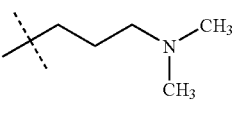 | 1.072 82.5 | (M+H)⁺ = 442 | 0.45 (MeOH) |
| 3.021 | Me | NH₂ | | 5.014 93.4 | (M+H)⁺ = 408 | 0.39 (MeOH) |
| 3.022 | Me | OH | | 1.077 85.9 | (M+H)⁺ = 450 | 0.24 (MeOH) |
| 3.023 | Me | OH | | 1.078 72.4 | (M+H)⁺ = 436 | 0.22 (MeOH) |

EXAMPLE 4

5-acetyl-3-{[3-(N,N-bis-(2-hydroxyethyl)-carbamoyl)-propylamino]-phenyl-methylene}-2-indolinone

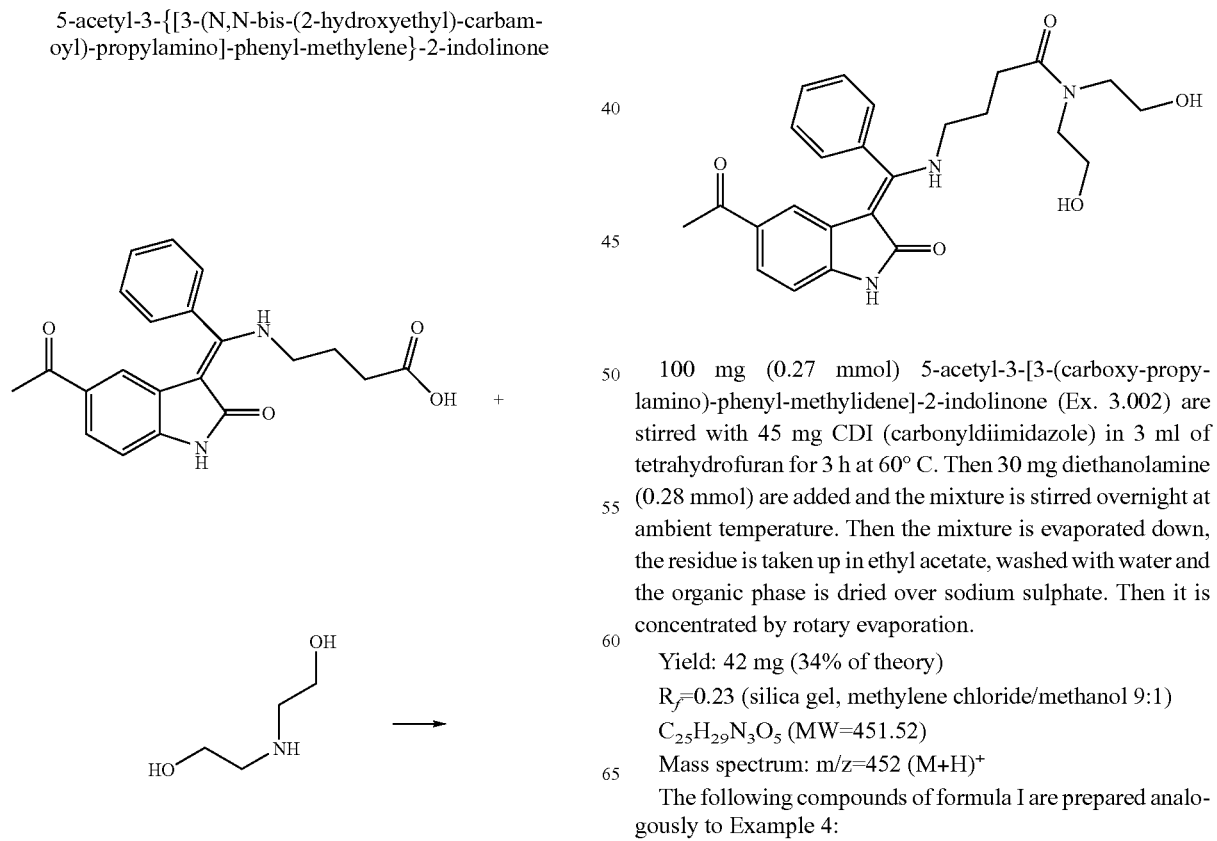

100 mg (0.27 mmol) 5-acetyl-3-[3-(carboxy-propylamino)-phenyl-methylidene]-2-indolinone (Ex. 3.002) are stirred with 45 mg CDI (carbonyldiimidazole) in 3 ml of tetrahydrofuran for 3 h at 60° C. Then 30 mg diethanolamine (0.28 mmol) are added and the mixture is stirred overnight at ambient temperature. Then the mixture is evaporated down, the residue is taken up in ethyl acetate, washed with water and the organic phase is dried over sodium sulphate. Then it is concentrated by rotary evaporation.

Yield: 42 mg (34% of theory)

$R_f$=0.23 (silica gel, methylene chloride/methanol 9:1)

$C_{25}H_{29}N_3O_5$ (MW=451.52)

Mass spectrum: m/z=452 (M+H)$^+$

The following compounds of formula I are prepared analogously to Example 4:

| Example | R¹ | R² | R³ | Educt Yield [%] | Mass spectrum (ES) m/z | R_f value (silica gel) (eluant) |
|---|---|---|---|---|---|---|
| 4.001 | Me | Ph | CH₃CH₂CH₂C(O)NH-CH₂CH₂-N(CH₃)₂ | 3.001 29.2 | (M+H)⁺ = 421 | 0.12 (CH₂Cl₂/MeOH 1:1) |
| 4.002 | Me | Ph | CH₃CH₂CH₂C(O)-N(CH₃)-CH₂CH₂CH₂-N(CH₃)₂ | 3.001 54.8 | (M+H)⁺ = 449 | 0.27 (C) |
| 4.003 | Me | Ph | CH₃CH₂CH₂C(O)NHCH₃ | 3.001 29.0 | (M+H)⁺ = 364 | 0.24 (A) |
| 4.004 | Me | Ph | CH₃CH₂CH₂C(O)-N(CH₂CH₂OH)₂ | 3.001 16.0 | (M+H)⁺ = 438 | 0.16 (A) |
| 4.005 | Me | Ph | CH₃CH₂CH₂CH₂C(O)NHCH₃ | 3.002 38.7 | (M+H)⁺ = 378 | 0.35 (C) |
| 4.006 | Me | Ph | CH₃CH₂CH₂CH₂C(O)NHPh | 3.002 24.9 | (M+H)⁺ = 440 | 0.33 (A) |
| 4.007 | Me | Ph | CH₃CH₂CH₂CH₂C(O)N(CH₃)₂ | 3.002 25.9 | (M+H)⁺ = 392 | 0.54 (A) |
| 4.008 | Me | Ph | CH₃CH₂CH₂CH₂C(O)NHCH₂CH₃ | 3.002 56.9 | (M−H)⁻ = 390 | 0.57 (A) |
| 4.009 | Me | Ph | CH₃CH₂CH₂CH₂C(O)NH-CH₂CH₂-N(CH₃)₂ | 3.002 59.0 | (M+H)⁺ = 435 | 0.53 (C) |
| 4.010 | Me | Ph | CH₃CH₂CH₂CH₂C(O)-N-methylpiperazine | 3.002 90.2 | (M+H)⁺ = 447 | 0.28 (A) |

-continued

| Example | R¹ | R² | R³ | Educt Yield [%] | Mass spectrum (ES) m/z | $R_f$ value (silica gel) (eluant) |
|---|---|---|---|---|---|---|
| 4.011 | Me | Ph | (piperazine with Boc and pentanoyl) | 3.002 26.2 | $(M+H)^+$ = 533 | 0.47 (A) |
| 4.012 | Me | Ph | (pentanoyl-N(Me)-propyl-N(Me)$_2$) | 3.002 47.5 | $(M+H)^+$ = 463 | 0.34 (C) |
| 4.013 | Me | Ph | (piperazine with Boc and butanoyl) | 3.001 14.8 | $(M+H)^+$ = 519 | 0.47 (A) |
| 4.014 | Me | Ph | (dimethyl-CH$_2$-C(=O)NH$_2$) | 3.002 51.0 | $(M+H)^+$ = 364 | 0.72 (A) |

EXAMPLE 5

5-acetyl-3-[(4-aminomethyl-phenyl)-(3-dimethylamino-propylylamino)-methylidene]-2-indolinone

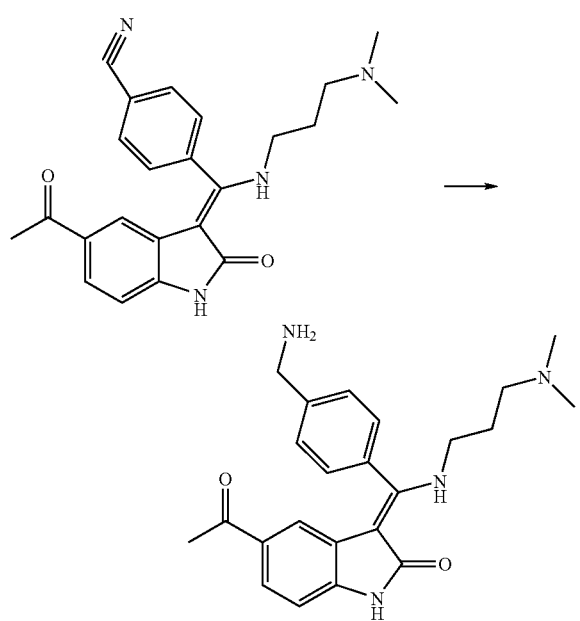

200 mg (0.51 mmol) 5-acetyl-3-[(4-cyano-phenyl)-(3-dimethylamino-propylamino)-methylidene]-2-indolinone (Example 1.054) are dissolved in 13 ml of methanolic ammonia, combined with 80 mg Raney nickel and hydrogenated at ambient temperature for 6 h at a pressure of 50 psi. Then the catalyst is filtered off and the solution is evaporated down. The residue is chromatographed through a silica gel column with methylene chloride:methanol 30:1. The desired fraction is collected and evaporated down.

Yield: 180 mg (89% of theory)

$R_f$=0.19 (silica gel, methylene chloride/methanol/conc. ammonia 9:1:0.1)

$C_{23}H_{28}N_4O_2$ (MW=392.5)

Mass spectrum: m/z=393 $(M+H)^+$

The following compounds of formula I are prepared analogously to Example 5:

| Example | R¹ | R² | R³ | Educt Yield [%] | Mass spectrum (ES) m/z | $R_f$ value (silica gel) (eluant) |
|---|---|---|---|---|---|---|
| 5.001 | Me | NH₂ | 4-(tBu-phenyl)methyl with -C(CH₃)₂-CH₂-C(=O)-O-CH₃ | 1.053 68.9 | (M+H)⁺ = 408 | 0.39 (C) |
| 5.002 | Me | NH₂ | 4-(tBu-phenyl)methyl with -C(CH₃)₂-CH(CH₃)₂ | 1.055 45.0 | (M+H)⁺ = 364 | 0.5 (C) |
| 5.003 | Me | NH₂ | n-Pr | 1.056 49.4 | (M+H)⁺ = 350 | 0.44 (C) |
| 5.004 | Me | NH₂ | 4-(tBu-phenyl)methyl with -C(CH₃)₂-(CH₂)₄-C(=O)-O-CH₃ | 1.057 84.9 | not determined | 0.43 (C) |
| 5.005 | Me | NH₂ | 4-(tBu-phenyl)methyl with -C(CH₃)₂-CH₂-CH₂-C(=O)-O-CH₃ | 1.058 57.4 | (M+H)⁺ = 394 | 0.23 (C) |
| 5.006 | Me | NH₂ | 4-(tBu-phenyl)methyl with -C(CH₃)₂-(CH₂)₃-NH-C(=O)-CH₃ | 1.062 88.6 | (M+H)⁺ = 407 | 0.26 (C) |
| 5.007 | Me | NH₂ | 4-(tBu-phenyl)methyl with -C(CH₃)₂-(CH₂)₃-C(=O)-O-CH₂-CH₃ | 1.059 68.7 | (M+H)⁺ = 436 | 0.53 (C) |

EXAMPLE 6

5-acetyl-3-{benzo[1.3]dioxol-5-yl-[3-(N-methyl-N-acetyl-amino)-propylamino]-methylene}-2-indolinone

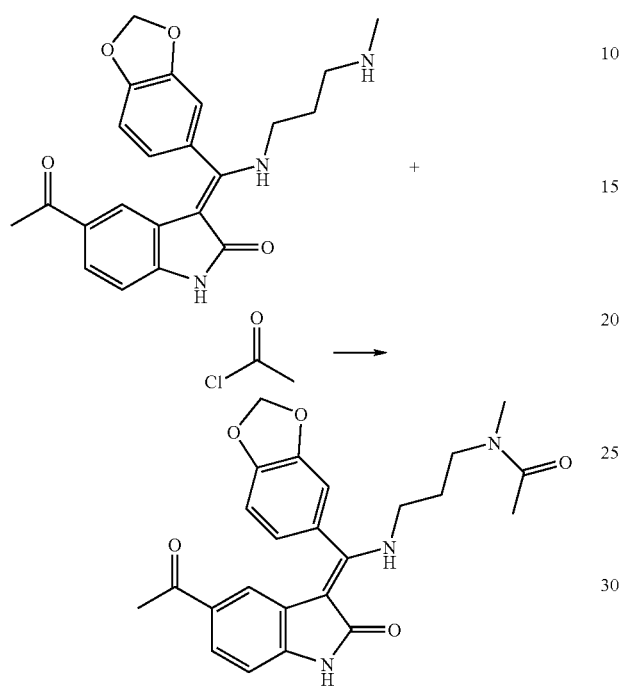

150 mg (0.38 mmol) 5-acetyl-3-[benzo[1.3]dioxol-5-yl-(3-methylamino-propylamino)-methylidene]-2-indolinone (Example 2) are placed in 4 ml methylene chloride and combined with 54 µl triethylamine. 28 µl (0.39 mmol) acetylchloride are added dropwise to this solution while cooling with ice and the mixture is stirred for 10 min. Then the mixture is left to warm up to ambient temperature and stirred for 1 h. The solution is then washed with water, the organic phase is dried over sodium sulphate, suction filtered and concentrated by rotary evaporation. The residue is eluted through a silica gel column with ethyl acetate/cyclohexane/methanol 9:9:2. The desired fraction is collected and evaporated down.

Yield: 45 mg (27% of theory)

$R_f$=0.51 (silica gel, methylene chloride/methanol 9:1)

$C_{24}H_{25}N_3O_5$ (MW=435.478)

Mass spectrum: m/z=436 (M+H)$^+$

The following compounds are prepared analogously to Example 6:

| Example | R$^1$ | R$^2$ | R$^3$ | Educt Yield [%] | Mass spectrum (ES) m/z | $R_f$ value (silica gel) (eluant) |
|---|---|---|---|---|---|---|
| 6.001 | Me | Ph | ![benzamide propyl] | 2.004 24.8 | (M+H)$^+$ = 440 | 0.30 (C) |
| 6.002 | Me | Ph | ![methyl succinate propyl] | 2.004 10.1 | (M+H)$^+$ = 450 | 0.45 (ethyl acetate/ MeOH 80:1) |
| 6.003 | Me | ![acetamidomethyl phenyl] | ![N,N-dimethyl propyl] | 5.000 53.4 | (M+H)$^+$ = 435 | 0.30 (C) |

-continued
| Example | R¹ | R² | R³ | Educt Yield [%] | Mass spectrum (ES) m/z | $R_f$ value (silica gel) (eluant) |
|---|---|---|---|---|---|---|
| 6.004 | Me | 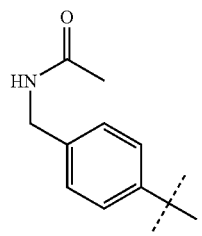 | 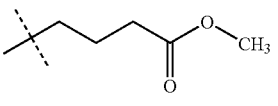 | 5.001 45.4 | (M+H)⁺ = 450 | 0.54 (C) |
| 6.005 | Me | 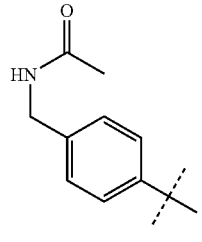 | 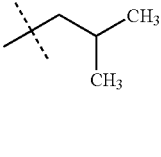 | 5.002 19.2 | (M+H)⁺ = 406 | 0.41 (C) |
| 6.006 | Me | 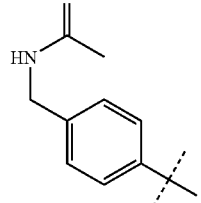 | n-Pr | 5.003 71.4 | (M+H)⁺ = 392 | 0.53 (C) |
| 6.007 | Me | 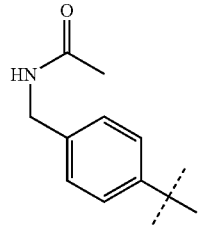 | 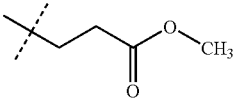 | 5.005 81.3 | (M+H)⁺ = 436 | 0.35 (C) |
| 6.008 | Me | 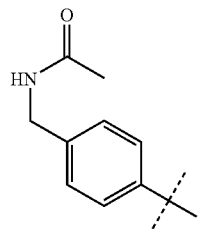 | 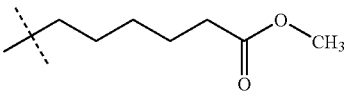 | 5.004 39.6 | (M+H)⁺ = 478 | 0.56 (C) |
| 6.009 | Me | 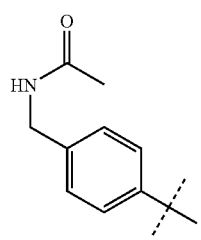 | 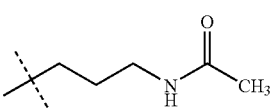 | 5.006 24.2 | (M+H)⁺ = 449 | 0.21 (A) |

-continued

| Example | R¹ | R² | R³ | Educt Yield [%] | Mass spectrum (ES) m/z | $R_f$ value (silica gel) (eluant) |
|---------|----|----|----|-----------------|------------------------|-----------------------------------|
| 6.010 | Me | | ![](pentanoate ethyl ester) | 5.007 56.9 | $(M+H)^+ =$ 478 | 0.50 (A) |
| 6.011 | Me | Ph | ![](methanesulfonamide propyl) | 2.004 25.3 | $(M+H)^+ =$ 414 | 0.28 (C) |
| 6.012 | Me | Ph | ![](N-methyl-N-phenylacetyl propyl) | 2.007 67.0 | $(M+H)^+ =$ 454 | 0.41 (A) |

EXAMPLE 7

5-acetyl-3-[(Pyrazin-2-yl)-isobutylamino-methylidene]-2-indolinone

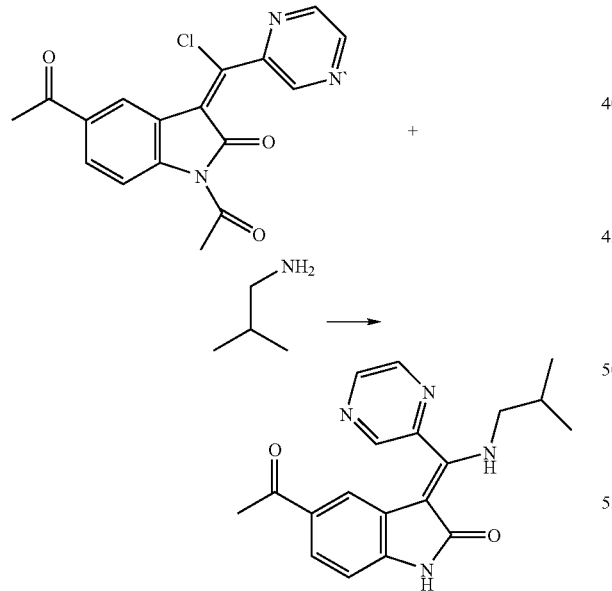

80 mg (0.23 mmol) 1.5-diacetyl-3-[chloro-(pyrazin-2-yl)-methylidene]-2-indolinone (Ex. VII) in 4 ml of tetrahydrofuran are stirred for 2 h at ambient temperature with 0.05 ml triethylamine and 0.022 g isobutylamine. The acetyl-protected intermediate product is combined with 0.8 ml of conc. ammonia without purification and stirred for half an hour at ambient temperature. Then it is evaporated down and the residue is chromatographed through a silica gel column using methylene chloride/methanol 40:1 as eluant.

Yield: 29 mg (36% of theory)
$R_f$=0.56 (silica gel, methylene chloride/methanol 9:1)
$C_{19}H_{20}N_4O_2$ (MW=336.393)
Mass spectrum: m/z=337 $(M+H)^+$

EXAMPLE 8

5-acetyl-3-[(pyridin-4-yl)-(isobutylamino)-methylidene]-2-indolinone

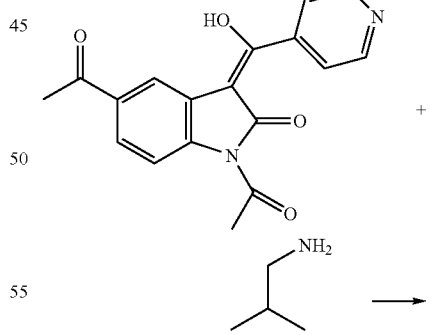

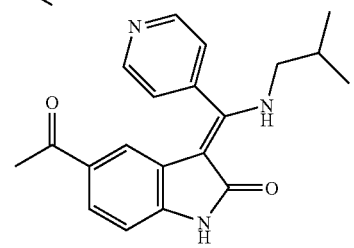

500 mg (1.55 mmol) 1.5-diacetyl-3-[(pyridin-4-yl)-hydroxy-methylidene]-2-indolinone (Ex. V.24) in 2.4 ml hexamethyldisilazane are heated to 120° C. with 0.23 g 4-amino-1-methylpiperidine for 3 h. Then the mixture is left to cool and 10 ml of methanol and 32 mg sodium methoxide are added and the mixture is stirred for 1 h at ambient temperature. Then it is evaporated down and the residue is chromatographed through a silica gel column with methylene chloride/methanol 12:1 as eluant.

Yield: 160 mg (31% of theory)

$R_f$=0.56 (silica gel, methylene chloride/methanol 9:1)

$C_{20}H_{21}N_3O_2$ (MW=335.405)

Mass spectrum: m/z=336 (M+H)$^+$

The following compound of formula I is prepared analogously to Example 8:

| Example | R$^1$ | R$^2$ | R$^3$ | Educt Yield [%] | Mass spectrum (ES) m/z | R$_f$-value (silica gel) (eluant) |
|---|---|---|---|---|---|---|
| 8.001 | Me | | | V.26 26.4 | (M+H)$^+$ = 463 | 0.58 (C) |
| 8.002 | Me | | | V.26 38.8 | (M+H)$^+$ = 420 | 0.60 (A) |
| 8.003 | Me | | | V.26 13.6 | (M+H)$^+$ = 449 | 0.49 (C) |
| 8.004 | Me | | | V.26 43.8 | (M+H)$^+$ = 464 | 0.54 (C) |
| 8.005 | Me | | | V.29 21.0 | (M+H)$^+$ = 493 | 0.41 (B) |

-continued

| Example | R¹ | R² | R³ | Educt Yield [%] | Mass spectrum (ES) m/z | $R_f$ value (silica gel) (eluant) |
|---|---|---|---|---|---|---|
| 8.006 | Me | (structure) | (structure) | V.29 12.0 | (M+H)⁺ = 436 | 0.85 (B) |
| 8.007 | Me | (structure) | (structure) | V.30 trimethyl-imidazole 70.0 | (M+H)⁺ = 450 | 0.68 (C) |
| 8.008 | Me | (structure) | (structure) | V.30 trimethyl-imidazole 54.0 | (M+H)⁺ = 513 | 0.68 (C) |

EXAMPLE 9

5-acetyl-3-[furan-3-yl-isobutylamino-methylidene]-2-indolinone

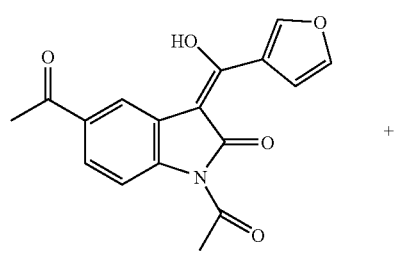

+

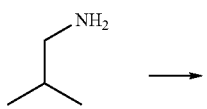

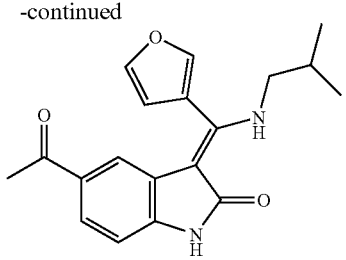

200 mg (0.65 mmol) 1.5-diacetyl-3-[furan-3-yl-methoxy-methylidene]-2-indolinone (Ex. VI.23) are suspended in 5 ml of dimethylformamide and stirred for 2 h with 61 mg isobutylamine at ambient temperature. The acetyl-protected intermediate product is combined with 1 ml of conc. ammonia without purification and stirred at ambient temperature for 30 min. Then the mixture is evaporated down and the residue is chromatographed through a silica gel column with the eluant methylene chloride/methanol 4:1.

Yield: 78 mg (37% of theory)

$R_f$=0.2 (silica gel, methylene chloride/methanol 30:1)

$C_{19}H_{20}N_2O_3$ (MW=324.383)

Mass spectrum: m/z=325 (M+H)⁺

EXAMPLE 10

5-acetyl-3-[1-(N',N'-dimethylhydrazino)-1-(4-trifluoromethyl-phenyl)-methylidene]-2-indolinone

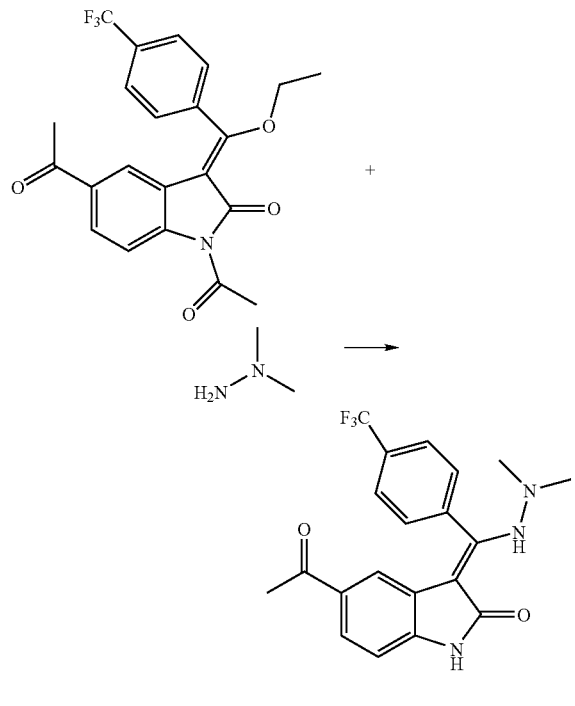

0.2 g (0.4 mmol) 1.5-diacetyl-3-[(4-trifluoromethylphenyl)-ethoxy-methylidene]-2-indolinone (Ex. VI.8) are suspended in 4 ml of dimethylformamide and stirred with 0.038 ml dimethylhydrazine at ambient temperature for 5 h. Then 2 ml of 1 N sodium hydroxide solution are added and the mixture is stirred at ambient temperature for 30 min. The reaction mixture is poured onto 10 ml of water, the precipitate is filtered off and dried in the desiccator.

If desired the product may be purified through a silica gel column with methylene chloride/methanol 30:1 as eluant.

Yield: 0.11 g (57% of theory)

$R_f$=0.55 (silica gel, methylene chloride/methanol 9:1)

$C_{20}H_{18}F_3N_3O_2$ (MW=389.371)

Mass spectrum: m/z=390 (M+H)$^+$

The following compounds are prepared analogously to Example 10:

| Example | R$^1$ | R$^2$ | R$^3$ | educt Yield [%] | Mass spectrum (ES) m/z | R$_f$ value (silica gel) (eluant) |
|---|---|---|---|---|---|---|
| 10.001 | Me | 3,4-difluorophenyl | N(CH$_3$)$_2$ | VI.20 42.0 | (M + H)$^+$ = 358 | 0.59 (A) |
| 10.002 | Me | 4-fluorophenyl | N(CH$_3$)$_2$ | VI.19 36.0 | (M + H)$^+$ = 340 | 0.24 (A) |
| 10.003 | Me | 3-methoxyphenyl | N(CH$_3$)$_2$ | VI.10 16.0 | (M + H)$^+$ = 352 | 0.48 (A) |
| 10.004 | Et | phenyl | N(CH$_3$)$_2$ | IV.3 81.0 | (M + H)$^+$ = 336 | 0.34 (A) |

-continued

| Example | R¹ | R² | R³ | educt Yield [%] | Mass spectrum (ES) m/z | R_f value (silica gel) (eluant) |
|---|---|---|---|---|---|---|
| 10.005 | Me | F₃C | [4-CF₃-phenyl-C(CH₃)₂-N(CH₃)-CH₂-phenyl] | VI.8 35.0 | (M + H)⁺ = 466 | 0.54 (A) |
| 10.006 | Me | Et | [-C(CH₃)₂-N(CH₃)₂] | III.3 63.0 | (M + H)⁺ = 274 | 0.79 (A) |
| 10.007 | Me | F₃C | [4-CF₃-phenyl-C(CH₃)₂-N(CH₃)-phenyl] | VI.8 14.0 | (M + H)⁺ = 438 | 0.50 (A) |
| 10.008 | Me | F₃C | [4-CF₃-phenyl-C(CH₃)₂-NH-C(O)CH₃] | VI.8 45.0 | (M + H)⁺ = 404 | 0.41 (A) |
| 10.009 | Me | F₃C | [4-CF₃-phenyl-C(CH₃)₂-NH-C(O)-phenyl] | VI.8 43.0 | (M + H)⁺ = 466 | 0.43 (A) |
| 10.010 | Me | F₃C | [4-CF₃-phenyl-C(CH₃)₂-NH-C(O)-O-tBu] | VI.8 29.0 | (M + H)⁺ = 460 | 0.43 (A) |
| 10.011 | Me | F₃C | [4-CF₃-phenyl-C(CH₃)₂-NH-C(O)-CH₂-phenyl] | VI.8 67.0 | (M + H)⁺ = 480 | 0.54 (A) |
| 10.012 | Me | Et | [-C(CH₃)₂-NH-phenyl] | III.3 53.0 | (M + H)⁺ = 322 | 0.53 (A) |
| 10.013 | Me | Et | [-C(CH₃)₂-NH-C(O)-phenyl] | III.3 58.0 | (M + H)⁺ = 350 | 0.40 (A) |
| 10.014 | Me | Et | [-C(CH₃)₂-N(CH₃)-CH₂-phenyl] | III.3 62.0 | (M + H)⁺ = 350 | 0.47 (A) |

| Example | R¹ | R² | R³ | educt | Yield [%] | Mass spectrum (ES) m/z | R$_f$ value (silica gel) (eluant) |
|---|---|---|---|---|---|---|---|
| 10.015 | Me | | (pentyl chain with N(CH₃)₂ group) | VI.28 | 72.0 | (M + H)⁺ = 316 | 0.67 (C) |
| 10.016 | Me | | (isobutyl chain with N(CH₃)₂ group) | VI.29 | 42.0 | (M + H)⁺ = 302 | 0.47 (C) |

EXAMPLE 11

Coated Tablets Containing 75 mg of Active Substance 1 tablet core contains:

| | |
|---|---|
| active substance | 75.0 mg |
| calcium phosphate | 93.0 mg |
| corn starch | 35.5 mg |
| polyvinylpyrrolidone | 10.0 mg |
| hydroxypropylmethylcellulose | 15.0 mg |
| magnesium stearate | 1.5 mg |
| | 230.0 mg |

Preparation:

The active substance is mixed with calcium phosphate, corn starch, polyvinylpyrrolidone, hydroxypropylmethylcellulose and half the specified amount of magnesium stearate. Blanks 13 mm in diameter are produced in a tablet-making machine and these are then rubbed through a screen with a mesh size of 1.5 mm using a suitable machine and mixed with the rest of the magnesium stearate. This granulate is compressed in a tablet-making machine to form tablets of the desired shape.

| | |
|---|---|
| Weight of core: | 230 mg |
| die: | 9 mm, convex |

The tablet cores thus produced are coated with a film consisting essentially of hydroxypropylmethylcellulose. The finished film-coated tablets are polished with beeswax.
Weight of coated tablet: 245 mg.

EXAMPLE 12

Tablets Containing 100 mg of Active Substance

Composition:

1 tablet contains:

| | |
|---|---|
| active substance | 100.0 mg |
| lactose | 80.0 mg |
| corn starch | 34.0 mg |
| polyvinylpyrrolidone | 4.0 mg |
| magnesium stearate | 2.0 mg |
| | 220.0 mg |

Method of Preparation:

The active substance, lactose and starch are mixed together and uniformly moistened with an aqueous solution of the polyvinylpyrrolidone. After the moist composition has been screened (2.0 mm mesh size) and dried in a rack-type drier at 50° C. it is screened again (1.5 mm mesh size) and the lubricant is added. The finished mixture is compressed to form tablets.

| | |
|---|---|
| Weight of tablet: | 220 mg |
| Diameter: | 10 mm, biplanar, facetted on both sides and notched on one side. |

EXAMPLE 13

Tablets Containing 150 mg of Active Substance

Composition:

1 tablet contains:

| | |
|---|---|
| active substance | 150.0 mg |
| powdered lactose | 89.0 mg |
| corn starch | 40.0 mg |
| colloidal silica | 10.0 mg |
| polyvinylpyrrolidone | 10.0 mg |
| magnesium stearate | 1.0 mg |
| | 300.0 mg |

Preparation:

The active substance mixed with lactose, corn starch and silica is moistened with a 20% aqueous polyvinylpyrrolidone solution and passed through a screen with a mesh size of 1.5 mm. The granules, dried at 45° C., are passed through the same screen again and mixed with the specified amount of magnesium stearate. Tablets are pressed from the mixture.

| Weight of tablet: | 300 mg |
| --- | --- |
| die: | 10 mm, flat |

EXAMPLE 14

Hard Gelatine Capsules Containing 150 mg of Active Substance

| 1 capsule contains: | | |
| --- | --- | --- |
| active substance | | 150.0 mg |
| corn starch (dried) | approx. | 180.0 mg |
| lactose (powdered) | approx. | 87.0 mg |
| magnesium stearate | | 3.0 mg |
| | approx. | 420.0 mg |

Preparation:

The active substance is mixed with the excipients, passed through a screen with a mesh size of 0.75 mm and homogeneously mixed using a suitable apparatus. The finished mixture is packed into size 1 hard gelatine capsules.

| Capsule filling: | approx. 320 mg |
| --- | --- |
| Capsule shell: | size 1 hard gelatine capsule. |

EXAMPLE 15

Suppositories Containing 150 ma of Active Substance

| 1 suppository contains: | |
| --- | --- |
| active substance | 150.0 mg |
| polyethyleneglycol 1500 | 550.0 mg |
| polyethyleneglycol 6000 | 460.0 mg |
| polyoxyethylene sorbitan monostearate | 840.0 mg |
| | 2,000.0 mg |

Preparation:

After the suppository mass has been melted the active substance is homogeneously distributed therein and the melt is poured into chilled moulds.

EXAMPLE 16

Suspension Containing 50 mg of Active Substance

| 100 ml of suspension contain: | |
| --- | --- |
| active substance | 1.00 g |
| carboxymethylcellulose-Na-salt | 0.10 g |
| methyl p-hydroxybenzoate | 0.05 g |
| propyl p-hydroxybenzoate | 0.01 g |
| glucose | 10.00 g |

-continued

| | |
| --- | --- |
| glycerol | 5.00 g |
| 70% sorbitol solution | 20.00 g |
| flavouring | 0.30 g |
| dist. water | ad 100 ml |

Preparation:

The distilled water is heated to 70° C. The methyl and propyl p-hydroxybenzoates together with the glycerol and sodium salt of carboxymethylcellulose are dissolved therein with stirring. The solution is cooled to ambient temperature and the active substance is added and homogeneously dispersed therein with stirring. After the sugar, the sorbitol solution and the flavouring have been added and dissolved, the suspension is evacuated with stirring to eliminate air.

5 ml of suspension contain 50 mg of active substance.

EXAMPLE 17

Ampoules Containing 10 ma Active Substance

Composition:

| | |
| --- | --- |
| active substance | 10.0 mg |
| 0.01 N hydrochloric acid q.s. | |
| double-distilled water | ad 2.0 ml |

Preparation:

The active substance is dissolved in the necessary amount of 0.01 N HCl, made isotonic with common salt, filtered sterile and transferred into 2 ml ampoules.

EXAMPLE 18

Ampoules Containing 50 ma of Active Substance

Composition:

| | |
| --- | --- |
| active substance | 50.0 mg |
| 0.01 N hydrochloric acid q.s. | |
| double-distilled water | ad 10.0 ml |

Preparation:

The active substance is dissolved in the necessary amount of 0.01 N HCl, made isotonic with common salt, filtered sterile and transferred into 10 ml ampoules.

What is claimed is:

1. Compounds of general formula

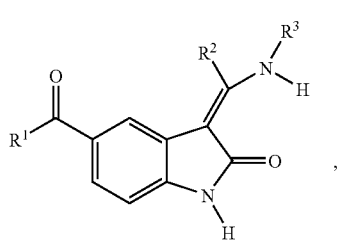

(I)

wherein
- $R^1$ denotes a straight-chain or branched $C_{1-5}$-alkyl group wherein the hydrogen atoms may be wholly or partly replaced by fluorine atoms, or
  an aryl group optionally substituted by a fluorine, chlorine or bromine atom,
  - while by an aryl group is meant a phenyl or naphthyl group,
- $R^2$ denotes a $C_{1-7}$-alkyl or $C_{3-7}$-cycloalkyl group,
  a 5- or 6-membered heteroaryl group with one to three heteroatoms selected from the group N, S and O, while both the heteratoms and the substituents may be identical or different, optionally substituted by one or two fluorine, chlorine, bromine or iodine atoms or one or two nitro, cyano, amino, $C_{1-3}$-alkyl or $C_{1-3}$-alkoxy groups,
  a phenyl group wherein two adjacent carbon atoms are linked together through a methylenedioxy, ethylenedioxy or difluoromethylenedioxy group,
  a phenyl group, to which is anellated another phenyl ring or a 5- or 6-membered heteroaromatic ring with one to three heteroatoms selected from the group N, S and O, while the heteratoms may be identical or different, and the bicyclic group may be substituted by one or two fluorine, chlorine, bromine or iodine atoms or one or two nitro, cyano, amino, $C_{1-3}$-alkyl or $C_{1-3}$-alkoxy groups and the substituents may be identical or different, or
  a phenyl group which may be substituted by one to three fluorine, chlorine, bromine or iodine atoms or by one to three $C_{1-3}$-alkyl, nitro, cyano, amino, di-($C_{1-3}$-alkyl)-amino, $C_{1-3}$-alkyl-carbonylamino, phenylcarbonylamino, $C_{1-3}$-alkylsulphonylamino, arylsulphonylamino, trifluoromethyl, $C_{1-3}$ alkylsulphonyl, carboxy, $C_{1-3}$-alkoxy, di-($C_{1-3}$-alkyl)-amino-$C_{1-3}$-alkyloxy, $C_{1-3}$-alkoxy-carbonyl, $C_{1-3}$-alkylaminocarbonyl, hydroxycarbonyl-$C_{1-3}$-alkyl-aminocarbonyl, $C_{1-3}$-alkoxycarbonyl-$C_{1-3}$-alkyl-aminocarbonyl, di-($C_{1-3}$-alkyl) -amino-$C_{1-3}$-alkylaminocarbonyl, di-($C_{1-3}$-alkyl)-aminocarbonyl-$C_{1-3}$-alkoxy, $C_{1-3}$-alkyl -amino-carbonyl-$C_{1-3}$-alkoxy, carboxy-$C_{1-3}$-alkoxy, $C_{1-3}$-alkyloxy-carbonyl-$C_{1-3}$-alkoxy, carboxy-$C_{1-3}$-alkyl, $C_{1-3}$-alkoxy-carbonyl-$C_{1-3}$-alkyl, $C_{1-3}$-alkoxy-carbonylamino-$C_{1-3}$-alkyl, amino-$C_{1-3}$-alkyl, di-($C_{1-3}$-alkyl)-amino-$C_{1-3}$lkyl, $C_{1-3}$-alkyl-carbonylamino-$C_{1-3}$-alkyl, phthalimido, pyrrolyl or mono- or di-($C_{1-3}$-alkyl)-pyrrolyl groups, while the substituents are identical or different, and
- $R^3$ denotes a hydrogen atom,
  a straight-chain or branched $C_{1-6}$-alkyl group which may be substituted by one to three carboxy, $C_{1-4}$-alkoxy-carbonyl, aminocarbonyl, $C_{1-3}$-alkylaminocarbonyl, di-($C_{1-3}$-alkyl)-aminocarbonyl, di-($C_{1-3}$-alkyl)-amino-($C_{1-3}$-alkyl)-amino-carbonyl, N-[di-($C_{1-3}$-alkyl)-amino-($C_{1-3}$-alkyl)]-N-($C_{1-3}$-alkyl)-amino-carbonyl, arylaminocarbonyl, heteroarylaminocarbonyl, aryl-$C_{1-3}$-alkyl-aminocarbonyl, heteroaryl-$C_{1-3}$-alkyl-aminocarbonyl, N-(aryl)-N -($C_{1-3}$-alkyl)-aminocarbonyl, N-(heteroaryl)-N—($C_{1-3}$-alkyl)-aminocarbonyl, di-(ω-hydroxy -$C_{2-3}$-alkyl)-aminocarbonyl, aryl or heteroaryl groups or by a 5 to 7-membered cyclo-alkyleneimino or cycloalkyleneiminocarbonyl group,
    while in the above-mentioned cycloalkyleneimino or cycloalkyleneiminocarbonyl group a methylene group may be replaced in position 3 or 4 by an —NH—, —N($C_{1-3}$-alkyl)- or —N($C_{1-4}$-alkoxy-carbonyl)- group or by an oxygen or sulphur atom and/or in position 2, 3 or 4 by a carbonyl group,
  a straight-chain or branched $C_{2-6}$-alkyl group which is substituted from position 2 onwards by one to three hydroxy, $C_{1-3}$-alkoxy, aryloxy, heteroaryloxy, amino-$C_{1-3}$-alkyloxy, $C_{1-3}$-alkyl-amino-$C_{1-3}$-alkyloxy, di-($C_{1-3}$-alkyl)-amino-$C_{1-3}$-alkyloxy, ω-hydroxy-$C_{2-3}$-alkoxy, amino, $C_{1-3}$-alkylamino, di-($C_{1-3}$-alkyl)-amino, $C_{1-3}$-alkyl-carbonylamino, heteroaryl-carbonylamino, N—($C_{1-3}$-alkyl)-N—($C_{1-3}$-alkyl-carbonyl)-amino, N—($C_{1-3}$-alkyl)-N-(heteroaryl-carbonyl)-amino, $C_{1-4}$-alkoxy-carbonylamino, N—($C_{1-3}$-alkyl)-N—($C_{1-4}$-alkoxy-carbonyl)-amino, arylcarbonylamino, N—($C_{1-3}$-alkyl)-N-(arylcarbonyl)-amino, (ω-hydroxy-$C_{2-3}$-alkyl)-amino, di-(ω-hydroxy-$C_{2-3}$-alkyl)-amino, arylamino, heteroarylamino, $C_{1-3}$-alkylsulphonylamino, N—($C_{1-3}$-alkyl)-N—($C_{1-3}$-alkylsulphonyl)-amino, $C_{1-3}$-alkoxy-carbonyl-$C_{1-3}$-alkyl-carbonylamino, ($C_{1-3}$-alkyl-amino)-carbonyl-amino, [di-($C_{1-3}$-alkyl)-amino]-carbonyl-amino, ($C_{1-3}$-alkyl-amino)-$C_{1-3}$-alkyl-carbonyl-amino, [di-($C_{1-3}$-alkyl)-amino]-$C_{1-3}$-alkyl-carbonyl-amino, N-(aryl-$C_{1-3}$-alkyl-carbonyl)-N—($C_{1-3}$-alkyl)-amino, N—($C_{1-3}$-alkyl)-N—[($C_{1-3}$-alkyl-amino)-carbonyl]-amino or N—($C_{1-3}$-alkyl)-N—{[di-($C_{1-3}$-alkyl)-amino]-carbonyl}-amino group and may optionally additionally be substituted from position 1 onwards by a carboxy, $C_{1-4}$-alkoxy-carbonyl, $C_{1-3}$-alkylaminocarbonyl, di-($C_{1-3}$-alkyl)-aminocarbonyl, arylaminocarbonyl, heteroarylaminocarbonyl-, di-(ω-hydroxy-$C_{2-3}$-alkyl)-aminocarbonyl-, aryl or heteroaryl group or by a 5 to 7-membered cyclo-alkyleneimino or cycloalkyleneiminocarbonyl group,
    while in the above-mentioned cycloalkyleneimino or cycloalkyleneiminocarbonyl group a methylene group in position 3 or 4 may be replaced by an —N—, —N($C_{1-3}$-alkyl)- or —N($C_{1-4}$-alkoxy-carbonyl)- group or by an oxygen or sulphur atom and/or in position 2, 3 or 4 by a carbonyl group,
  a $C_{2-4}$-alkenyl or $C_{2-4}$-alkynyl group, while between the nitrogen atom to which $R^3$ is bound and the multiple bond there is at least one $sp^3$-hybridised carbon atom and the alkenyl or alkynyl group may be substituted by one to three $C_{1-3}$-alkyl groups,
  a $C_{1-5}$-alkyl group in the methylene group which is adjacent to the nitrogen atom to which $R^3$ is bound may be replaced by an —N—, or a —N($C_{1-3}$-alkyl)- group or by an oxygen atom,
  a $C_{1-4}$-alkyloxy group or
  an amino group which may be substituted by one or two $C_{1-3}$-alkyl, aryl, aryl-$C_{1-3}$-alkyl, $C_{1-3}$-alkyl-carbonyl, $C_{1-4}$-alkyloxy-carbonyl, arylcarbonyl or aryl-$C_{1-3}$-alkyl-carbonyl groups, while the substituents may be identical or different,
  while the above-mentioned alkyl groups may be straight-chain or branched, the tautomers, enantiomers, diastereomers, the mixtures thereof and the salts thereof.

2. Compounds of general formula I according to claim 1, wherein
  $R^2R^3$ defined as in claim 1 and
  $R^1$ denotes a methyl, ethyl, n-propyl, isopropyl, n-pentyl, trifluoromethyl or phenyl group, the tautomers, enantiomers, diastereomers, the mixtures thereof and the salts thereof.

3. Compounds of general formula I according to claim 2, wherein
  $R^1$ denotes a methyl or ethyl group, $R^2$ denotes an ethyl, propyl, butyl or pentyl group, a pyridinyl, furanyl or pyrazinyl group, a phenyl group wherein two adjacent carbon atoms are linked together through a methylenedioxy, ethylenedioxy or difluoromethylenedioxy group, or a phenyl group which may be substituted by one or two fluorine, chlorine, bromine or iodine atoms or by one or two $C_{1-3}$-alkyl, nitro, cyano, amino, $C_{1-3}$-alkylcarbonylamino, phenylcarbonylamino, $C_{1-3}$-alkylsulphonylamino, trifluoromethyl, carboxy, $C_{1-3}$-alkoxy, di-($C_{1-3}$-alkyl)-amino-$C_{1-3}$-alkyloxy, $C_{1-3}$-alkoxy-carbonyl, $C_{1-3}$-alkylaminocarbonyl, hydroxycarbonyl-$C_{1-3}$-alkyl-aminocarbonyl, $C_{1-3}$-alkoxycarbonyl-$C_{1-3}$-alkyl-aminocarbonyl, di-($C_{1-3}$-alkyl)-amino-$C_{1-3}$-alkylaminocarbonyl, carboxy-$C_{1-3}$-alkyl, $C_{1-3}$-alkoxy-carbonyl-$C_{1-3}$-alkyl, amino-$C_{1-3}$-alkyl or $C_{1-3}$-alkyl-carbonylamino-$C_{1-3}$-alkyl groups, while the substituents are identical or different, and $R^3$ a hydrogen atom, a straight-chain or branched $C_{1-6}$-alkyl group which may be substituted by a carboxy, $C_{1-4}$-alkoxy-carbonyl, phenyl, pyridinyl, indolyl, imidazolyl, $C_{1-3}$-alkylaminocarbonyl, di-($C_{1-3}$-alkyl)-aminocarbonyl, phenylaminocarbonyl, pyridinylaminocarbonyl, di-(ω-hydroxy-$C_{2-3}$-alkyl)-aminocarbonyl or by a 5 to 7-membered cycloalkyleneimino or cycloalkyleneimino-carbonyl group, while the above-mentioned phenyl group may optionally be substituted by a nitro, cyano, $C_{1-3}$-alkyloxy, [di-($C_{1-3}$-alkyl)-amino]-$C_{1-3}$-alkyloxy, amino-$C_{1-3}$-alkyl or $C_{1-4}$-alkoxy-carbonylamino-$C_{1-3}$-alkyl group and in the above-mentioned cycloalkyleneimino and cycloalkyleneiminocarbonyl group a methylene group in position 3 or 4 may be replaced by an —N—, —N($C_{1-3}$-alkyl)- or —N($C_{1-4}$-alkoxy-carbonyl)- group or by an oxygen or sulphur atom and/or in position 2, 3 or 4 by a carbonyl group, a straight-chain or branched $C_{2-6}$-alkyl group which is substituted from position 2 onwards by a hydroxy, $C_{1-3}$-alkoxy, ω-hydroxy-$C_{2-3}$-alkoxy, amino, $C_{1-3}$-alkylamino, di-($C_{1-3}$-alkyl)-amino, $C_{1-3}$-alkyl-carbonylamino, N—($C_{1-3}$-alkyl)-N—($C_{1-3}$-alkyl-carbonyl)-amino, $C_{1-4}$-alkoxy-carbonylamino, N—($C_{1-3}$-alkyl)-N—($C_{1-4}$-alkoxy-carbonyl)-amino, phenylcarbonylamino, N—($C_{1-3}$-alkyl)-N-(phenylcarbonyl)-amino, di-(ω-hydroxy-$C_{2-3}$-alkyl)-amino, pyridinylamino, nitro-pyridinyl-amino, chloro-trifluoromethyl-pyridinylamino, $C_{1-3}$-alkyl-sulphonylamino, N—($C_{1-3}$-alkyl)-N—($C_{1-3}$-alkylsulphonyl)-amino or $C_{1-3}$-alkoxy-carbonyl-$C_{1-3}$-alkyl-carbonylamino group and may optionally additionally be substituted from position 1 onwards by a carboxy, $C_{1-4}$-alkoxy-carbonyl, phenyl, pyridinyl, imidazolyl, $C_{1-3}$-alkylaminocarbonyl, di-($C_{1-3}$-alkyl)-aminocarbonyl, phenylaminocarbonyl, di-(ω-hydroxy-$C_{2-3}$-alkyl)-aminocarbonyl or by a 5 to 7-membered cycloalkyleneimino or cyclo-alkyleneiminocarbonyl group, while in the above-mentioned cycloalkyleneimino or cycloalkyleneiminocarbonyl group a methylene group in position 3 or 4 may be replaced by an —NH—, —N($C_{1-3}$-alkyl)- or —N($C_{1-4}$-alkoxy-carbonyl)- group or by an oxygen or sulphur atom and/or in position 2, 3 or 4 may be replaced by a carbonyl group, and the above-mentionedn phenyl groups may optionally be substituted by an amino-$C_{1-3}$-alkyl or $C_{1-4}$-alkoxy-carbonylamino-$C_{1-3}$-alkyl group, or or represent a propenyl or propynyl group, the tautomers, enantiomers, diastereomers, the mixtures thereof and the salts thereof.

4. Compounds of general formula I according to claim 3, wherein $R^1$ denotes a methyl group, $R^2$ denotes an ethyl, propyl, butyl or pentyl group, a phenyl group wherein two adjacent carbon atoms are linked together through a methylenedioxy, ethylenedioxy or difluoromethylenedioxy group, or a phenyl group which may be substituted by one or two fluorine, chlorine or bromine atoms or by one or two trifluoromethyl, nitro, cyano, $C_{1-3}$-alkoxy, carboxy-$C_{1-3}$-alkyl, $C_{1-3}$-alkoxy-carbonyl-$C_{1-3}$-alkyl, amino-$C_{1-3}$-alkyl or $C_{1-3}$-alkyl-carbonylamino-$C_{1-3}$-alkyl-groups, while the substituents are identical or different, and $R^3$ denotes a straight-chain or branched $C_{1-5}$-alkyl group which may be substituted by a carboxy, $C_{1-4}$-alkoxy-carbonyl, $C_{1-3}$-alkylaminocarbonyl, di-($C_{1-3}$-alkyl)-aminocarbonyl, phenylaminocarbonyl, pyridinylaminocarbonyl, di-(2-hydroxy-ethyl)-aminocarbonyl, piperazinylcarbonyl, 4-($C_{1-3}$-alkyl)-piperazinyl-carbonyl, 4-($C_{1-4}$-alkoxy-carbonyl)-piperazinyl-carbonyl, phenyl, pyridinyl or imidazolyl group, while the phenyl group may optionally be substituted by a nitro, cyano, $C_{1-3}$-alkyloxy, [di-($C_{1-3}$-alkyl)-amino]-$C_{1-3}$-alkyloxy, amino-$C_{1-3}$-alkyl or $C_{1-4}$-alkoxy-carbonylamino-$C_{1-3}$-alkyl group, a $C_{2-5}$-alkyl group which is terminally substituted by a hydroxy, $C_{1-3}$-alkoxy, phenyloxy, 2-hydroxy-ethoxy, amino, $C_{1-3}$-alkylamino, di-($C_{1-3}$-alkyl)-amino, $C_{1-3}$-alkyl-carbonylamino, N—($C_{1-3}$-alkyl)-N—($C_{1-3}$-alkyl-carbonyl)-amino, $C_{1-4}$-alkoxy-carbonylamino, N—($C_{1-3}$-alkyl)-N—($C_{1-4}$-alkoxy-carbonyl)-amino, phenylcarbonylamino, N—($C_{1-3}$-alkyl)-N-(phenyl-carbonyl)-amino, pyridinylamino, nitro-pyridinyl-amino, di-(2-hydroxy-ethyl)-amino, 3-chloro-5-trifluoromethyl-pyridin-2-yl-amino, $C_{1-3}$-alkylsulphonylamino, N—($C_{1-3}$-alkyl)-N—($C_{1-3}$-alkylsulphonyl)-amino, $C_{1-3}$-alkoxy-carbonyl-$C_{1-3}$-alkyl-carbonylamino, indolyl, pyrrolidinyl, 2-oxo-pyrrolidinyl, morpholinyl, piperazinyl or 4-($C_{13}$-alkyl)-piperazinyl group and may optionally additionally be substituted from position 1 onwards by a carboxy, $C_{1-4}$-alkoxy-carbonyl, $C_{1-3}$-alkylaminocarbonyl, di-($C_{1-3}$-alkyl)-aminocarbonyl, phenylaminocarbonyl, di-(2-hydroxy-ethyl)-aminocarbonyl, piperazinylcarbonyl, 4-($C_{1-3}$-alkyl)-piperazinyl-carbonyl, 4-($C_{1-4}$-alkoxy-carbonyl)-piperazinyl-carbonyl, phenyl, pyridinyl or imidazolyl group, or an amino group which may be substituted by one or two $C_{1-3}$-alkyl, aryl, aryl-$C_{1-3}$-alkyl, $C_{1-3}$-alkyl-carbonyl, $C_{1-4}$-alkyloxy-carbonyl, arylcarbonyl or aryl-$C_{1-3}$-alkyl-carbonyl groups, while the substituents may be identical or different, while the above-mentioned alkyl groups may be straight-chain or branched, the tautomers, enantiomers, diastereomers, the mixtures thereof and the salts thereof.

5. Compounds of general formula I according to claim 4, wherein $R^1$ denotes a methyl group, $R^2$ denotes an ethyl, propy, butyl or pentyl group, a phenyl group wherein two adjacent carbon atoms are linked together through a methylenedioxy or ethylenedioxy group, or a phenyl group and $R^3$ denotes a $C_{1-4}$-alkyl group which may be terminally substituted by a $C_{1-4}$-alkoxy-carbonyl group, or a $C_{2-4}$-alkyl group which is terminally substituted by a $C_{1-3}$-alkyl-carbonylamino, phenyl-carbonylamino, di-($C_{1-3}$-alkyl)-amino, phenyl, pyridinyl or $C_{1-3}$-alkylsulphonylamino group, while the above-mentioned alkyl groups may be straight-chain or branched, the tautomers, enantiomers, diastereomers, the mixtures thereof and the salts thereof.

6. The following compounds of general formula I according to claim 1:

(a) 5-acetyl-3-[3-(methoxycarbonylpropylamino)-(benzo-[1.3]dioxyo-5-yl)-methylidene]-2-indolinone

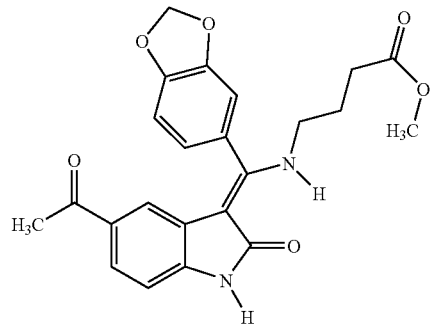

(b) 5-acetyl-3-[isopropylamino-phenyl-methylidene]-2-indolinone

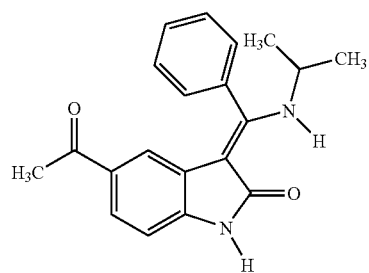

(c) 5-acetyl-3-[propylamino-phenyl-methylidene]-2-indolinone

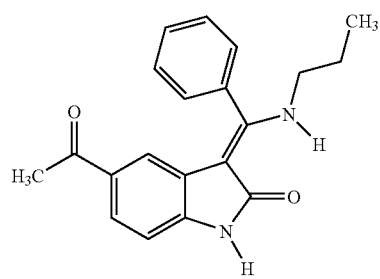

(d) 5-acetyl-3-[(3-methoxycarbonyl-propylamino)-(2.3-dihydro-benzo[1.4]dioxin-6-yl)-methylidene]-2-indolinone

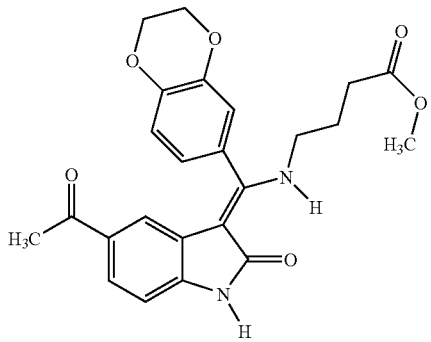

(e) 5-acetyl-3-[(benzo[1.3]dioxol-5-yl)-(3-(benzoylamino-propylamino)-methylidene]-2-indolinone

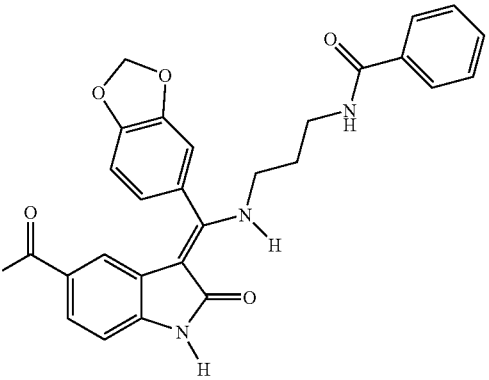

(f) 5-acetyl-3-[(benzo[1.3]dioxol-5-yl)-(3-(butyrylamino-propylamino)-methylidene]-2-indolinone

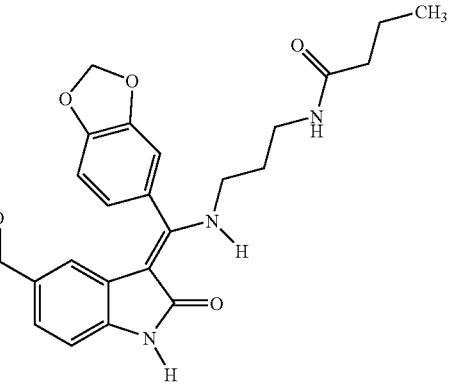

(g) 5-acetyl-3-[(3-methanesulphonylamino-propylamino)-phenyl-methylidene]-2-indolinone

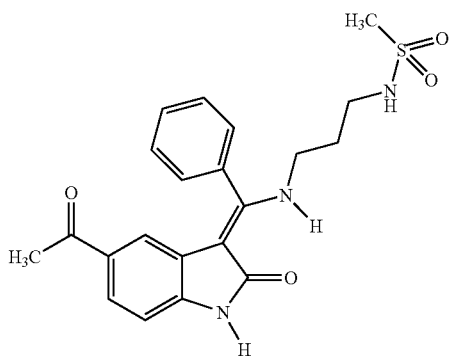

(h) 5-acetyl-3-[1-(3.4-difluorophenyl)-1-(N',N'-dimethylhydrazino)-methylidene]-2-indolinone

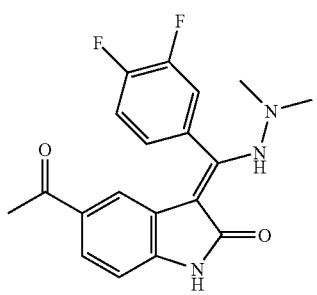

(i) 5-acetyl-3-[1-(4-dimethylamino-butyl)-butenylidene]-2-indolinone

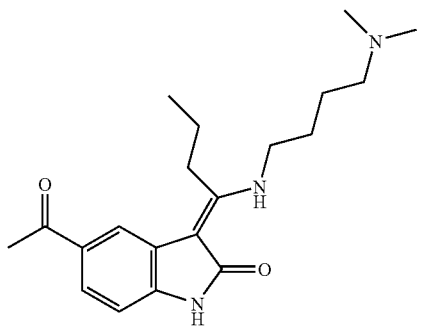

(j) 5-acetyl-3-[1-phenyl-1-(3-pyridin-3-yl-propylamino)-methylidene]-2-indolinone

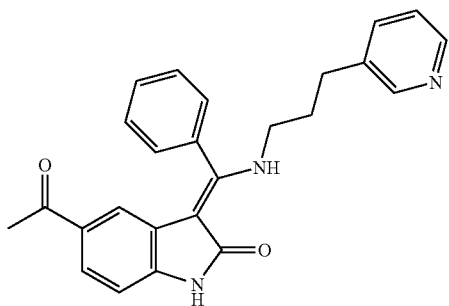

and the tautomers, enantiomers, diastereomers, the mixtures thereof and the salts thereof.

7. Physiologically acceptable salts of the compounds according to claim 1 with inorganic or organic acids or bases.

8. Pharmaceutical compositions containing a compound according to claim 1 or a physiologically acceptable salt thereof with inorganic or organic acids or bases optionally together with one or more inert carriers and/or diluents.

9. Process for preparing a pharmaceutical composition according to claim 8, characterised in that said compound is incorporated in one or more inert carriers and/or diluents by a non-chemical method.

10. A method of treating type I and type II diabetes mellitus, diabetes associated disorders selected from diabetic neuropathy and degenerative neurological diseases selected from Alzheimer's disease, stroke, neurotraumatic injuries and bipolar disorders, said method comprised of the steps of administering to a patient in need therof an effective amount of a compound according to claim 1 or a pharmaceutically accapetable salt thereof.

11. Process for preparing the compounds of general formula I according to claims 1 comprised of the steps of:
a) reacting a compound of general formula

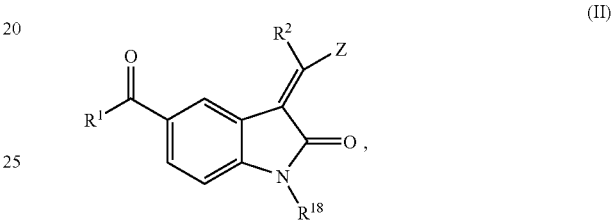

(II)

wherein $R^1$ and $R^2$ are defined as in claim 1,
$R^{18}$ denotes a hydrogen atom or a protective group for the nitrogen atom of the lactam group and
Z denotes a leaving group such as for example a halogen atom, a hydroxy, alkoxy, alkyl-sulphonyl, aralkylsulphonyl, or aryl-alkoxy group, e.g. a chlorine or bromine atom, a methoxy, ethoxy, methanesulphonyl, toluenesulphonyl or benzyloxy group,
with an amine of general formula $$R^3-NH_2 \quad (III),$$

wherein $R^3$ is defined as in claim 1, while any hydroxy, amino or imino groups contained in the groups $R^2$ and/or $R^3$ may temporarily be protected by suitable protective groups,
said method further characterized in that:
in order to prepare a compound of formula I which contains an aminocarbonyl group, a compound which contains a carboxy group is reacted with the corresponding amine,
in order to prepare a compound of formula I which contains a carbonylamino group, a compound which contains an amino group is reacted with the corresponding acid chloride,
in order to prepare a compound of formula I which contains an aminomethyl group, a compound which contains a cyano group is hydrogenated to form the corresponding aminomethyl derivative,
in order to prepare a compound of formula I which contains an amino group, a compound which contains a nitro group is hydrogenated,
and/or
any protective groups which may be used during the reaction are then cleaved and/or
the compounds of general formula I thus obtained are resolved into their enantiomers and/or diastereomers and/or
the compounds of general formula I thus obtained are converted into their salts, particularly for pharmaceutical use into the physiologically acceptable salts thereof with inorganic or organic acids or bases.

* * * * *